US009757470B2

(12) United States Patent
Narasimhaswamy et al.

(10) Patent No.: US 9,757,470 B2
(45) Date of Patent: *Sep. 12, 2017

(54) PEPTIDES FOR ASSISTING DELIVERY ACROSS THE BLOOD BRAIN BARRIER

(71) Applicant: Children's Medical Center Corporation, Boston, MA (US)

(72) Inventors: Manjunath Narasimhaswamy, El Paso, TX (US); Premlata Shankar, El Paso, TX (US); Priti Kumar, Hamden, CT (US)

(73) Assignee: Children's Medical Center Corporation, Boston, MA (US)

( * ) Notice: Subject to any disclaimer, the term of this patent is extended or adjusted under 35 U.S.C. 154(b) by 257 days.

This patent is subject to a terminal disclaimer.

(21) Appl. No.: 14/265,939

(22) Filed: Apr. 30, 2014

(65) Prior Publication Data

US 2014/0294727 A1 Oct. 2, 2014

Related U.S. Application Data

(63) Continuation of application No. 12/301,847, filed as application No. PCT/US2007/012152 on May 22, 2007, now Pat. No. 8,748,567.

(60) Provisional application No. 60/802,377, filed on May 22, 2006.

(51) Int. Cl.
*A61K 47/48* (2006.01)
*A61K 49/00* (2006.01)
*B82Y 5/00* (2011.01)

(52) U.S. Cl.
CPC .. *A61K 47/48246* (2013.01); *A61K 47/48238* (2013.01); *A61K 47/48315* (2013.01); *A61K 47/48323* (2013.01); *A61K 47/48815* (2013.01); *A61K 47/48969* (2013.01); *A61K 49/0056* (2013.01); *B82Y 5/00* (2013.01)

(58) Field of Classification Search
None
See application file for complete search history.

(56) References Cited

U.S. PATENT DOCUMENTS

| | | | |
|---|---|---|---|
| 5,716,614 A | 2/1998 | Katz et al. | |
| 2002/0168760 A1 | 11/2002 | Dornburg et al. | |
| 2003/0099671 A1 | 5/2003 | Fu | |
| 2004/0043457 A1* | 3/2004 | Schumacher | A61K 38/47 435/69.7 |
| 2004/0102369 A1 | 5/2004 | Wu et al. | |
| 2004/0266715 A1 | 12/2004 | Wong et al. | |
| 2005/0239687 A1 | 10/2005 | Divita et al. | |

FOREIGN PATENT DOCUMENTS

| | | |
|---|---|---|
| WO | 2004/031390 A1 | 4/2004 |
| WO | 2007/047459 A1 | 4/2007 |

OTHER PUBLICATIONS

AnaSpec (available online May 3, 2006) document 1.*
AnaSpec (available online May 3, 2006) document 2.*
AnaSpec (available online May 3, 2006) document 3.*
Chen et al. (Chemistry & Biology 8 (2001) 1123-1129).*
GenScript Cat. RP20164 (available online Nov. 8, 2004) document 1.*
GenScript Cat. RP20164 (available online Nov. 8, 2004) document 2.*
Biggerstaff et al., "Estimated Risk of Transmission of the West Nile Virus Through Blood Transfusion in the US, 2002," Transfusion 43:1007-17 (2003).
Borlongan et al., "Bradykinin Receptor Agonist Facilitates Low-Dose Cyclosporine-A Protection Against 6-Hydroxydopamine Neurotoxicity," Brain Research 956:211-20 (2002).
Chen et al., "Implication of nNOS in the Enlargement of AChR Aggregates But Not the Initial Aggregate Formation in a Novel Coculture Model," Chinese Journal of Physiology 48(3):129-38 (2005).
Chiu et al., "Visualizing a Correlation Between siRNA Localization, Cellular Uptake, and RNAi in Living Cells," Chemistry and Biology 11:1165-75 (2004).
Deshayes et al., "Cell-Penetrating Peptides: Tools for Intracellular Delivery of Therapeutics," Cell. Mol. Life Sci. 62:1839-49 (2005).
Dietzschold et al., "Pathogenesis of Rabies," CTMI 292:45-56 (2005).
Dixon, "Natural Products and Plant Disease Resistance," Nature 411:843-7 (2005).
Donnelly-Roberts et al., "Structural and Conformational Similarity Between Synthetic Peptides of Curaremimetic Neurotoxins and Rabies Virus Glycoprotein," Molecular Brain Research 11:107-113 (1991).
Gotti et al., "Neuronal Nicotinic Receptors: From Structure to Pathology," Progress in Neurobiology 74:363-96 (2004).
Kroll et al., "Outwitting the Blood-Brain Barrier for Therapeutic Purposes: Osmotic Opening and Other Means," Neurosurgery 42(5):1083-100 (1998).
Kumar et al., "A Single siRNA Suppresses Fatal Encephalitis Induced by Two Different Flaviviruses," PLoS Medicine 3(4):0505-14 (2006).
Lafon, "Rabies Virus Receptors," Journal of NeuroVirology 11:82-7 (2005).
Lentz et al., "Amino Acid Sequence Similarity Between Rabies Virus Glycoprotein and Snake Venom Curaremimetic Neurotoxins," Science 226(4676):847-8 (1984).
Lentz et al., "Is the Acetylcholine Receptor a Rabies Virus Receptor?" Science 215(4529):182-4 (1982).

(Continued)

*Primary Examiner* — James H Alstrum Acevedo
*Assistant Examiner* — Tara Martinez
(74) *Attorney, Agent, or Firm* — Nixon Peabody LLP

(57) ABSTRACT

The present invention provides compositions and methods useful for delivering agents to target cells or tissues, for example nerve cells and other cells in the central nervous system. The compositions and methods are useful for delivering agents across the blood-brain barrier. The present invention also provides methods of using the compositions provided by the present invention to deliver agents, for example therapeutic agents for the treatment of neurologically related disorders.

16 Claims, 40 Drawing Sheets

(56) References Cited

OTHER PUBLICATIONS

Lentz, "Rabies Virus Binding to an Acetylcholine Receptor a-Subunit Peptide," Journal of Molecular Recognition 3 (2):82-8 (1990).
Lentz, "Structure-Function Relationships of Curaremimetic Neurotoxin Loop 2 and of a Structurally Similar Segment of Rabies Virus Glycoprotein in Their Interaction with the Nicotinic Acetylcholine Receptor," Biochemistry 30:10949-57 (1991).
Makimura et al., "Reducing Hypothalamic AGRP by RNA Interference Increases Metabolic Rate and Decreases body Weight Without Influencing Food Intake," BMC Neuroscience 3(1):18 (2002.
Melikov et al., "Arginine-Rich Cell Penetrating Peptides: From Endosomal Uptake to Nuclear Delivery," Cell. Mol. Life Sci. 62:2739-49 (2005).
Muldoon et al., "Comparison of Intracerebral Inoculation and Osmotic Blood-Brain Barrier Disruption for Delivery of Adenovirus, Herpesvirus, and Iron Oxide Particles to Normal Rat Brain," American Journal of Pathology 147(6):1840-51 (1995).
Notter et al., "Flow Cytometric Analysis of Tetanus Toxin Binding to Neuroblastoma Cells," Journal of Cellular Physiology 125:476-84 (1985).
Rice, "Flaviviridae: The Viruses and Their Replication," Fields Virology pp. 931-959 (1996).
Shi et al., "Receptor-Mediated Gene Targeting to Tissues In Vivo Following Intravenous Administration of Pegylated Immunoliposomes," Pharmaceutical Research 18(8):1091-5 (2001).
Sumimoto et al., "Gene Therapy for Human Small-Cell Lung Carcinoma by Inactivation of Skp-2 with Virally Mediated RNA Interference," Gene Therapy 12:95-100 (2005).
Thakker et al., "Neurochemical and Behavioral Consequences of Widespread Gene Knockdown in the Adult Mouse Brain by Using Nonviral RNA Interference," PNAS 101(49):17270-5 (2004).
Wender et al., "The Design, Synthesis, and Evaluation of Molecules that Enable or Enhance Cellular Uptake: Peptoid Molecular Transporters," PNAS 97(24):13003-8 (2000).
Xia et al., "siRNA-Mediated Gene Silencing In Vitro and In Vivo," Nature Biotechnology 20:1006-10 (2002).
Zhang et al., "Global Non-Viral Gene Transfer to the Primate Brain Following Intravenous Administration," Molecular Therapy 7(1):11-18 (2003).
Zhang et al., "In Vivo Knockdown of Gene Expression in Brian Cancer with Intravenous RNAi in Adult Rats," J Gene Med 5:1039-45 (2003).
Zhu et al., "Organ-Specific Expression of the lacZ Gene Controlled by the Opsin Promoter After Intravenous Gene Administration in Adult Mice," J Gene Med 6:906-12 (2004).
Mazarakis, ND et al., "Rabies virus glycoprotein pseudotyping of lentiviral vectors enables retrograde axonal transport and access to the nervous system after peripheral delivery." Human Molecular Genetics 10(19):2109-2121, 2001.
Oth et al, "The Association of the Rabies Glycoprotein With Liposome (Immunosome) Induces an In Vitro Specific Release of Interleukin 2," Cellular Immunology, vol. 108, No. 1, pp. 220-226, 1987.
Xuan et al., "Biological and immunogenic properties of rabies virus glycoprotein expressed by canine herpervirus vector," Vaccine, vol. 16, No. 9/10, pp. 969-976, 1998.

* cited by examiner

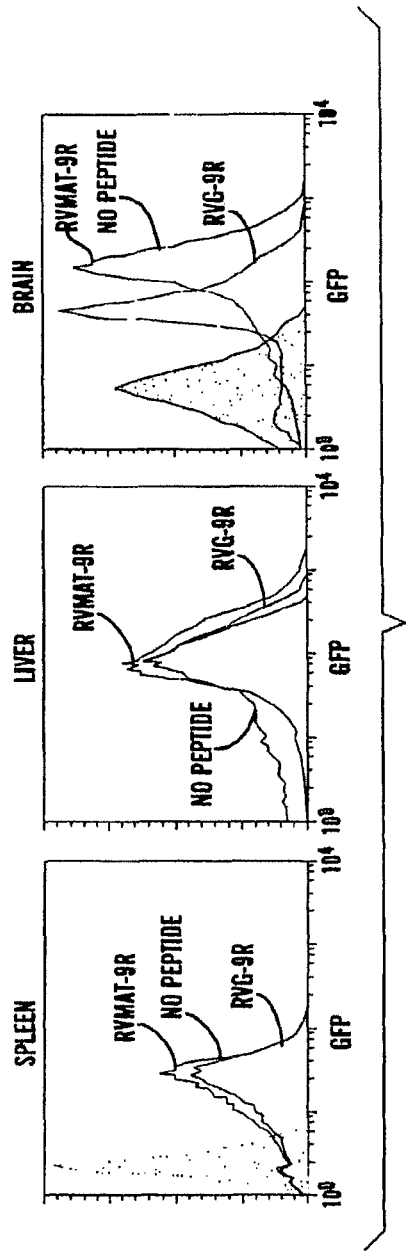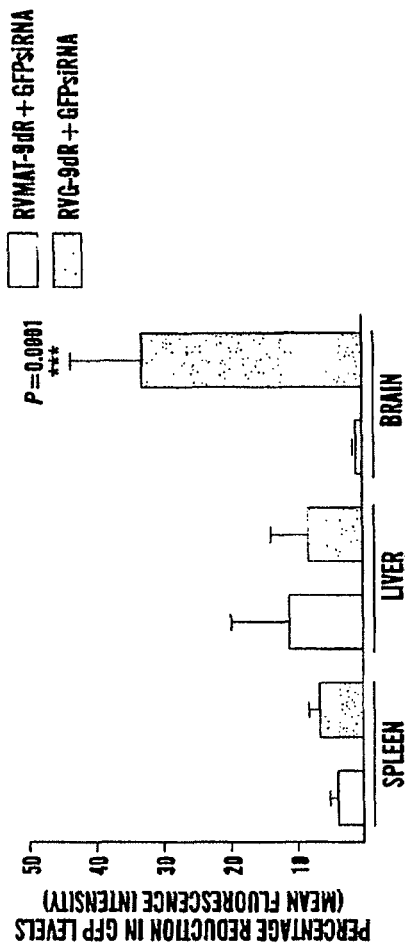
FIG. 25A
FIG. 25B

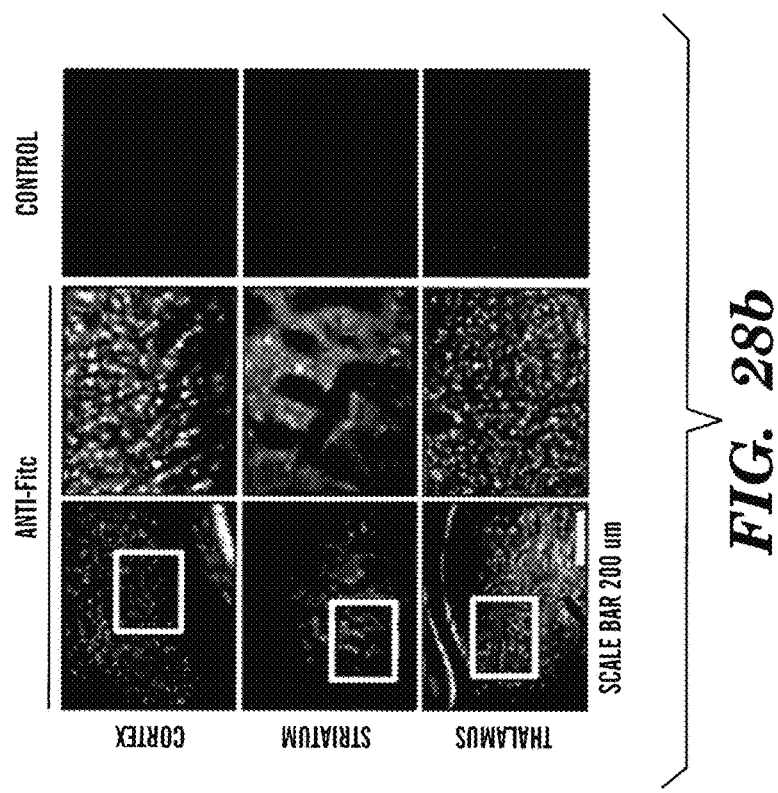
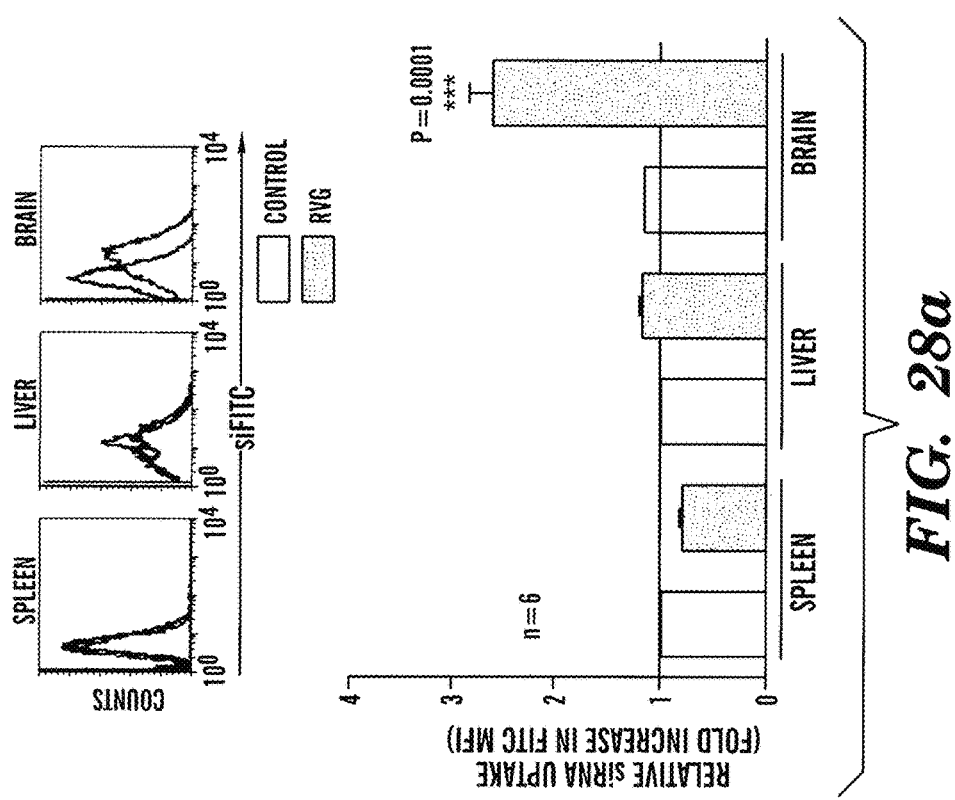
FIG. 28b
FIG. 28a

FIG. 30a

SEQUENCE LISTING

```
<160> NUMBER OF SEQ ID NOS: 35

<210> SEQ ID NO 1
<211> LENGTH: 9
<212> TYPE: PRT
<213> ORGANISM: Human immunodeficiency virus type 1

<400> SEQUENCE: 1

Arg Lys Lys Arg Gln Arg Arg Arg
 1               5

<210> SEQ ID NO 2
<211> LENGTH: 13
<212> TYPE: PRT
<213> ORGANISM: Human immunodeficiency virus type 1

<400> SEQUENCE: 2

Gly Arg Lys Lys Arg Arg Gln Arg Arg Arg Thr Pro Gln
 1               5                   10

<210> SEQ ID NO 3
<211> LENGTH: 11
<212> TYPE: PRT
<213> ORGANISM: Human immunodeficiency virus type 1

<400> SEQUENCE: 3

Tyr Gly Arg Lys Lys Arg Arg Gln Arg Arg Arg
 1               5                   10
```

```
<210> SEQ ID NO 4
<211> LENGTH: 26
<212> TYPE: PRT
<213> ORGANISM: Kaposi's sarcoma-associated herpesvirus

<400> SEQUENCE: 4

Ala Ala Val Ala Leu Leu Pro Ala Val Leu Ala Leu Leu Ala Pro
 1               5                  10                  15

Val Gln Arg Lys Arg Gln Lys Leu Met Pro
            20                  25

<210> SEQ ID NO 5
<211> LENGTH: 17
<212> TYPE: PRT
<213> ORGANISM: Caiman crocodylus

<400> SEQUENCE: 5

Met Gly Leu Gly Leu His Leu Leu Val Leu Ala Ala Ala Leu Gln Gly
 1               5                  10                  15

Ala

<210> SEQ ID NO 6
<211> LENGTH: 23
<212> TYPE: PRT
<213> ORGANISM: Human immunodeficiency virus type 1

<400> SEQUENCE: 6

Gly Ala Leu Phe Leu Gly Phe Leu Gly Ala Ala Gly Ser Thr Met Gly
 1               5                  10                  15

Ala Pro Lys Ser Lys Arg Lys
            20

<210> SEQ ID NO 7
<211> LENGTH: 16
<212> TYPE: PRT
<213> ORGANISM: Drosophila melanogaster

<400> SEQUENCE: 7

Arg Gln Ile Lys Ile Trp Phe Gln Asn Arg Arg Met Lys Trp Lys Lys
 1               5                  10                  15

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: variable amino acid
<220> FEATURE:
<221> NAME/KEY: MOD_RES
<222> LOCATION: (5)
<223> OTHER INFORMATION: variable amino acid

<400> SEQUENCE: 8

Xaa Arg Gly Asp Xaa
 1               5

<210> SEQ ID NO 9
<211> LENGTH: 24
<212> TYPE: PRT
<213> ORGANISM: Influenza virus
```

```
<400> SEQUENCE: 9

Gly Leu Phe Glu Ala Ile Ala Gly Phe Ile Glu Asn Gly Trp Glu Gly
 1               5                  10                  15

Met Ile Asp Gly Gly Gly Tyr Cys
            20

<210> SEQ ID NO 10
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Trp Thr Leu Asn Ser Ala Gly Tyr Leu Leu Gly Lys Ile Asn Leu
 1               5                  10                  15

Lys Ala Leu Ala Ala Leu Ala Lys Lys Ile Leu
            20                  25

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: may or may not be present

<400> SEQUENCE: 11

Ser Asp His Gln Leu Asn Pro Ala Phe
 1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: may or may not be present

<400> SEQUENCE: 12

Ser Phe Cys Tyr Trp Lys Thr Cys Thr
 1               5

<210> SEQ ID NO 13
<211> LENGTH: 29
<212> TYPE: PRT
<213> ORGANISM: Rabies virus

<400> SEQUENCE: 13

Tyr Thr Ile Trp Met Pro Glu Asn Pro Arg Pro Gly Thr Pro Cys Asp
 1               5                  10                  15

Ile Phe Thr Asn Ser Arg Gly Lys Arg Ala Ser Asn Gly
            20                  25

<210> SEQ ID NO 14
<211> LENGTH: 43
```

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Tyr Thr Ile Trp Met Pro Glu Asn Pro Arg Pro Gly Thr Pro Cys Asp
 1               5                  10                  15

Ile Phe Thr Asn Ser Arg Gly Lys Arg Ala Ser Asn Gly Gly Gly Gly
            20                  25                  30

Arg Arg Arg Arg Arg Arg Arg Arg Arg Arg
        35                  40

<210> SEQ ID NO 15
<211> LENGTH: 47
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Tyr Thr Ile Trp Met Pro Glu Asn Pro Arg Pro Gly Thr Pro Cys Asp
 1               5                  10                  15

Ile Phe Thr Asn Ser Arg Gly Lys Arg Ala Ser Asn Gly Gly Gly Gly
            20                  25                  30

Tyr Gly Arg Lys Lys Arg Arg Gln Arg Arg Lys Lys Arg Lys
        35                  40                  45

<210> SEQ ID NO 16
<211> LENGTH: 54
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Tyr Thr Ile Trp Met Pro Glu Asn Pro Arg Pro Gly Thr Pro Cys Asp
 1               5                  10                  15

Ile Phe Thr Asn Ser Arg Gly Lys Arg Ala Ser Asn Gly Gly Gly Gly
            20                  25                  30

Arg Ser Gln Ser Arg Ser Arg Tyr Tyr Arg Gln Arg Gln Arg Ser Arg
        35                  40                  45

Arg Arg Arg Arg Arg Ser
    50

<210> SEQ ID NO 17
<211> LENGTH: 26
<212> TYPE: PRT
<213> ORGANISM: Kaposi's sarcoma-associated herpesvirus

<400> SEQUENCE: 17

Ala Ala Val Ala Leu Leu Pro Ala Val Leu Leu Ala Leu Leu Ala Pro
 1               5                  10                  15

Ala Ala Ala Asp Gln Asn Gln Leu Met Pro
            20                  25

<210> SEQ ID NO 18
<211> LENGTH: 34
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 18

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Arg Trp Arg Arg Trp Trp Arg Arg Trp Trp Arg Arg Trp Arg Arg
1               5                   10                  15

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Arg Arg Arg Arg Arg Arg
1               5

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Pro Lys Lys Arg Lys Val Arg Arg Arg
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Lys Lys Lys Lys Lys Lys Lys Lys Gly Gly Cys
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 23

Lys Trp Lys Lys Lys Trp Lys Lys Gly Cys Cys
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Trp Arg Arg Arg Trp Arg Arg Gly Gly Cys
1               5                   10

<210> SEQ ID NO 25
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Ala Leu Phe Leu Gly Phe Leu Gly Gly Ala Ala Gly Ser Thr Met
1               5                   10                  15

Gly Ala Trp Ser Gln Pro Lys Ser Lys Arg Lys Val
            20                  25

<210> SEQ ID NO 26
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 27
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asp Pro Lys Gly Asp Pro Lys Gly Val Thr Val Thr Val Thr Val Thr
1               5                   10                  15

Val Thr Gly Lys Gly Asp Pro Lys Pro Asp
            20                  25

<210> SEQ ID NO 28
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 28

Lys Leu Ala Leu Lys Leu Ala Leu Lys Ala Leu Lys Ala Ala Leu Lys
 1               5                  10                  15

Leu Ala

<210> SEQ ID NO 29
<211> LENGTH: 18
<212> TYPE: PRT
<213> ORGANISM: Mus musculus

<400> SEQUENCE: 29

Leu Leu Ile Ile Leu Arg Arg Arg Ile Arg Lys Gln Ala His Ala His
 1               5                  10                  15

Ser Lys

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Val Ile Arg Val Trp Phe Gln Asn Lys Arg Cys Lys Asp Lys Lys
 1               5                  10                  15

<210> SEQ ID NO 31
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Lys Glu Thr Trp Trp Glu Thr Trp Trp Thr Glu Trp Ser Gln Pro Lys
 1               5                  10                  15

Lys Lys Arg Lys Val
            20

<210> SEQ ID NO 32
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Met Ala Asn Leu Gly Tyr Trp Leu Leu Ala Leu Phe Val Thr Met Trp
 1               5                  10                  15

Thr Asp Val Gly Leu Cys Lys Lys Arg Pro Lys Pro
            20                  25

<210> SEQ ID NO 33
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33
```

-continued

```
Met Asn Leu Leu Arg Lys Ile Val Lys Asn Arg Arg Asp Glu Asp Thr
1               5                   10                  15

Gln Lys Ser Ser Pro Ala Ser Ala Pro Leu Asp Asp Gly
            20                  25

<210> SEQ ID NO 34
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Tyr Thr Ile Trp Met Pro Glu Asn Pro Arg Pro Gly Thr Pro Cys Asp
1               5                   10                  15

Ile Phe Thr Asn Ser Arg Gly Lys Arg Ala Ser Asn Gly Gly Gly Gly
            20                  25                  30

Arg Arg Arg Arg Arg Arg Arg Arg Arg
            35                  40

<210> SEQ ID NO 35
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Met Asn Leu Leu Arg Lys Ile Val Lys Asn Arg Arg Asp Glu Asp Thr
1               5                   10                  15

Gln Lys Ser Ser Pro Ala Ser Ala Pro Leu Asp Asp Gly Gly Gly Gly
            20                  25                  30

Arg Arg Arg Arg Arg Arg Arg Arg Arg
            35                  40
```

PEPTIDES FOR ASSISTING DELIVERY ACROSS THE BLOOD BRAIN BARRIER

CROSS REFERENCED TO RELATED APPLICATIONS

This application is a Continuation Application of Ser. No. 12/301,847, filed on Nov. 21, 2008, which is a National Phase Entry Application under 35 U.S.C. §371 of the International Application PCT/US2007/012152, filed May 22, 2007, which claims the benefit under 35 U.S.C. §119(e) of U.S. Provisional Application Ser. No. 60/802,377 filed on May 22, 2006, the contents of each are incorporated herein in their entirety by reference.

GOVERNMENT SUPPORT

This invention was supported, in part, by National Institutes of Health (NIH) Grant No. U19 AI056900. The government of the United States has certain rights to the invention.

SEQUENCE LISTING

The instant application contains a Sequence Listing which has been submitted in ASCII format via EFS-Web and is hereby incorporated by reference in its entirety. Said ASCII copy, created on Apr. 29, 2014, is named Sequence_Listing.txt and is 12,542 bytes in size.

FIELD OF THE INVENTION

The present invention relates generally to the field of drug delivery and more specifically to the delivery of agents to the central nervous system, and delivery of agents for the treatment of neurologically related conditions in the central nervous system and other target cells.

BACKGROUND OF THE INVENTION

The blood brain barrier (BBB) is a system-wide membrane barrier that prevents the brain uptake of circulating drugs, protein therapeutics, RNAi drugs, and gene medicines. Drugs or genes can be delivered to the human brain for the treatment of serious brain disease either (a) by injecting the drug or gene directly into the brain, thus bypassing the BBB, or (b) by injecting the drug or gene into the bloodstream so that the drug or gene enters the brain via the transvascular route across the BBB. With intra-cerebral administration of the drug, it is necessary to drill a hole in the head and perform a procedure called craniotomy. In addition to being expensive and highly invasive, this craniotomy based drug delivery to the brain approach is ineffective, because the drug or gene is only delivered to a tiny volume of the brain at the tip of the injection needle. The only way the drug or gene can be distributed widely in the brain is the transvascular route following injection into the bloodstream. However, this latter approach requires the ability to undergo transport across the BBB. The BBB has proven to be a very difficult and stubborn barrier to traverse safely.

The traditional approach to delivery of drugs across the BBB is called "BBB disruption". One of the earliest techniques tried is the transient disruption of the barrier (BBBD) by infusing hyperosmolar solutions, which sucks water out of capillary endothelial cells, thereby shrinking them to open the gaps [47-49]. Another approach to disrupt BBB is the use of bradykinin receptor agonists, such as the compound RMP7 (Cereport, Alkermes), which binds to the receptors on the surface of endothelial cells and kicks off a biochemical cascade that loosens the tight junctions [50]. However, none of these methods is very effective and moreover, they suffer from the drawback that BBB disruption also allows the non-specific entry of other potentially brain-toxic molecules such as serum albumin. Accordingly, this approach has not gained widespread clinical acceptance.

Transvascular approach provides the most ideal noninvasive means to treat neurological diseases. If not for the BBB, the capillaries, which stretch for over 400 miles in the brain and encase virtually every brain cell, would offer the most promising delivery approach [46]. The most promising transvascular approach to brain is to use transporter molecules since this allows delivery of specific molecules without disrupting the BBB [46]. A peptidomimetic mAb, such as against the transferrin receptor can be used as a molecular "Trojan horse" to ferry any attached drug or gene across the BBB. Recently, great progress has been made in brain delivery by combining the antibody targeting technology with siRNA encapsulation within liposomes [46]. The problems associated with the use of conventional cationic polyplexes, such as the aggregation of the DNA and sequestration in the lung and liver can be eliminated if the DNA is encapsulated in the interior of a nanocontainer such as a liposome or a polymeric nanoparticle. If the surface of the liposome is conjugated with polyethylene glycol or hyaluron, this makes the liposome stable in blood with prolonged blood residence times. If the tips of PEG or hyaluron are conjugated with a BBB molecular "Trojan horse", such as anti-transferrin receptor antibody, this immunoliposome is effectively delivered across the BBB. This system has been used to deliver reporter genes with success in the rat, mice and monkey brains [76-81]. Recently, this technology has also been used to deliver shRNAs to target specific genes in brain tumors in mice as well as monkeys [37,82]. Thus, this method seems optimal to introduce shRNA encoding vectors as well as synthetic siRNA duplexes.

SUMMARY OF THE INVENTION

The inventors have discovered a method to deliver agents across the blood brain barrier (BBB). As disclosed herein, one embodiment of the present invention relates to methods to deliver agents across the blood brain barrier. In another embodiment, the present invention provides methods to deliver agents to a cell, for example a cell with acetyl choline receptors (AchR) present on the surface of the cell. For example, the present invention provides methods to deliver agents to a CNS cell.

In one aspect, the present invention relates to a composition comprising a targeting agent, wherein targeting agent is conjugated with a carrier particle, and an agent, herein termed an "effector agent" is associated with the carrier particle.

In some embodiments, the targeting agent is an RVG peptide or a derivative or a variant thereof. In alternative embodiments, targeting agents include, for example insulin, transferrin, insulin like growth factor (IGF), leptin, low density lipoprotein (LDL) and fragments or peptidomimetics or derivatives thereof.

In some embodiments, the carrier particle is, for example, a lyposomal or polymeric nanoparticles, for example a liposome, polyarginine, protamine, or a cyclodextrin-based nanoparticle. In alternative embodiments, the carrier particle is a cell permeable agent, for example a cell permeable agent, for example but not limited to, 11dR, 9dR or TAT-HIV or a fragment thereof.

In some embodiments, where the carrier particle is, for example, a lyposomal or polymeric nanoparticles, for example a liposome, polyarginine, protamine, or a cyclodextrin-based nanoparticle, the carrier particle can optionally further comprise cell permeable agents, for example but not limited to, polymeric arginine residues of various lengths such as 11R or 9R as disclosed herein or TAT-HIV or fragments thereof. In other embodiments, the carrier particle can optionally further comprise additional targeting agents, for example, in embodiments where the carrier particle is conjugated to an RVG peptide, the carrier particle can also comprise additional targeting agents, for example insulin, transferrin, insulin like growth factor (IGF), leptin, low density lipoprotein (LDL) and fragments or peptidomimetics or derivatives thereof.

One aspect of the present invention relates to a method for preparing an effector agent for delivery to a cell, comprising associating an effector agent with a carrier particle, wherein the carrier particle is associated with a rabies virus glycoprotein (RVG) peptide comprising SEQ ID NO:13 or a variant, fragment or derivative thereof, wherein the RVG peptide binds to an acetylcholine receptor (AChR) present on the surface of the cell. In such embodiments, a derivative or variant thereof comprises a conservative amino acid substitution.

In another aspect, the present invention relates to a method for delivering an effector agent across the blood-brain barrier of a subject, the method comprising administering to the subject a composition comprising a rabies virus glycoprotein (RVG) peptide comprising SEQ ID NO:13 or a variant, fragment or derivative thereof, wherein the RVG peptide is attached to a carrier particle, and wherein the effector agent is associated with the carrier particle.

A further aspect of the present invention relates to a method for delivering an effector agent to a cell of the CNS, the method comprising contacting the cell with a rabies virus glycoprotein (RVG) peptide comprising SEQ ID NO:13 or a variant, fragment or derivative thereof, wherein the RVG peptide is attached to a carrier particle, and wherein the effector agent is associated with the carrier particle, and the RVG peptide binds to binds to an acetylcholine receptor (AChR) present on the surface of the cell of the CNS.

A further aspect of the present invention relates to a composition for targeted delivery of an effector agent to a cell, wherein the composition comprises at least one rabies virus glycoprotein (RVG) peptide comprising SEQ ID NO:13 or a variant, fragment or derivative thereof, and at least one carrier particle attached thereto, wherein the effector agent is associated with the carrier particle.

In some embodiments, carrier particle comprises a cell permeable agent, for example a cell permeable peptide. In some embodiments, the cell permeable peptide is a polymeric arginine residue of various lengths, such as 11 residues (termed "11dR" or "11R" herein) or 9 residues (termed "9R" herein), or 7 or 5 residues in length, as disclosed herein.

In some embodiments the carrier particle comprises a liposome, polyarginine, protamine, or a cyclodextrin-based nanoparticle.

In some embodiments, the effector agent is delivered to a cell, for example a cell is located inside the blood brain barrier, for example a central nervous system cell. Examples of central nervous system cells include, for example but not limited to neuron, neuronal cell, brain cells, glial, astrocyte or neuronal supporting cells. In some embodiments, the cell comprises acetyl choline receptor (AchR) or a homologue or fragment thereof, for example the cell comprises the $\alpha$ subunit of AchR or a fragment or homologue thereof. In some embodiments, the cell comprises the $\alpha 1$ and/or $\alpha 7$ subunit of AchR or a fragment or homologue thereof.

In some embodiments, the cell is present within a subject, for example a mammalian subject, for example a human subject. In alternative embodiments, the cell is ex vivo, and in further embodiments, the cell is in a biological sample, for example in vitro.

In some embodiments, an effector agent is a nucleic acid or a nucleic acid analogue, for example but not limited to a DNA or RNA, for example siRNA, mRNA, tRNA, miRNA, strand template RNA (stRNA), shRNA, or analogues or combinations thereof. In some embodiments, an effector agent is a nucleic acid analogue, for example but not limited to antisense nucleic acids, oligonucleic acids or oligonucleotides, peptide nucleic acid (PNA), pseudo-complementary PNA (pcPNA), locked nucleic acid (LNA) or derivatives or analogues thereof. In some embodiments, the effector is a miRNA mimetic and in alternative embodiments, the effector is an antigomir, an oligonucleotide for silencing and/or inhibiting endogenous miRNA.

In alternative embodiments, the effector agent is a small molecule, and in alternative embodiments the effector agent is a protein or peptide, or the effector agent is a peptidomimetic, aptamer, antibody or protein or variant thereof. In some embodiments, the effector agent is an avimer, which is a peptide having multi-target site recognition capability.

In further embodiments, the effector agent is a therapeutic agent and/or diagnostic agent and/or an imaging agent.

In some embodiments, the carrier particle further comprises an additional targeting agent, wherein the targeting agent is a blood brain barrier targeting agent. Examples of such blood-barrier targeting agents include, for example but are not limited to, insulin, transferrin, insulin like growth factor (IGF), leptin, low density lipoprotein (LDL) and fragments or peptidomimetics or derivatives thereof. In some embodiments, additional targeting agents can be avimers for targeting receptors on the surface cells of the BBB, for example for targeting receptors for insulin, transferrin, insulin like growth factor (IGF), leptin, low density lipoprotein (LDL).

In some embodiments, the composition comprises an effector agent associated to a carrier particle, where the carrier particle is conjugated to a targeting agent (for example an RVG peptide). The composition is useful to deliver effector agents across the blood brain barrier in a subject. In some embodiments, the composition can further comprise a pharmaceutically acceptable carrier.

In further embodiments, the composition as disclosed herein is useful as a medicant for central nervous system disorders.

In some embodiments, administration of such a composition can be by any suitable route, for example but not limited to subcutaneous, intravenous, intracranial, or oral administration. In further embodiments, administration is, for example but not limited to, parenteral, intranasal, intracranial or intravenous.

Another aspect of the present invention relates to a method for delivering an effector agent to a cell expressing the alpha subunit of the acetylcholine receptor, the method comprising contacting the cell with an RVG peptide comprising SEQ ID NO:13 or a variant, fragment or derivative thereof, wherein the RVG peptide is attached to a carrier particle, wherein the effector agent is associated with the carrier particle. In some embodiments, the cells are in vitro, and in some embodiments the cells are in vivo or ex vivo.

Another aspect of the present invention relates to a method for delivering an agent across the blood-brain barrier of a subject, the method comprising administering to the subject a composition comprising a targeting agent, wherein the targeting agent is attached to a carrier particle, and wherein the agent is associated with the carrier particle. In some embodiments, the targeting agent is an RVG peptide of SEQ ID NO:13 or a variant, fragment or derivative thereof, and in alternative embodiments, the targeting agent is, for example but not limited to, insulin, transferrin, insulin like growth factor (IGF), leptin, low density lipoprotein (LDL) and fragments or peptidomimetics or derivatives thereof.

The present invention provides a method for delivery of an agent to the central nervous system (CNS) of a host. The method comprises administering to the host an agent, wherein the agent comprises an RVG peptide comprising SEQ ID NO:13 13 or a variant, fragment or derivative thereof, wherein the RVG peptide is attached to a carrier particle and a therapeutic agent is associated with the carrier particle.

The invention further provides a targeted delivery composition comprising an RVG peptide, wherein the RVG peptide is attached to a carrier particle. The invention still further provides the targeted delivery composition wherein an effector agent is a therapeutic agent, which is associated with the carrier particle.

In one embodiment, the carrier particle is a lyposomal or polymeric nanoparticle, for example a liposome, a polyarginine peptide, a protamine or a cyclodextrin-based nanoparticle.

In one embodiment, the effector agent or therapeutic agent is a nucleic acid, e.g., siRNA, shRNA, stRNA, miRNA or DNA or nucleic acid analogues, antigomers or derivatives thereof. In another embodiment, the therapeutic agent is a small molecule. In yet another embodiment, the therapeutic agent is a protein, e.g., an enzyme, an antibody, peptidiomimetic, aptamer, avimer and derivatives thereof.

In one embodiment, the carrier particle further comprises a blood brain barrier targeting agent in addition to the RVG peptide.

In one embodiment, the agent is further administered with a pharmaceutically acceptable carrier. In one embodiment, the administration is parenteral, intranasal, intracranial or intraocular.

The invention further provides a method for targeted delivery of an agent to a cell expressing the alpha subunit of the acetylcholine receptor. The method comprises administering the agent to the cell. The agent comprises an RVG peptide comprising SEQ ID NO: 13 or a fragment, derivative or variant thereof, wherein the RVG peptide is attached to a carrier particle, wherein a therapeutic agent is associated with the carrier particle. In one embodiment, the cell is in vitro.

BRIEF DESCRIPTION OF THE DRAWINGS

FIG. 1 shows the pLL3.7 lentiviral vector.

FIG. 2 shows efficient transduction and intracellular processing of shRNA. BHK 21 cells were transduced with lentiviruses and analyzed by flow cytometry for GFP expression (left) and tested for endogenous $FvE^J$ specific siRNA production by Northern blotting (right).

FIG. 3 shows $FvE^J$ shRNA inhibits JEV replication. Transduced BHK 21 cells were infected with Japanese Encephalitis virus (JEV) and viral replication analyzed by flow cytometry 2 days later using a JEV-specific antibody.

FIG. 4 shows degradation of viral RNA by $FvE^J$ shRNA. RNA from transduced and infected cells was probed with a JEV cDNA probe.

FIG. 5 shows $FvE^J$ shRNA protects against JEV. Mock, control Luc or $FvE^J$ shRNA injected mice were challenged with JEV and observed for mortality.

FIG. 6 shows absence of brain pathology in $FvE^J$ shRNA-treated mice. Mice injected with Luc shRNA (left) or $FvE^J$ shRNA (right) were infected with JEV for 5 days and the brain sections examined for histopathology. Shown are low magnification (×20) (top panels) and high magnification (×400) (bottom panels).

FIGS. 7A-7B show the absence of virus in FvEJ shRNA-treated mice. Mice were treated as in FIG. 5. Panel 7A shows FACs analysis of brain cells administered with Luc-siRNA or FvE-siRNA. Panel 7B shows brain homogenates from animals administered with Luc-siRNA, or FvE-siRNA and titered for viral titre of JEV.

FIGS. 8A-8B show si$FvE^J$ siRNA can protect against JE in vitro as well as in vivo. FIG. 8A shows neuro 2A cells transfected with siLuc (grey filled) or with si$FvE^J$ siRNA in lipofectamine (broken line) or complexed with JetSI/dope (solid line) were infected with JEV for 2 days before staining FIG. 8B shows mice (5/group) were infected with JEV and treated with control or si$FvE^J$ siRNA after 30 min or 6 h after infection.

FIGS. 9A-9B show siFvE siRNA protects against both Japanese Encephalitis virus (JEV) and West Nile Virus (WNV) in vitro and in vivo. FIG. 9A shows neuro 2A cells treated with siLuc or si$FvE^{JW}$ siRNA complexed with JetSI/dope were infected with JEV or WNV for 2 days before staining FIG. 9B shows mice (10/group) were infected with JEV (left) or WNV (right) and treated with control siLuc or si$FvE^{JW}$ siRNA after 30 min or 6 h after infection and followed for survival over time.

FIG. 10 shows RVG pseudotyping allows neuronal cell specific targeting. HeLa or BHK-21 or Neuro 2a cells were infected with PLL3.7 lentiviruses pseudotyped with either VSV-G or RVG and examined for GFP fluorescence 2 days later.

FIG. 11 shows RVG pseudotyping enhances shRNA effectiveness. Mice were injected with indicated doses of lentiviruses psuedotyped with either VSV-G or RVG, challenged with JEV and observed for mortality.

FIG. 12 shoes RVG peptide specifically binds neuronal cells. Neuro 2a and HeLa cells were sequentially incubated with RVG-Bio or Scrambled RVG-Bio and SAPE and examined by flow cytometry.

FIG. 13 shows α-bungarotoxin inhibits RVG peptide binding. RVG peptide binding. Neuro 2a cells were stained with RVG-Bio peptide in the presence or absence of a-bungarotoxin then tested for RVG peptide (10-7 M) binding.

FIG. 14 shows RVG peptide binds mouse brain cells. Freshly isolated brain and spleen cells were stained with RVG-Bio and SAPE.

FIG. 15 shows intravenously injected RVG peptide binds brain cells. Mice were given a control peptide or RVG-Bio intravenously and 2 h later, brain cells stained with SAPE.

FIG. 16 shows RVG-TAT peptide can deliver DNA vector to neuronal cells. Neuro 2a or BHK-21 cells were transduced with pLL3.7 DNA bound to RVG-TAT and examined for GFP expression 2 days later.

FIG. 17 shows RVG-11dR peptide delivers both DNA and siRNA. Neuro 2a cells were transduced with pLL3.7 DNA vector (left) or FITC labeled siRNA (right) bound to RVG-11dR and examined for GFP or FITC fluorescence 2 days later.

Figure 20B:
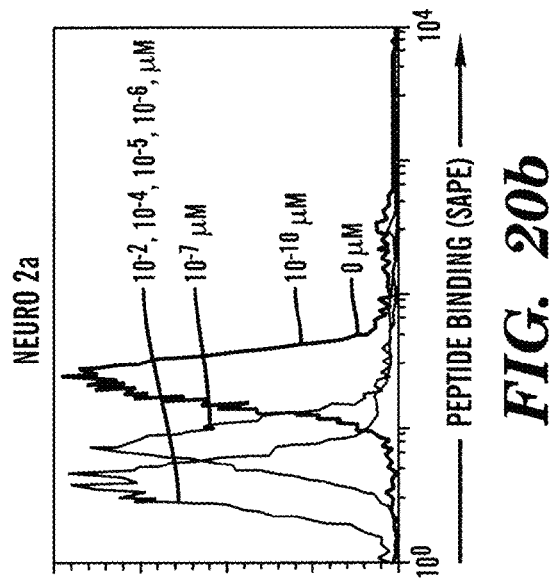
Figure 20A:
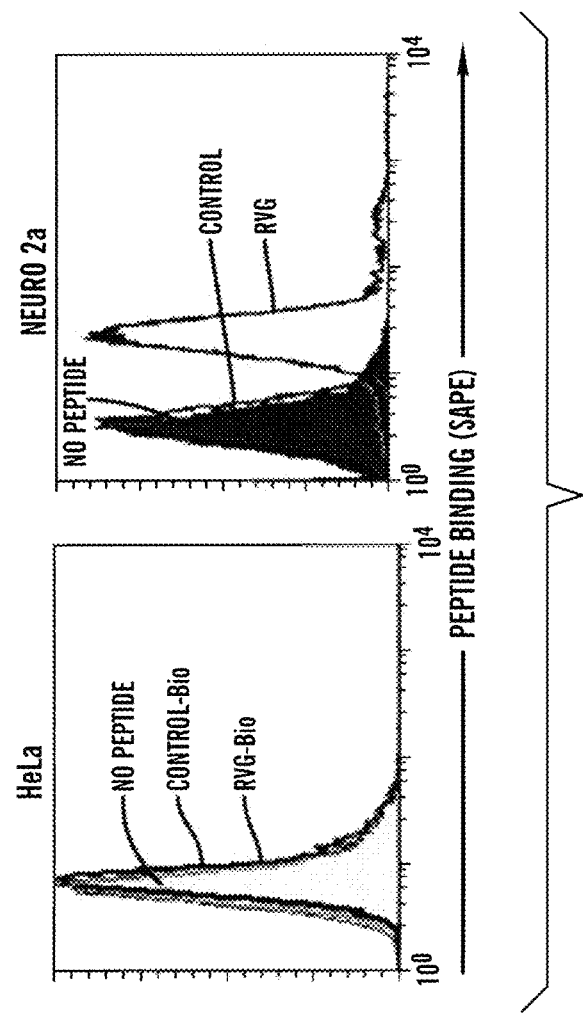

FIGS. 20A-20B show RVG binds specifically to the neuronal cell line, Neuro 2a and the binding is inhibited by α-bungarotoxin. FIG. 20A shows HeLa and Neuro 2a cells incubated with biotinylated RVG peptide and examined for peptide binding by staining with streptavidin-PE (SAPE). Control peptide did not bind to either cell type while RVG binding was detected exclusively on Neuro 2a cells. FIG. 20B shows RVG binding to Neuro 2a cells was measured in the presence of indicated concentrations of α-bungarotoxin. RVG peptide was used at 2 µM.

Figure 21:
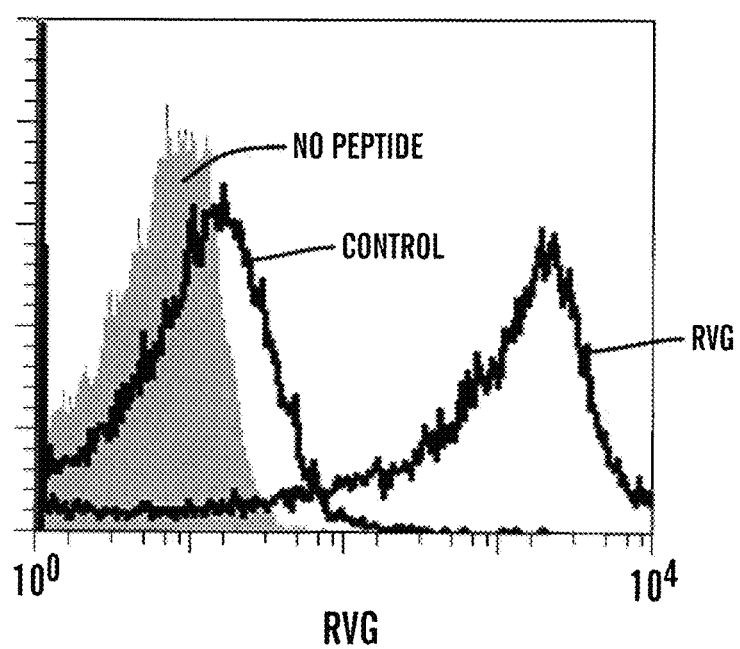

FIG. 21 shows RVG can be detected in the mouse brain after intravenous injection. Mice were injected i.v. with 100 µg of biotinylated RVG or the control peptide and 2 h later, single cell suspensions of brain examined by flow cytometry after internal staining with SAPE.

Figure 22B:
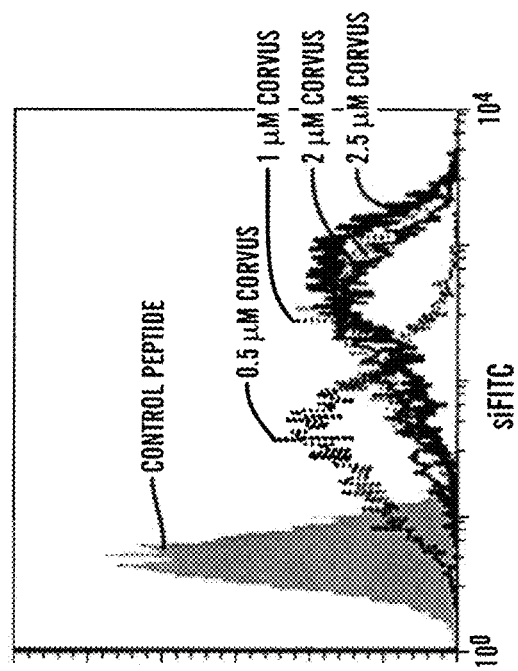
Figure 22A:
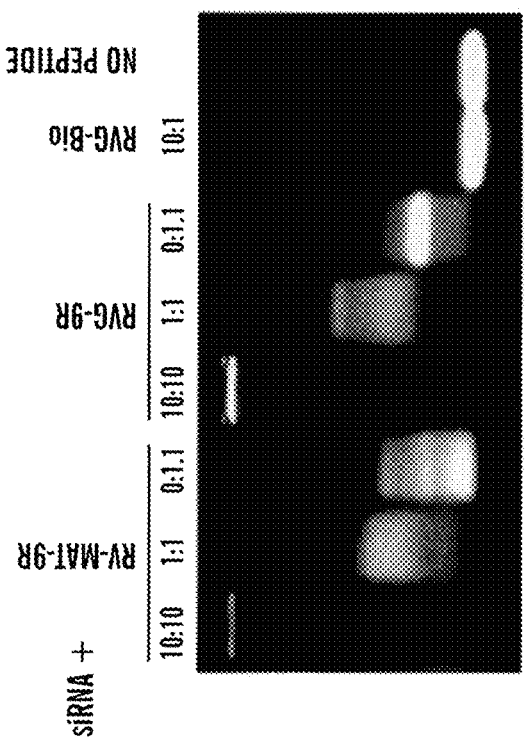

FIGS. 22A-22B shows CORVUS (a chimeric peptide comprising an RVG peptide fused to a cell penetrating peptide) binds and delivers siRNA into neuronal cells. FIG. 22A shows 100 pmole of siRNA was complexed with CORVUS or control peptide at the indicated molar ratios and binding of siRNA was assessed by gel mobility retardation on 2% agarose gels. FIG. 22B shows peptides incubated with 100 pmoles FITC-labeled siRNA at the indicated concentrations for 10 min and then added to Neuro 2a cells in culture. siRNA uptake was assessed 16h later. Control peptide was used at 25 µM. A 10:1 molar ratio of peptide to siRNA was deemed optimal.

Figure 23B:
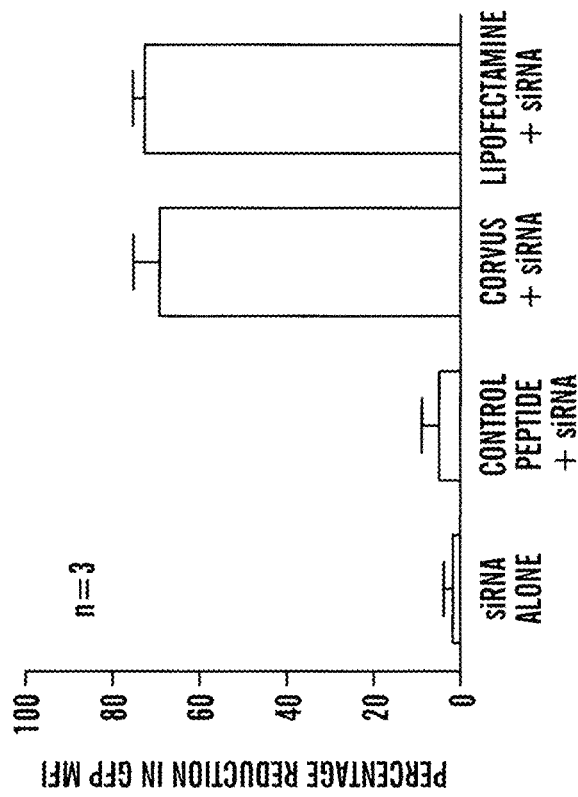
Figure 23A:
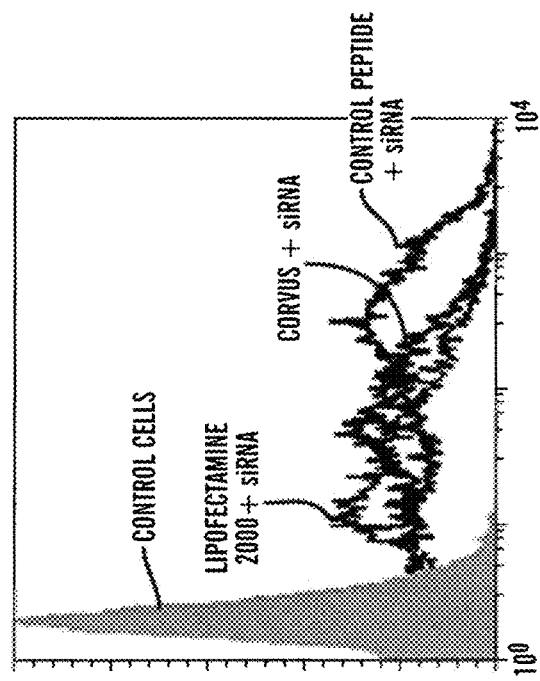

FIGS. 23A-23B show CORVUS delivered siRNA is functional. Peptides were mixed with 200 pmole of anti-GFP siRNA at a 10:1 molar ratio and added to Neuro 2a cells stably expressing GFP. FIG. 23A shows GFP expression levels were monitored 60 h later. FIG. 23B shows CORVUS was found to be as efficient as Lipofectamine 2000TM in silencing GFP expression.

Figures 24A, 24B, 24C, 24D, 24E:
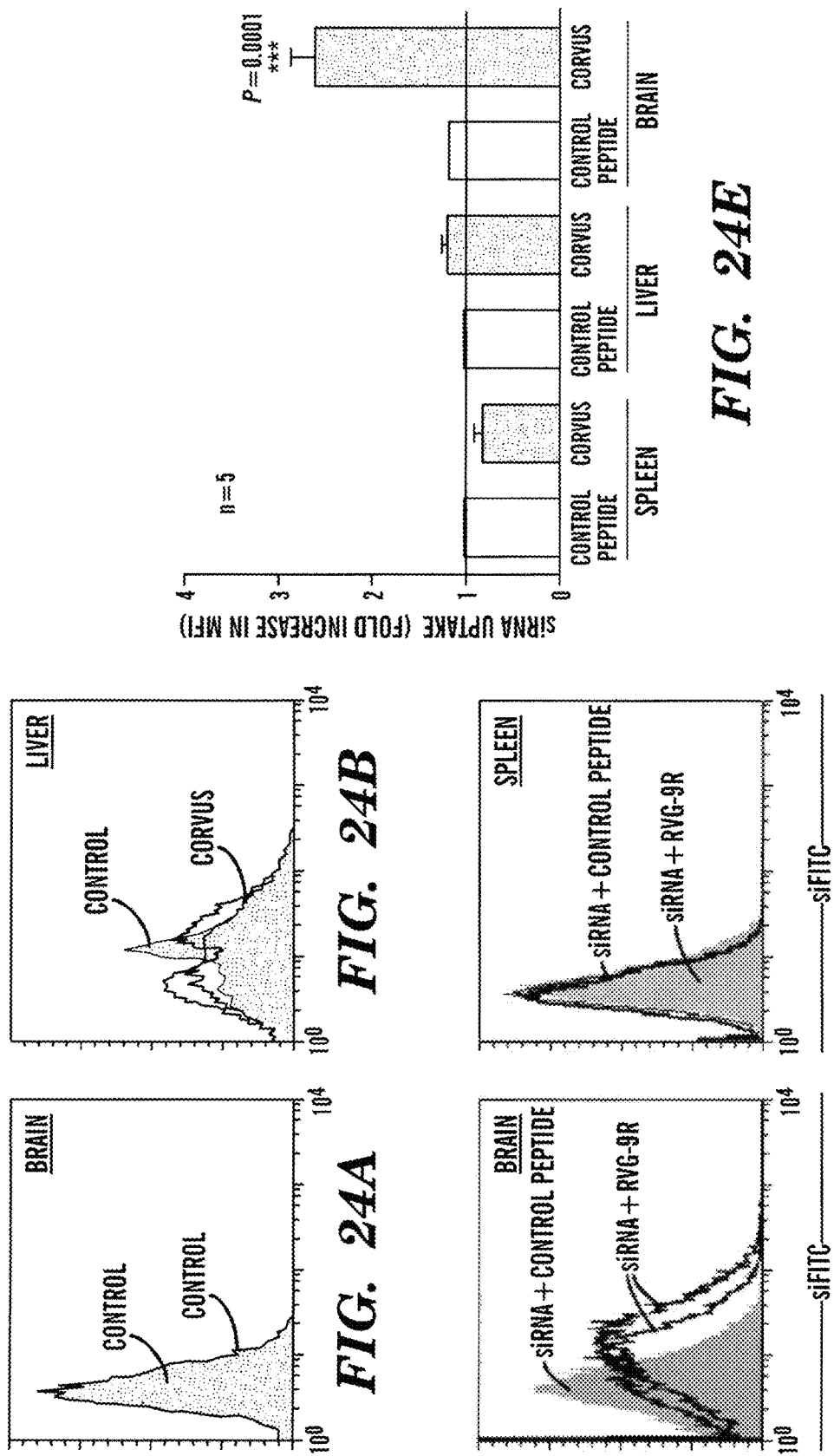

FIGS. 24A-24E show CORVUS (RVG-9R) can deliver siRNA to brain cells after i.v. injection in mice. Mice were injected twice, 6 h apart, intravenously in the tail vein with 50 µg of FITC-labeled siRNA complexed to peptides at a 10:1 molar ratio. FIG. 24A-E shows organs were harvested 16 h after the last injection and single cell suspensions analyzed for the presence of siRNA FITC. FIG. 24A shows control brain samples, Fog 24B shows liver with CORVUS or control peptide, FIG. 24C shows brain from CORVUS and control treated samples, and FIG. 24D shows spleen with CORVUS or control peptide. FIG. 24E shows siRNA was detected specifically in the brain tissue of mice treated with CORVUS. Control peptide did not induce any uptake of siRNA.

FIGS. 25A-25B show transvascular delivery of GFP siRNA complexed to CORVUS specifically knocks down GFP expression in GFP-Tg mice. Mice transgenic for GFP were intravenously administered 50 µg anti-GFP siRNA complexed to either CORVUS or control peptides 3 times at 16 h intervals. FIG. 25A shows organs harvested 60 h after the last treatment and single cell suspensions analyzed for GFP expression levels. FIG. 25B shows filled histograms represent FACS plots with wild-type mice.

Figure 26C:
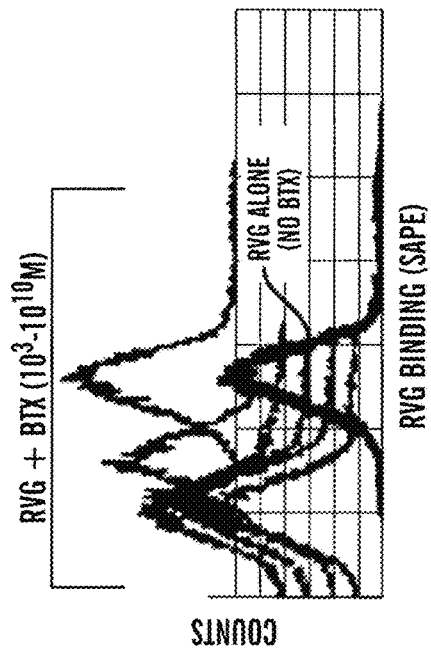
Figure 26B:
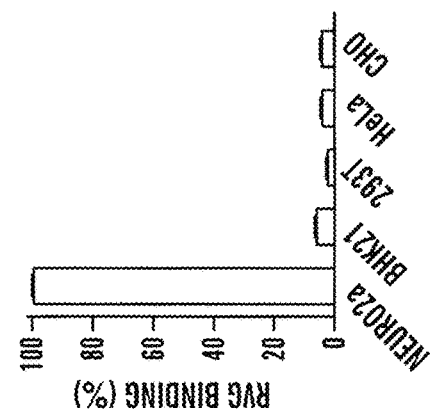
Figure 26A:
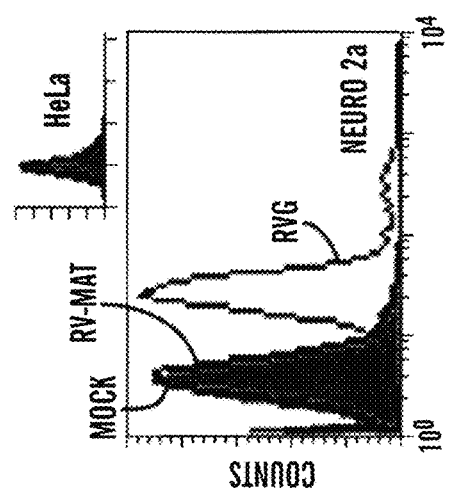
Figure 26D:
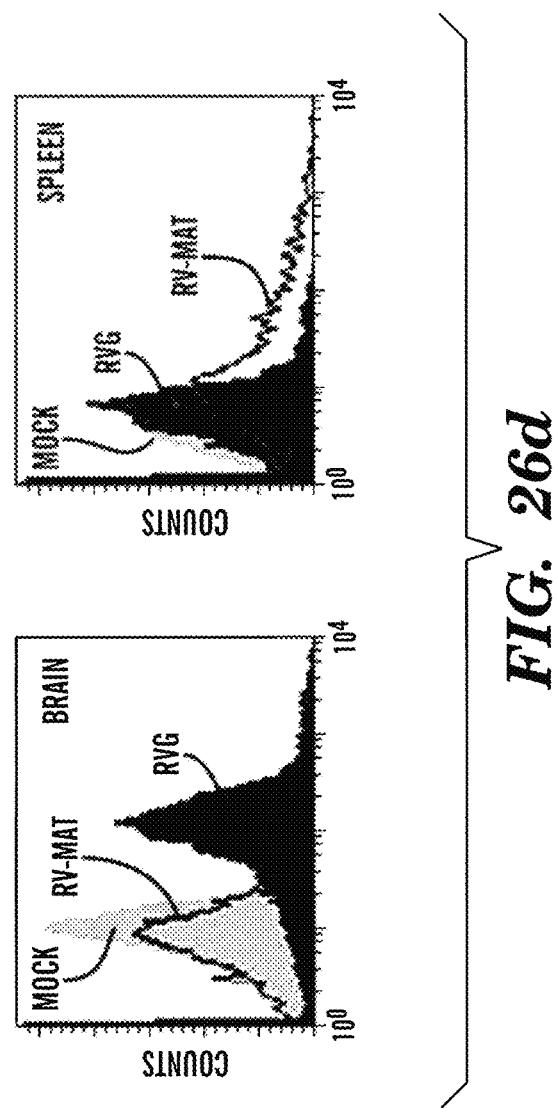
Figure 26E:
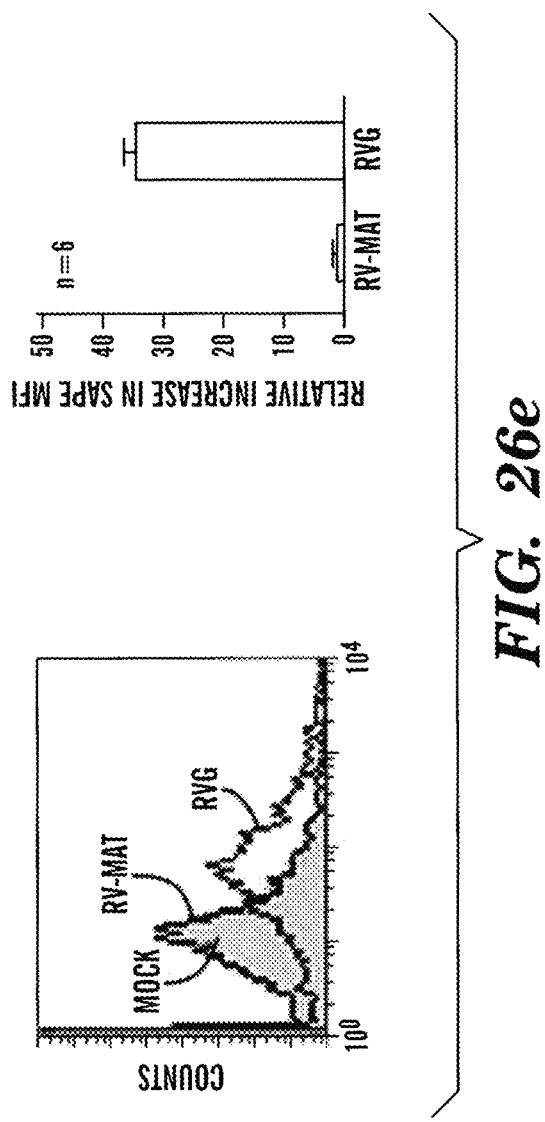

FIGS. 26A-26E show a short RVG peptide binds to neuronal cells in vitro and in vivo. FIG. 26A shows Neuro 2a and HeLa cells (inset) were incubated with biotinylated RVG or RV-MAT peptides, stained with SAPE and examined by flow cytometry. FIG. 26B shows Peptide binding was also tested using indicated cell lines. RVMAT did not bind any of the cell lines (not shown). FIG. 26C shows Neuro 2a cells were stained with biotinylated RVG in the absence (red histogram) or presence of decreasing concentrations of BTX (grey histograms). FIG. 26D shows freshly isolated mouse brain and spleen cells were tested for peptide binding. FIG. 26E shows mice were injected iv with biotinylated RVG or RV-MAT peptide and 4 h later, isolated brain cells stained with SAPE.

Figure 27B:
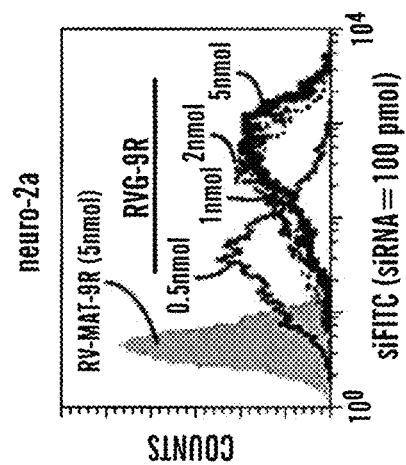
Figure 27A:
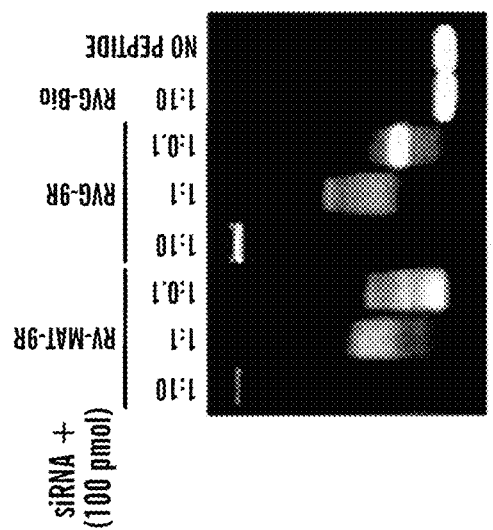
Figures 27C, 27D:
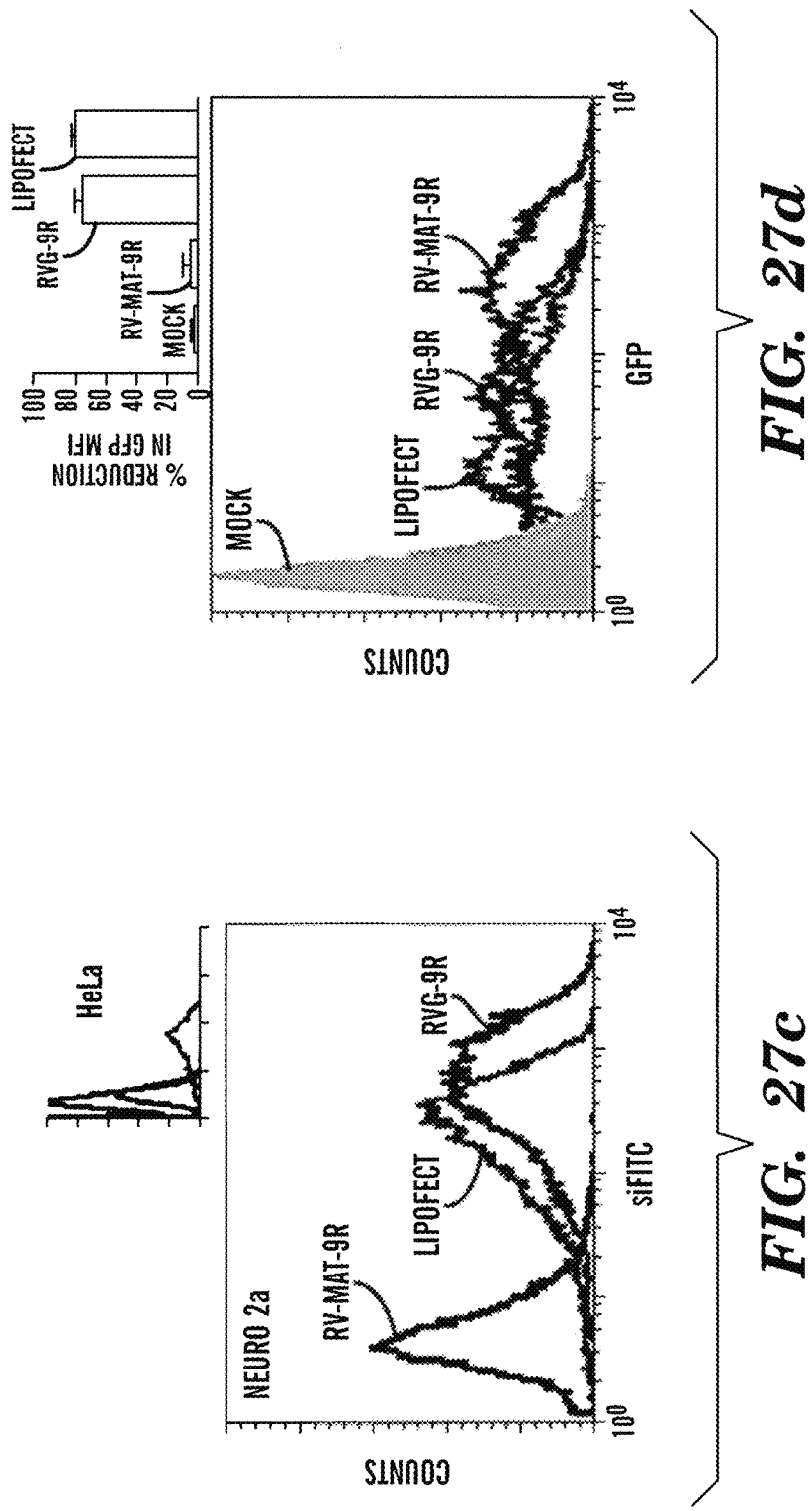

FIGS. 27A-27D show an RVG-9R peptide binds and delivers siRNA to neuronal cells in vitro resulting in gene silencing. FIG. 27A shows mobility of free or peptide-complexed siRNA was analyzed by agarose gel electrophoresis. FIG. 27B shows Neuro 2a cells were examined for uptake of FITC-siRNA complexed with RVG-9R at the indicated concentrations. FIG. 27C shows Neuro 2a and HeLa (inset) cells were examined for uptake of FITC-siRNA complexed with RVG-9R or RV-MAT-9R peptides at 1:10 molar ratio. Lipofectamine transfection was used as positive control. FIG. 27D shows Neuro 2a cells stably expressing GFP were transduced with GFP siRNA complexed to RVG-9R or RV-MAT-9R peptides and GFP silencing tested 2 days later. A representative histogram and cumulative data from 3 independent experiments (inset) are shown.

FIGS. 28A-28B show RVG-9R enables transvascular delivery of siRNA to the CNS. FIG. 28A shows mice were injected iv with FITC-siRNA/peptide complexes and uptake by brain, spleen and liver cells examined by flow cytometry. Representative histograms (top) and cumulative data (bottom) are shown. FIG. 28B shows coronal sections of brain from FITC-siRNA/RVG-9R injected mice (n=6) were stained with anti-FITC antibody and examined by fluorescent microscopy. Images of FITC-positive cells in the cortex, striatum and thalamus at lower (left panel) and higher magnification of boxed regions (middle panel) are shown. Right panel shows images from control Ig stained brain sections at the higher magnification. Scale bar=200 µm.

Figure 29A:
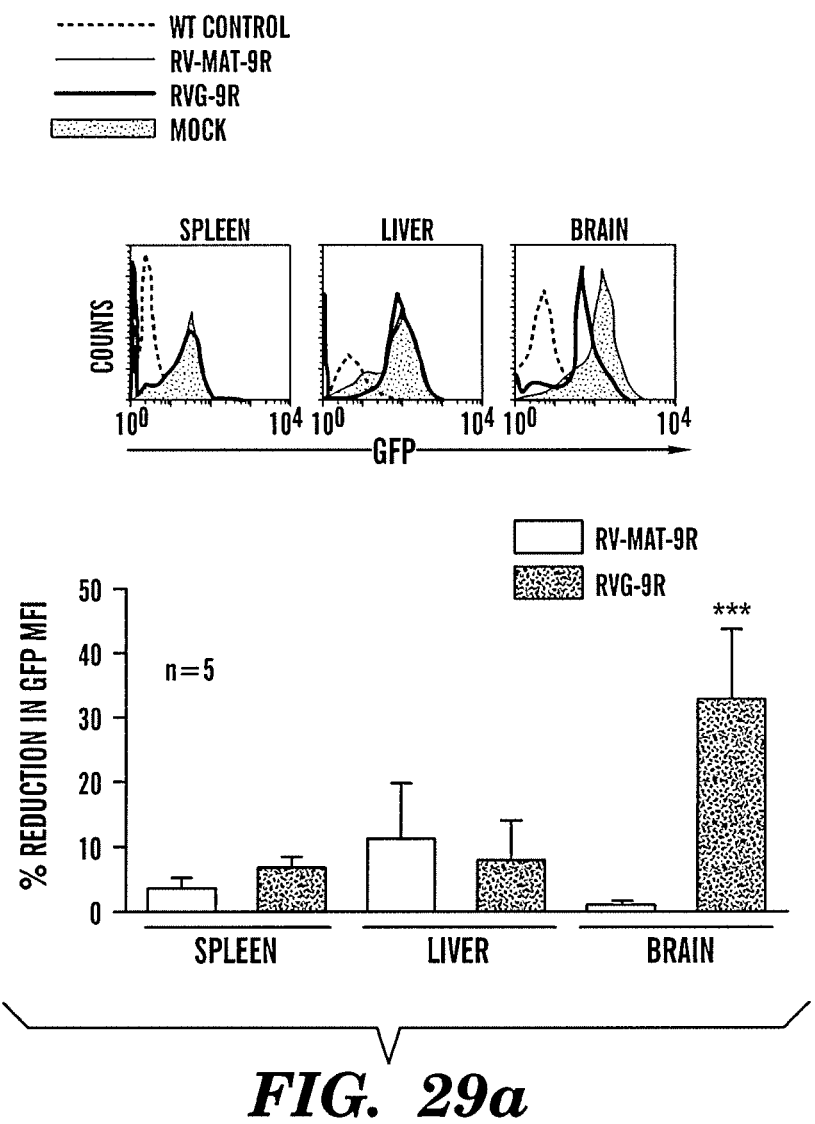
Figure 29B:
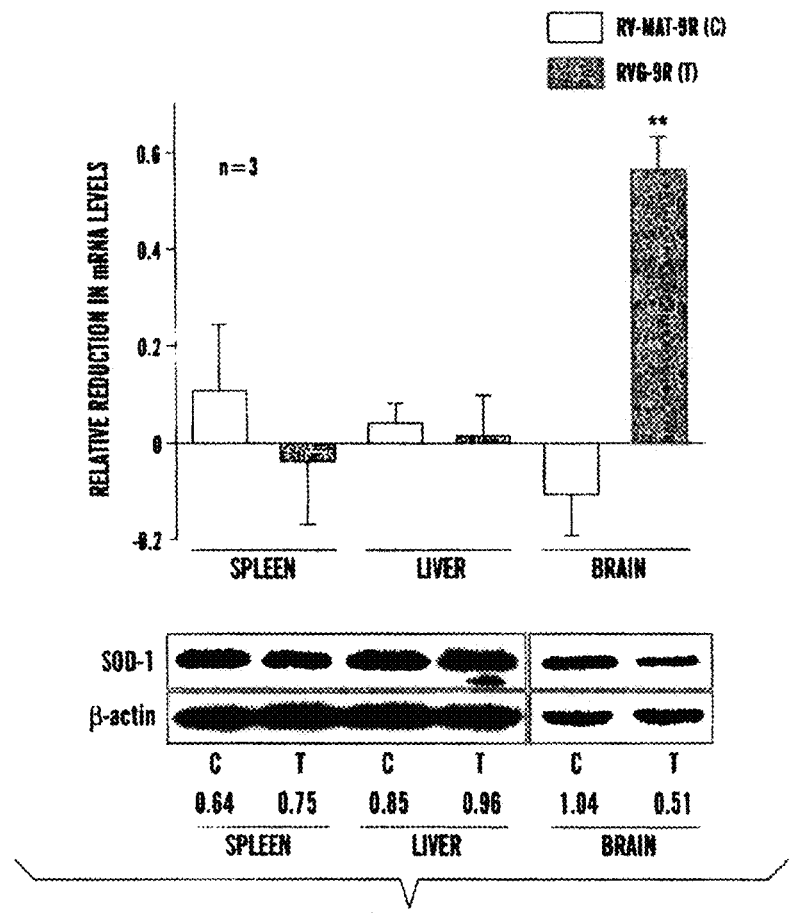
Figure 29C:
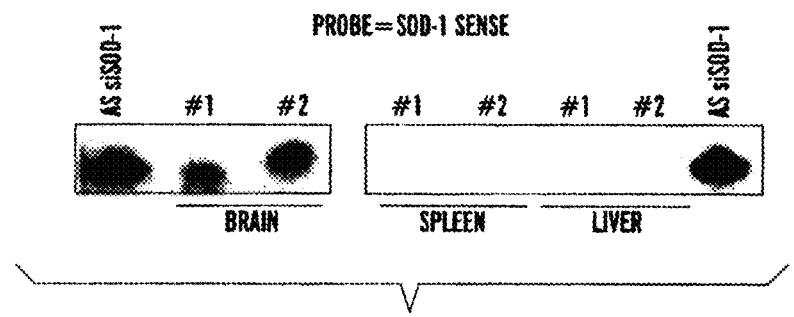
Figure 29D:
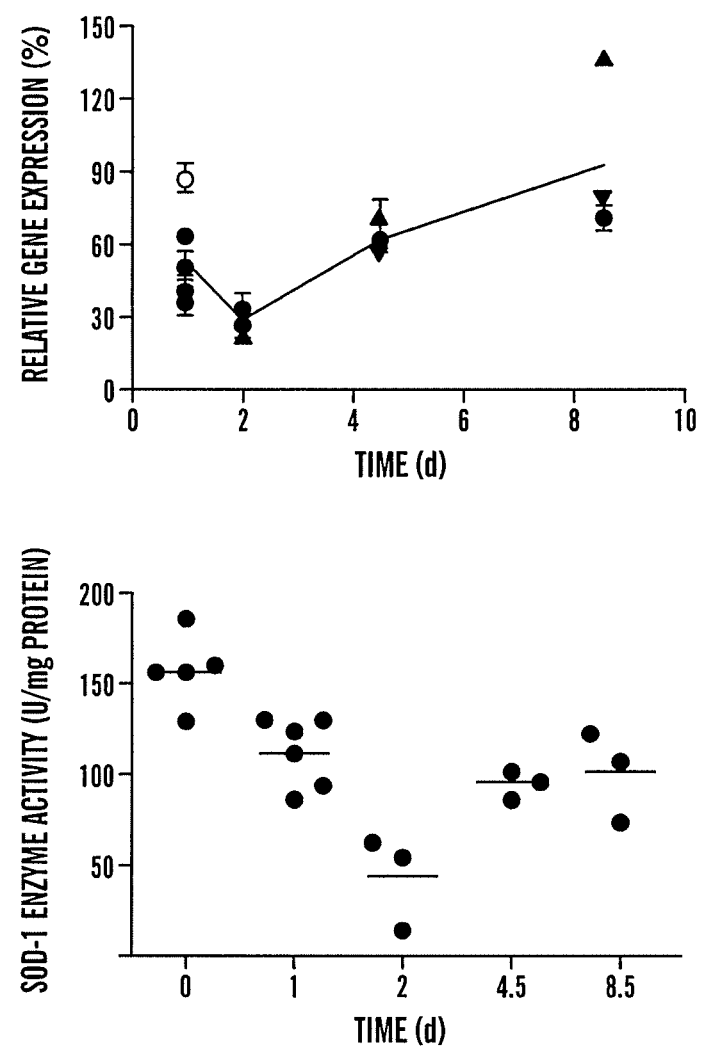

FIGS. 29A-29D show brain-specific gene silencing by iv injection of RVG-9R/siRNA complex. FIG. 29A shows GFP Tg mice were iv injected with GFP siRNA/peptide complexes and their brain, spleen and liver cells analyzed for GFP expression. Representative histograms (top) and cumulative data (bottom) are shown. Dotted lines in the histograms represent cells from wild type mice. FIG. 29B shows Balb/c mice iv injected with SOD1 siRNA/peptide complexes and their brain, spleen and livers examined for SOD1 mRNA (top) and protein levels (bottom). The numbers below the western blot represent the ratios of band intensities of SOD-1 normalized to that of β-actin. FIG. 29C shows small RNAs isolated from different organs of RVG-9R/SOD1 siRNA injected mice were probed with siRNA sense strand oligo. Antisense strand oligo was used as positive control (first and last lanes). FIG. 29D shows mice iv injected with SOD siRNA bound to RVG-9R and the duration of gene silencing determined by quantitation of SOD1 mRNA levels (top) and SOD1 protein enzyme activity (bottom) on indicated days after siRNA administration.

Figure 30A:
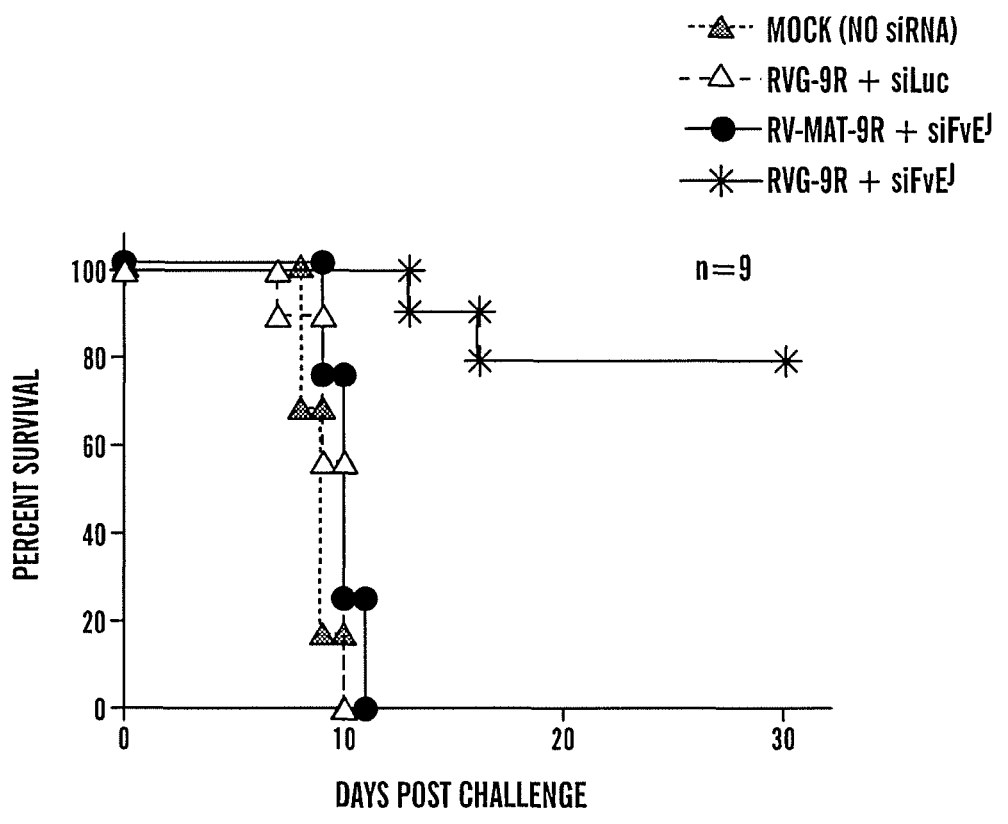
Figure 30B:
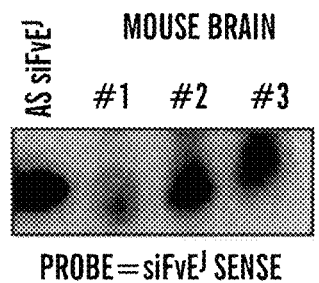
Figure 30C:
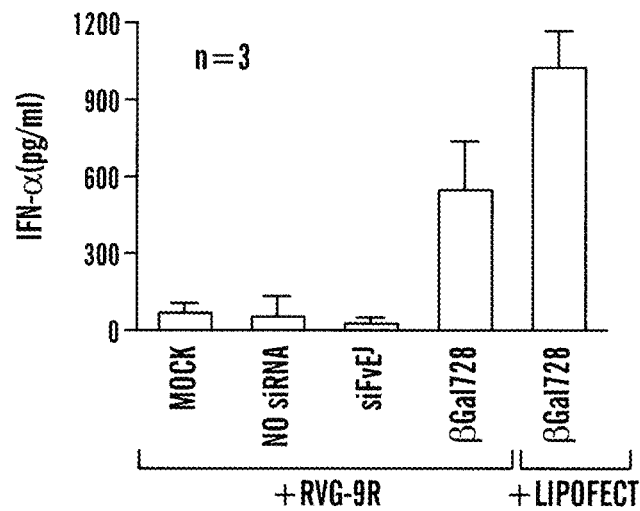

FIGS. 30A-30C show iv treatment with antiviral siRNA/RVG-9R complex protects mice against JEV encephalitis. FIG. 30A shows JEV-infected mice were treated iv with siLuc or siFvEJ complexed to either RVG-9R or RVMAT-9R daily for 4 days and monitored for survival. FIG. 30B shows RNA isolated from the brains of RVG-9R/siFvEJ treated mice were examined for the presence of siRNA antisense strand by Northern blotting. Antisense strand of siFvEJ served as positive control. FIG. 30C shows Balb/c mice were injected iv with siFvEJ bound to RVG-9R peptide and 7 h later, their serum samples tested for IFN levels by ELISA. The immunostimulatory βgal 728 siRNA complexed with RVG-9R or lipofectamine was used as positive control.

Figure 31:
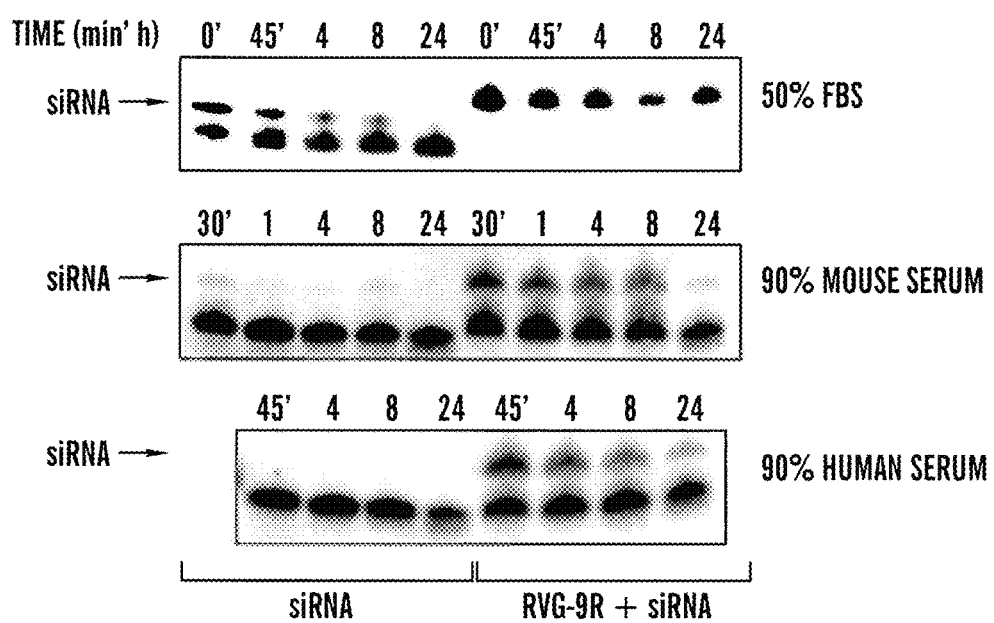

FIG. 31 shows RVG-9R binding confers partial protection from serum nucleases. Naked and RVG-9R-complexed siRNA were incubated with sera at 37° C. and aliquots taken at indicated times digested with proteinase K, electrophoresed on 15% polyacrylamide gels and visualized with SYBR gold staining. The position of intact siRNA is indicated.

Figure 32A:
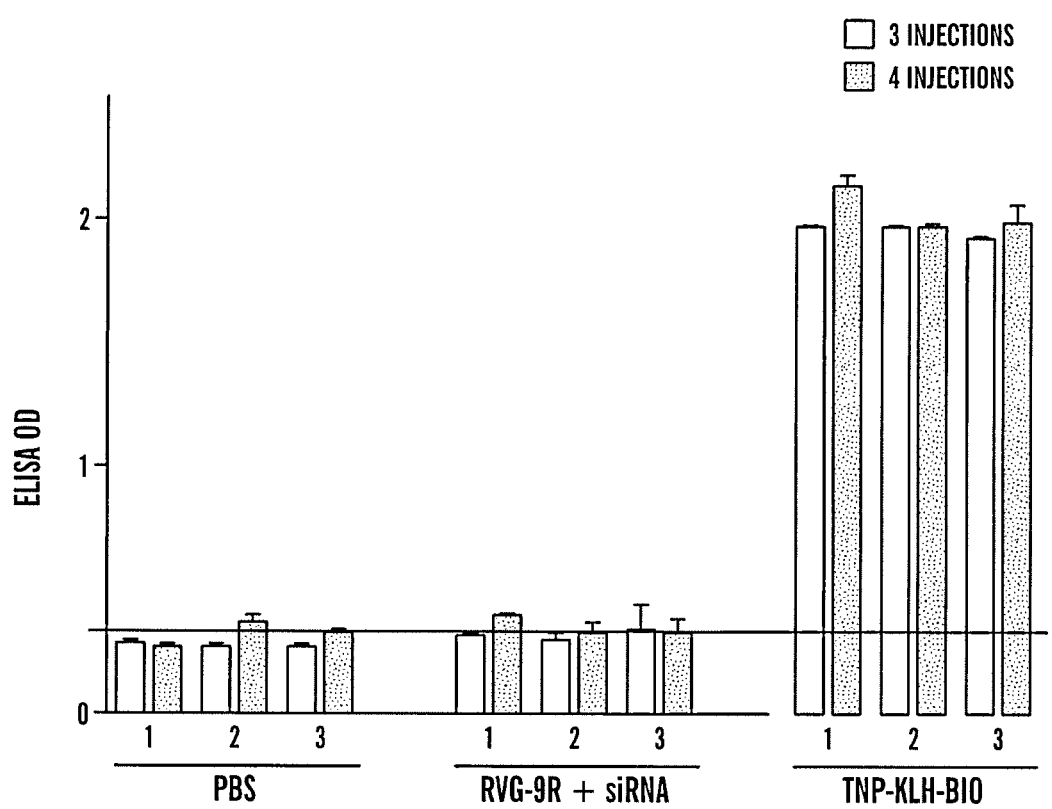
Figure 32B:
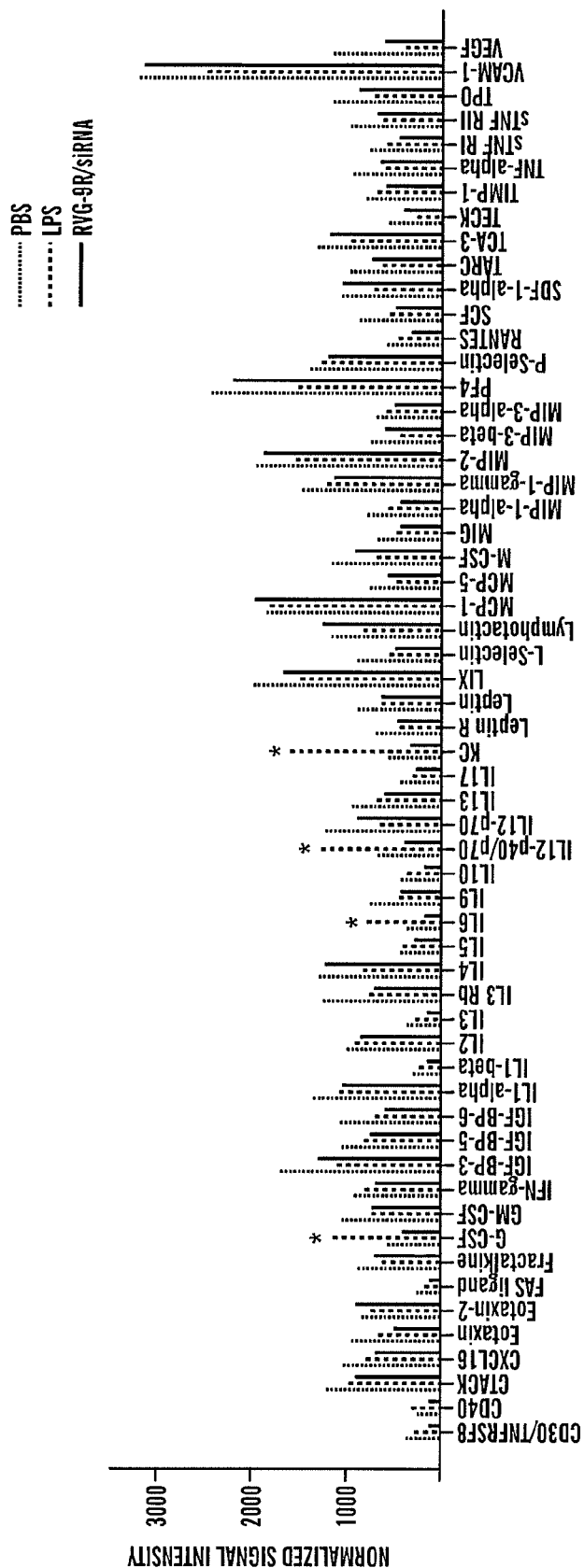

FIGS. 32A-32B shows an RVG-9R siRNA complex does not induce antibodies or inflammatory cytokines. FIG. 32A shows mice injected with siRNA complexed to RVG-9R or for positive control, with the immunogenic TNP-KLH-biotin peptide on days 0, 3, 10 and 22 and serum samples collected on days 21 and 30 tested for the presence of antibodies to RVG or biotin by ELISA. FIG. 32B shows sera obtained 1 day after the 4th RVG-9R/siRNA injection were tested for the indicated panel of secreted cytokines and chemokines in an ELISA assay. Sera from LPS injected mice served as positive control. Asterisks indicate statistically significant differences.

DETAILED DESCRIPTION OF THE INVENTION

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages can mean±1%.

A major bottleneck in harnessing the potential of RNAi for clinical use is the lack of suitable delivery methods. Delivery is particularly difficult in the CNS and the methods used for systemic delivery such as intravenous hydrodynamic injection [42,43] and intravenous (IV or iv) injection of siRNA or shRNA vectors complexed with lipofectamine or polyethyleneimine [44] are unlikely to work for delivery to the CNS because of the presence of BBB. Thus, the only available method for CNS delivery at present is local sterotaxic injection of nonreplicating viral vectors and siRNA [61]. One problem with these approaches is the extremely limited spread, confining delivery to a small area at the site of injection. Thus, delivery methods to ensure a more extensive spread of the delivered si/shRNAs for its efficacy in situations like tumors and intracranial infections are needed. The inventors have discovered a peptide derived from Rabies virus glycoprotein (RVG) can specifically target neuronal cells. This peptide has previously been shown to competitively inhibit α-bungarotoxin binding to the nicotinic acetylcholine receptor α7 subunit [94, 95, 102]. Acetylcholine receptor α7 subunit is widely expressed by many cell types in the brain including the neurons, astrocytes and glia cells and it is also expressed by the brain capillary endothelial cells [98].

Accordingly, in one embodiment the present invention provides methods to deliver agents to the brain or spinal cord, wherein at least one agent is associated to RVG peptide as disclosed herein. In some embodiments, the RVG peptide is associated with a carrier particle, for example a lyposomal or polymeric nanoparticles, such as a liposome, and the agent is associated with the carrier particle. In some embodiments, the carrier particle is a cell permeable agent. In further embodiments, the cell permeable agent is a cell permeable peptide, for example polymeric arginine residues of various lengths such as 11dR or 9R as disclosed herein, or TAT. In further embodiments the RVG peptide is conjugated to other targeting agents, or the carrier particle is conjugated to additional targeting genes.

The inventors have discovered that the RVG peptide results in extensive spread of agents in the central nervous system, thus results in delivery of an agent to sites distal to the site of administration, for example distal to the site of intracranial or intraparemchal injection. Moreover, in one embodiment, the RVG peptide facilitates the crossing of an agent across the BBB. In some embodiments, the RVG peptide is conjugated, for example fused to a cell penetrating peptide (such as for example but not limited to, HIV-TAT, or polymeric arginine residues of various lengths such as 9R or 11dR as disclosed herein) or combined with a brain endothelial cell transporter (such as transferrin or transferrin receptor antibody), and thus, facilitates brain delivery by a noninvasive intravenous approach. In some embodiments, the effector agents are therapeutic agents. Therapeutic agents for which are, for example nucleic acids such as siRNA, miRNA and shRNAs effector agents can be expressed via vectors offer the advantage of long term expression which can be desirable in some situations like in the treatment of neurological disorders, neurodegenerative diseases and cancer. Synthetic siRNAs offer a drug-like approach for transient gene silencing. Moreover, in the non-dividing cells of the CNS, the effect is prolonged, e.g., 3 weeks. Alternatively, the RVG delivery method can be used in conjunction with therapeutic agents that are not RNAi agents, such as but not limited to small molecules, peptides, antibodies, avimers, nucleic acid analogues, antigomers, miRNA mimetics or any other agent that is compatible with delivery by means of the carrier particles associated with an RVG peptide as disclosed herein.

As disclosed herein, the present invention is based, in part, on the discovery that peptides derived from the rabies virus glycoprotein are useful as targeting moieties to deliver agents to cells expressing the α subunit of the acetylcholine receptor or a homologue thereof and for example neuronal cells. In some embodiments, the neuronal cells are in a subject (i.e. in vivo), and in some embodiments the neuronal cells are ex vivo or are cultured neuronal cells, for example in vitro such as primary neuronal cultured cells. In some embodiments, the neuronal cells are neuronal precursor or neuronal progenitor cells, such as neuronal progenitor stem cells that express the α subunit of the acetylcholine receptor or a homologue thereof.

Accordingly, the present invention is also directed to a method and a composition for delivering therapeutic compositions to target cells. In particular, the invention is directed to a method and a composition for targeted delivery to target cells protected by the blood brain barrier (BBB). The method utilizes a composition comprising a peptide derived from the Rabies virus glycoprotein (RVG) that is capable of specifically binding to target cells, but not other cell types. The composition further comprises a carrier particle attached to an RVG peptide as disclosed herein. The carrier particle can be further associated with an effector agent, or a therapeutic composition. Thus, the invention is directed to targeted delivery to target cells by means of an RVG peptide.

Targeting Agents and Rabies Virus Glycoprotein (RVG) Peptide

The glycoprotein from the neurotropic Rabies virus shows a significant homology with the snake venom alpha neurotoxin that binds to the nicotinic acetylcholine receptor [91]. In fact, further studies showed that the acetylcholine receptor is also a Rabies virus receptor [92, 93]. Interestingly, an RVG peptide was also found to competitively inhibit α-bungarotoxin binding to the acetylcholine receptor [94, 95]. However, there has been no indication that the 29 mer RVG peptide (RVG) as disclosed herein facilitates targeted delivery to such cells expressing the acetylcholine receptor or that such a peptide can facilitate passage through the blood brain barrier.

Accordingly, in one embodiment the present invention provides a targeting agent to selectively targets cells expressing the α subunit of the acetylcholine receptor, thereby facilitating specific delivery to such target cells. In one embodiment of the present invention, a targeting agent comprises amino acid residues 173-202 of the RVG: YTIWMPENPRPGTPCDIFTNSRGKRASNG (SEQ ID NO: 13) or a variant or a derivative or fragment thereof. In further embodiments, the targeting agent is a fragment of SEQ ID NO:13. Such a fragment of SEQ ID NO:13 can be, for example, 1, 2, 3, 4, 5, 6, 7, 8, 9 or 10 amino acids deleted from the N-terminal and/or C-terminal of SEQ ID NO:13. Persons of ordinary skill in the art can easily identify the minimal peptide fragment of SEQ ID NO:13 by sequentially deleting N- and/or C-terminal amino acids from SEQ ID NO:13 and assessing the function of the resulting peptide fragment, such as function of the peptide fragment to bind acetylcholine receptor and/or ability to transmit through the blood brain barrier as disclosed herein. In some embodiments, a fragment of SEQ ID NO:13 is any 28, 27, 26, 25, 24, 23, 22, 21, 20, 19, 18, 17, 16 or 15 peptides of SEQ ID NO:13. In some embodiments, a fragment of SEQ ID NO:13 is less than 15 peptides in length.

The term "derivative" as used herein refers to peptides which have been chemically modified, for example but not limited to by techniques such as ubiquitination, labeling, pegylation (derivatization with polyethylene glycol) or addition of other molecules.

As used herein, "variant" with reference to a polynucleotide or polypeptide, refers to a polynucleotide or polypeptide that can vary in primary, secondary, or tertiary structure, as compared to a reference polynucleotide or polypeptide, respectively (e.g., as compared to a wild-type polynucleotide or polypeptide). A "variant" of a RGV peptide, for example SEQ ID NO:13 is meant to refer to a molecule substantially similar in structure and function, i.e. where the function is the ability to pass or transit through the BBB, to either the entire molecule, or to a fragment thereof. A molecule is said to be "substantially similar" to another molecule if both molecules have substantially similar structures or if both molecules possess a similar biological activity. Thus, provided that two molecules possess a similar activity, they are considered variants as that term is used herein even if the structure of one of the molecules not found in the other, or if the sequence of amino acid residues is not identical.

For example, a variant of an RVG peptide can contain a mutation or modification that differs from a reference amino acid in SEQ ID NO:13. In some embodiments, a variant of SEQ ID NO:13 is a fragment of SEQ ID NO:13 as disclosed herein. In some embodiments, a variant can be a different isoform of SEQ ID NO:13 or can comprise different isomer amino acids. Variants can be naturally-occurring, synthetic, recombinant, or chemically modified polynucleotides or polypeptides isolated or generated using methods well known in the art. Variants can include conservative or non-conservative amino acid changes, as described below. Polynucleotide changes can result in amino acid substitutions, additions, deletions, fusions and truncations in the polypeptide encoded by the reference sequence. Variants can also include insertions, deletions or substitutions of amino acids, including insertions and substitutions of amino acids and other molecules) that do not normally occur in the peptide sequence that is the basis of the variant, for example but not limited to insertion of ornithine which do not normally occur in human proteins. The term "conservative substitution," when describing a polypeptide, refers to a change in the amino acid composition of the polypeptide that does not substantially alter the polypeptide's activity. For example, a conservative substitution refers to substituting an amino acid residue for a different amino acid residue that has similar chemical properties. Conservative amino acid substitutions include replacement of a leucine with an isoleucine or valine, an aspartate with a glutamate, or a threonine with a serine. "Conservative amino acid substitutions" result from replacing one amino acid with another having similar structural and/or chemical properties, such as the replacement of a leucine with an isoleucine or valine, an aspartate with a glutamate, or a threonine with a serine. Thus, a "conservative substitution" of a particular amino acid sequence refers to substitution of those amino acids that are not critical for polypeptide activity or substitution of amino acids with other amino acids having similar properties (e.g., acidic, basic, positively or negatively charged, polar or non-polar, etc.) such that the substitution of even critical amino acids does not reduce the activity of the peptide, (i.e. the ability of the peptide to penetrate the BBB). Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W. H. Freeman and Company (1984).) In some embodiments, individual substitutions, deletions or additions that alter, add or delete a single amino acid or a small percentage of amino acids can also be considered "conservative substitutions" is the change does not reduce the activity of the peptide (i.e. the ability of an RVG peptide variant to penetrate the BBB). Insertions or deletions are typically in the range of about 1 to 5 amino acids. The choice of conservative amino acids may be selected based on the location of the amino acid to be substituted in the peptide, for example if the amino acid is on the exterior of the peptide and expose to solvents, or on the interior and not exposed to solvents.

In alternative embodiments, one can select the amino acid which will substitute an existing amino acid based on the location of the existing amino acid, i.e. its exposure to solvents (i.e. if the amino acid is exposed to solvents or is present on the outer surface of the peptide or polypeptide as compared to internally localized amino acids not exposed to solvents). Selection of such conservative amino acid substitutions are well known in the art, for example as disclosed in Dordo et al, J. Mol. Biol, 1999, 217, 721-739 and Taylor et al, J. Theor. Biol. 119 (1986); 205-218 and S. French and B. Robson, J. Mol. Evol. 19 (1983)171. Accordingly, one can select conservative amino acid substitutions suitable for amino acids on the exterior of a protein or peptide (i.e. amino acids exposed to a solvent), for example, but not limited to, the following substitutions can be used: substitution of Y with F, T with S or K, P with A, E with D or Q, N with D or G, R with K, G with N or A, T with S or K, D with N or E, I with L or V, F with Y, S with T or A, R with K, G with N or A, K with R, A with S, K or P.

In alternative embodiments, one can also select conservative amino acid substitutions encompassed suitable for amino acids on the interior of a protein or peptide, for example one can use suitable conservative substitutions for amino acids is on the interior of a protein or peptide (i.e. the amino acids are not exposed to a solvent), for example but not limited to, one can use the following conservative substitutions: where Y is substituted with F, T with A or S, I with L or V, W with Y, M with L, N with D, G with A, T with A or S, D with N, I with L or V, F with Y or L, S with A or T and A with S, G, T or V. In some embodiments, non-conservative amino acid substitutions are also encompassed within the term of variants. A variant of a RGV peptide, for example a variant of SEQ ID NO:13 is meant to refer to any molecule substantially similar in structure and function to either the entire molecule of SEQ ID NO:13, or to a fragment thereof. A molecule is said to be "substantially similar" to another molecule if both molecules have substantially similar structures or if both molecules possess a similar biological activity, for example if both molecules are able to penetrate the BBB. Thus, provided that two molecules possess a similar activity, (i.e. a variant of an RVG peptide which can penetrate the BBB similar to that of the RVG peptide corresponding to SEQ ID NO:13) are considered variants and are encompassed for use as disclosed herein, even if the structure of one of the molecules not found in the other, or if the sequence of amino acid residues is not identical.

As used herein, the term "nonconservative" refers to substituting an amino acid residue for a different amino acid residue that has different chemical properties. The nonconservative substitutions include, but are not limited to aspartic acid (D) being replaced with glycine (G); asparagine (N) being replaced with lysine (K); or alanine (A) being replaced with arginine (R).

The term "insertions" or "deletions" are typically in the range of about 1 to 5 amino acids. The variation allowed can be experimentally determined by producing the peptide synthetically while systematically making insertions, deletions, or substitutions of nucleotides in the sequence using recombinant DNA techniques.

The term "functional derivative" and "mimetic" are used interchangeably, and refers to a compound which possess a biological activity (either functional or structural) that is substantially similar to a biological activity of the entity or molecule its is a functional derivative of. The term functional derivative is intended to include the fragments, variants, analogues or chemical derivatives of a molecule.

The term "fragment" of a peptide or molecule as used herein refers to any contiguous polypeptide subset of the molecule. Fragments of an RGV peptide, for example fragments of SEQ ID NO:13 useful in the methods as disclosed herein have the same activity as that of SEQ ID NO:13. Stated another way, a fragment of an RVG peptide is a fragment of SEQ ID NO:13 which can penetrate the BBB and/or bind α acetylcholine receptor as the RVG peptide corresponding to SEQ ID NO:13. Fragments as used herein typically are soluble (i.e. not membrane bound). Examples of fragments of SEQ ID NO:13 include but are not limited to any 28, 27, 26, 25, 24, 23, 22, 21, 20, 19, 18, 17, 16 or 15 peptides of SEQ ID NO:13. In some embodiments, a fragment of SEQ ID NO:13 is less than 15 peptides in length.

As used herein, "homologous", when used to describe a polynucleotide, indicates that two polynucleotides, or designated sequences thereof, when optimally aligned and compared, are identical, with appropriate nucleotide insertions or deletions, in at least 70% of the nucleotides, usually from about 75% to 99%, and more preferably at least about 98 to 99% of the nucleotides. The term "homolog" or "homologous" as used herein also refers to homology with respect to structure and/or function. With respect to sequence homology, sequences are homologs if they are at least 50%, at least 60 at least 70%, at least 80%, at least 90%, at least 95% identical, at least 97% identical, or at least 99% identical. The term "substantially homologous" refers to sequences that are at least 90%, at least 95% identical, at least 97% identical or at least 99% identical. Homologous sequences can be the same functional gene in different species.

As used herein, the term "substantial similarity" in the context of polypeptide sequences, indicates that the polypeptide comprises a sequence with at least 60% sequence identity to a reference sequence, or 70%, or 80%, or 85% sequence identity to the reference sequence, or most preferably 90% identity over a comparison window of about 10-20 amino acid residues. In the context of amino acid sequences, "substantial similarity" further includes conservative substitutions of amino acids. Thus, a polypeptide is substantially similar to a second polypeptide, for example, where the two peptides differ by one or more conservative substitutions.

The term "substantial identity" means that two peptide sequences, when optimally aligned, such as by the programs GAP or BESTFIT using default gap weights, share at least 65 percent sequence identity, preferably at least 80 or 90 percent sequence identity, more preferably at least 95 percent sequence identity or more (e.g., 99 percent sequence identity or higher). Preferably, residue positions which are not identical differ by conservative amino acid substitutions.

An "analog" of a molecule such as RGV peptide, for example SEQ ID NO:13 refers to a molecule similar in function to either the entire molecule or to a fragment thereof. The term "analog" is also intended to include allelic, species and induced variants. Analogs typically differ from naturally occurring peptides at one or a few positions, often by virtue of conservative substitutions. Analogs typically exhibit at least 80 or 90% sequence identity with natural peptides. Some analogs also include unnatural amino acids or modifications of N or C terminal amino acids. Examples of unnatural amino acids are, for example but not limited to; acedisubstituted amino acids, N-alkyl amino acids, lactic acid, 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine. Fragments and analogs can be screened for prophylactic or therapeutic efficacy in transgenic animal models as described below.

As used herein, a molecule is said to be a "chemical derivative" of another molecule when it contains additional chemical moieties not normally a part of the molecule. Such moieties can improve the molecule's solubility, absorption, biological half life, etc. The moieties can alternatively decrease the toxicity of the molecule, eliminate or attenuate any undesirable side effect of the molecule, etc. Moieties capable of mediating such effects are disclosed in Remington's Pharmaceutical Sciences, 18th edition, A. R. Gennaro, Ed., MackPubl., Easton, Pa. (1990).

The term "substitution" when referring to a peptide, refers to a change in an amino acid for a different entity, for example another amino acid or amino-acid moiety. Substitutions can be conservative or non-conservative substitutions.

As used herein, the term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T. C, G. U. or 1) or residue occurs in both sequences to yield the number of matched positions, dividing the number of matched positions by the total number of positions in the comparison window (i.e., the window size), and multiplying the result by 100 to yield the percentage of sequence identity.

The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the; percentage of sequence identity is calculated by comparing the reference sequence to the sequence which can include deletions or additions which total 20 percent or less of the reference sequence over the comparison window. The reference sequence can be a subset of a larger sequence. The term "similarity", when used to describe a polypeptide, is determined by comparing the amino acid sequence and the conserved amino acid substitutes of one polypeptide to the sequence of a second polypeptide. The term "homologous", when used to describe a polynucleotide, indicates that two polynucleotides, or designated sequences thereof, when optimally aligned and compared, are identical, with appropriate nucleotide insertions or deletions, in at least 70% of the nucleotides, usually from about 75% to 99%, and more preferably at least about 98 to 99% of the nucleotides.

Determination of homologs of the genes or peptides of the present invention can be easily ascertained by the skilled artisan. The terms "homology" or "identity" or "similarity" are used interchangeably herein and refers to sequence similarity between two peptides or between two nucleic acid molecules. Homology and identity can each be determined by comparing a position in each sequence which can be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. A sequence which is "unrelated" or "non-homologous" shares less than 40% identity, though preferably less than 25% identity with a sequence of the present application.

In one embodiment, the term "RVG peptide homolog" refers to an amino acid sequence that has 40% homology to the full length amino acid sequence of the RVG peptide as disclosed herein, for example the RVG peptide corresponding to SEQ ID NO:13 as disclosed herein, more preferably at least about 50%, still more preferably, at least about 60% homology, still more preferably, at least about 70% homology, even more preferably, at least about 75% homology, yet more preferably, at least about 80% homology, even more preferably at least about 85% homology, still more preferably, at least about 90% homology, and more preferably, at least about 95% homology. As discussed above, the homology is at least about 50% to 100% and all intervals in between (i.e., 55%, 60%, 70%, 75%, 80%, 85%, 90%, 95%, 98%, etc.).

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, for example, by the local homology algorithm of Smith and Waterman (Adv. Appl. Math. 2:482 (1981), which is incorporated by reference herein), by the homology alignment algorithm of Needleman and Wunsch (J. Mol. Biol. 48:443-53 (1970), which is incorporated by reference herein), by the search for similarity method of Pearson and Lipman (Proc. Natl. Acad. Sci. USA 85:2444-48 (1988), which is incorporated by reference herein), by computerized implementations of these algorithms (e.g., GAP, BESTFIT, FASTA, and TFASTA in the Wisconsin Genetics Software Package, Genetics Computer Group, 575 Science Dr., Madison, Wis.), or by visual inspection. (See generally Ausubel et al. (eds.), Current Protocols in Molecular Biology, 4th ed., John Wiley and Sons, New York (1999)).

One example of a useful algorithm is PILEUP. PILEUP creates a multiple sequence alignment from a group of related sequences using progressive, pairwise alignments to show the percent sequence identity. It also plots a tree or dendogram showing the clustering relationships used to create the alignment. PILEUP uses a simplification of the progressive alignment method of Feng and Doolittle (J. Mol. Evol. 25:351-60 (1987), which is incorporated by reference herein). The method used is similar to the method described by Higgins and Sharp (Comput. Appl. Biosci. 5:151-53 (1989), which is incorporated by reference herein). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of an algorithm that is suitable for determining percent sequence identity and sequence similarity is the BLAST algorithm, which is described by Altschul et al. (J. Mol. Biol. 215:403-410 (1990), which is incorporated by reference herein). (See also Zhang et al., Nucleic Acid Res. 26:3986-90 (1998); Altschul et al., Nucleic Acid Res. 25:3389-402 (1997), which are incorporated by reference herein). Software for performing BLAST analyses is publicly available through the National Center for Biotechnology Information internet web site. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990), supra). These initial neighborhood word hits act as seeds for initiating searches to find longer HSPs containing them. The word hits are then extended in both directions along each sequence for as far as the cumulative alignment score can be increased. Extension of the word hits in each direction is halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff and Henikoff, Proc. Natl. Acad. Sci. USA 89:10915-9 (1992), which is incorporated by reference herein) alignments (B) of 50, expectation (E) of 10, M=5, N=-4, and a comparison of both strands.

In addition to calculating percent sequence identity, the BLAST algorithm also performs a statistical analysis of the similarity between two sequences (see, e.g., Karlin and Altschul, Proc. Natl. Acad. Sci. USA 90:5873-77 (1993), which is incorporated by reference herein). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more typically less than about 0.01, and most typically less than about 0.001.

In another embodiment, targeting agents other than the RVG peptide are encompassed for use in the present invention. Examples of such targeting agents include, but are not limited to other molecules capable of delivering attached cargo across the BBB. Such BBB targeting agents can be any of the known targeting moieties that undergo receptor mediated transport across the BBB via endogenous peptide receptor transport systems localized in the brain capillary endothelial plasma membrane, which forms the BBB in vivo. In some embodiments, targeting agents useful in the methods of the present invention are, for example but not limited to insulin, transferrin, insulin-like growth factor (IGF), leptin, low density lipoprotein (LDL), and the corresponding peptides, peptide fragments, peptidomimetics or derivatives thereof, as well as monoclonal antibodies that mimic these endogenous peptides. In some embodiment, a targeting agent is a avimer of fragments, for example but not limited to the binding domains of insulin, transferrin, insulin-like growth factor (IGF), leptin or low density lipoprotein (LDL) proteins, thus enabling multi-receptor targeting of receptors expressed on the surface of cells of the BBB.

Without being bound by theory, peptidomimetic monoclonal antibodies are also useful as targeting agents in the methods of the present invention. Such antibodies bind to exofacial epitopes on the BBB receptor, removed from the binding site of the endogenous peptide ligand, and "piggy-back" across the BBB via the endogenous peptide receptor-mediated transcytosis system. Peptidomimetic monoclonal antibodies are species specific. For example, the OX26 murine monoclonal antibody to the rat transferrin receptor is used for drug delivery to the rat brain (Pardridge et al. 1991. J Pharmacol Exp Ther 256:66-70); however, variants or derivatives of transferring targeting agents are preferred in humans (Lee et al. 2000. J. Pharmacol. Exp Ther 292: 1048-1052). Monoclonal antibodies to the human insulin receptor (HIR) are also useful for delivering the pharmaceutical composition to the human brain. In some embodiments, "humanized" monoclonal antibodies are used. Exemplary, humanized monoclonal antibodies to the human insulin receptor that are particularly well-suited for use in the present invention are described in detail in U.S. Patent App. No. 2004/0101904, the contents of which application are hereby specifically incorporated by reference. Other targeting agents useful in the methods as disclosed herein are, for example the rat 8D3 or rat R17-217 monoclonal antibody to the mouse transferrin receptor for drug delivery to mouse brain (Lee et al. 2000. J Pharmacol Exp Ther 292: 1048-1052), or murine, chimeric or humanized antibodies to the human or animal transferrin receptor, the human or animal leptin receptor, the human or animal IGF receptor, the human or animal LDL receptor, the human or animal acetylated LDL receptor.

The term "targeting agent" or "targeting moiety" refers to an agent that homes in on or selectively targets or preferentially associates or binds to a particular tissue, cell type, receptor, or other molecule or particle f interest. In the methods of the present invention, the targeting agent promotes transport or preferential localization of an effector agent to the target of interest, i.e., neuronal cells. One targeting agent of the present invention comprises an amino acid sequence derived from the rabies virus glycoprotein (RVG) that is effective in binding to cells expressing the α subunit of the acetylcholine receptor, including, for example, brain cells, spinal cord cells, neuronal cells, glia cells and endothelial cells comprising the BBB.

As used herein, the term "target cells" is used herein to refer to cells which sit entirely within BBB-protected CNS tissue. The term "target cells" as used herein also refers to cells expressing the α subunit of the acetylcholine receptor. In one embodiment, the target cells express α type 1 and/or α type 7 acetylcholine receptor. An RVG peptide as disclosed herein binds to the α-subunit of the acetylcholine receptor. Accordingly, an RVG peptide as disclosed herein is useful as a targeting moiety for the selective targeting of cells expressing the α subunit of the acetylcholine receptor. Cells expressing the α subunit of the acetylcholine receptor include, for example, neurons, glial cells and endothelial cells comprising the blood brain barrier. Target cells of the present invention also include, cells whose endogenous milieu is separated by the BBB, for example, cells in the central nervous system, e.g., brain cells, spinal cord cells, glial cells and other cells supporting neurons, for e.g. astrocytes or "nursing cells" and cells of the central nervous system. In some embodiments, the target cells can be any cell expressing the α subunit of acetylcholine receptor or a homologue thereof, such as for example but not limited to neuronal cells in a subject (i.e. in vivo), neuronal cells ex vivo or cultured neuronal cells (i.e. in vitro) such as, for example as primary neuronal cultured cells. In some embodiments, the target cells are neuronal precursor or neuronal progenitor cells, such as neuronal progenitor stem cells that express the α subunit of the acetylcholine receptor or a homologue thereof.

The term "glial cells" or "glia" (also called neuroglial cells), which are used interchangeably herein refers to various types of cells which cannot receive or transmit nerve signals, and which instead support and serve the neurons located inside the BBB. These glial cells perform various activities that can be regarded as supporting, housekeeping, and "nursing" functions within the CNS. Glial cells are divided into various categories, including oligodendroglia cells, astrocytes, ependymal cells, and microglia cells and are commonly known by persons of ordinary skill in the art.

The term "selectively target" as used herein refers to the ability of a targeting agent to home in on or bind to a target cell with a greater affinity than to non-target cells. For example, about 10%, about 20%, about 30%, about 40%, preferably about 50%, more preferably about 60%, more preferably about 70%, still more preferably about 80%, still more preferably about 90%, still more preferably about 100% or greater affinity for the target cell relative to non-target cells.

The term "amino acid" is used in its broadest sense, and includes naturally occurring amino acids as well as non-naturally occurring amino acids, including amino acid analogs and derivatives. For example, homo-phenylalanine, citrulline, and norleucine are considered amino acids for the purposes of the invention. "Amino acids" also includes amino residues such as proline and hydroxyproline. The side chains can be either the (R) or (S) configuration. If non-naturally occurring side chains are used, non-amino acid substituents can be used.

The term "peptide" as used herein, refers to a compound made up of a single chain of D- or L-amino acids or a mixture of D- and L-amino acids joined by peptide bonds. Generally, peptides contain at least two amino acid residues and are less than about 50 amino acids in length.

The terms "peptide" "polypeptide" and "protein" are used interchangeably to refer to a polymer of amino acid residues, and are not limited to a minimum length. Thus, peptides, oligopeptides, dimers, multimers, and the like, whether produced biologically, recombinantly, or synthetically and whether composed of naturally occurring or non-naturally occurring amino acids, are included within this definition. Both full-length proteins and fragments thereof are encompassed by the definition. The terms also include co-translational (e.g., signal peptide cleavage) and post-translational modifications of the polypeptide, such as, for example, disulfide-bond formation, glycosylation, acetylation, phosphorylation, proteolytic cleavage (e.g., cleavage by furins or metalloproteases), and the like. Furthermore, for purposes of the present invention, a "polypeptide" refers to a protein that includes modifications, such as deletions, additions, and substitutions (generally conservative in nature as would be known to a person in the art), to the native sequence, as long as the protein maintains the desired activity. These modifications can be deliberate, as through site-directed mutagenesis, or can be accidental, such as through mutations of hosts that produce the proteins, or errors due to PCR amplification or other recombinant DNA methods.

The term "recombinant" as used herein to describe a nucleic acid molecule, means a polynucleotide of genomic, cDNA, viral, semisynthetic, and/or synthetic origin, which, by virtue of its origin or manipulation, is not associated with all or a portion of the polynucleotide with which it is associated in nature. The term recombinant as used with respect to a protein or polypeptide, means a polypeptide produced by expression of a recombinant polynucleotide. The term recombinant as used with respect to a host cell means a host cell into which a recombinant polynucleotide has been introduced. Recombinant is also used herein to refer to, with reference to material (e.g., a cell, a nucleic acid, a protein, or a vector) that the material has been modified by the introduction of a heterologous material (e.g., a cell, a nucleic acid, a protein, or a vector).

The term "polymer" as used herein, refers to a linear chain of two or more identical or non-identical subunits joined by covalent bonds. A peptide is an example of a polymer that can be composed of identical or non-identical amino acid subunits that are joined by peptide linkages.

As used herein, the term "gene" refers to a nucleic acid comprising an open reading frame encoding a polypeptide, including both exon and (optionally) intron sequences. A "gene" refers to coding sequence of a gene product, as well as non-coding regions of the gene product, including 5'UTR and 3'UTR regions, introns and the promoter of the gene product. These definitions generally refer to a single-stranded molecule, but in specific embodiments will also encompass an additional strand that is partially, substantially or fully complementary to the single-stranded molecule. Thus, a nucleic acid can encompass a double-stranded molecule or a double-stranded molecule that comprises one or more complementary strand(s) or "complement(s)" of a particular sequence comprising a molecule. As used herein, a single stranded nucleic acid can be denoted by the prefix "ss", a double stranded nucleic acid by the prefix "ds", and a triple stranded nucleic acid by the prefix "ts." The term "gene" refers to the segment of DNA involved in producing a polypeptide chain, it includes regions preceding and following the coding region as well as intervening sequences (introns) between individual coding segments (exons). A "promoter" is a region of a nucleic acid sequence at which initiation and rate of transcription are controlled. It can contain elements at which regulatory proteins and molecules can bind, such as RNA polymerase and other transcription factors, to initiate the specific transcription of a nucleic acid sequence. The term "enhancer" refers to a cis-acting regulatory sequence involved in the transcriptional activation of a nucleic acid sequence. An enhancer can function in either orientation and can be upstream or downstream of the promoter. As used herein, the term "gene product(s)" is used to refer to include RNA transcribed from a gene, or a polypeptide encoded by a gene or translated from RNA.

The term "protein" as used herein, refers to a compound that is composed of linearly arranged amino acids linked by peptide bonds, but in contrast to peptides, has a well-defined conformation. Proteins, as opposed to peptides, generally consist of chains of 50 or more amino acids.

The incorporation of non-natural amino acids, including synthetic non-native amino acids, substituted amino acids, or one or more D-amino acids into the peptides (or other components of the composition, with exception for protease recognition sequences) is desirable in certain situations. D-amino acid-containing peptides exhibit increased stability in vitro or in vivo compared to L-amino acid-containing forms. Thus, the construction of peptides incorporating D-amino acids can be particularly useful when greater in vivo or intracellular stability is desired or required. More specifically, D-peptides are resistant to endogenous peptidases and proteases, thereby providing better oral trans-epithelial and transdermal delivery of linked drugs and conjugates, improved bioavailability of membrane-permanent complexes (see below for further discussion), and prolonged intravascular and interstitial lifetimes when such properties are desirable. The use of D-isomer peptides can also enhance transdermal and oral trans-epithelial delivery of linked drugs and other cargo molecules. Additionally, D-peptides cannot be processed efficiently for major histocompatibility complex class II-restricted presentation to T helper cells, and are therefore less likely to induce humoral immune responses in the whole organism. Peptide conjugates can therefore be constructed using, for example, D-isomer forms of cell penetrating peptide sequences, L-isomer forms of cleavage sites, and D-isomer forms of therapeutic peptides.

In yet a further embodiment, the peptides are retro-inverso peptides. A "retro-inverso peptide" refers to a peptide with a reversal of the direction of the peptide bond on at least one position, i.e., a reversal of the amino- and carboxy-termini with respect to the side chain of the amino acid. Thus, a retro-inverso analogue has reversed termini and reversed direction of peptide bonds while approximately maintaining the topology of the side chains as in the native peptide sequence. The retro-inverso peptide can contain L-amino acids or D-amino acids, or a mixture of L-amino acids and D-amino acids, up to all of the amino acids being the D-isomer. Partial retro-inverso peptide analogues are polypeptides in which only part of the sequence is reversed and replaced with enantiomeric amino acid residues. Since the retro-inverted portion of such an analogue has reversed amino and carboxyl termini, the amino acid residues flanking the retro-inverted portion are replaced by side-chain-analogous α-substituted geminal-diaminomethanes and malonates, respectively. Retro-inverso forms of cell penetrating peptides have been found to work as efficiently in translocating across a membrane as the natural forms. Synthesis of retro-inverso peptide analogues are described in Bonelli, F. et al., Int J Pept Protein Res. 24(6):553-6 (1984); Verdini, A. and Viscomi, G. C., J. Chem. Soc. Perkin Trans. 1:697-701 (1985); and U.S. Pat. No. 6,261,569, which are incorporated herein in their entirety by reference. Processes for the solid-phase synthesis of partial retro-inverso peptide analogues have been described (EP 97994-B) which is also incorporated herein in its entirety by reference.

In one embodiment, the targeted delivery composition includes polymers, for example peptides such as an RVG peptide and a peptide carrier particle, comprised of D- or L-amino acid residues. Use of naturally occurring L-amino acid residues in the transport polymers has the advantage that break-down products should be relatively non-toxic to the cell or organism.

In some embodiments, the peptide carrier particle comprises arginine amino acid subunits, for example α-amino-δ-guanidi-novaleric acid and α-amino-ε-amidinohexanoic acid (isosteric amidino analog). In some embodiments, the guanidinium group in arginine has a pKa of about 12.5. More generally, in some embodiments each polymer subunit of a peptide carrier particle contains a highly basic sidechain moiety which (i) has a pKa of greater than 11, more preferably 12.5 or greater, and (ii) contains, in its protonated state, at least two geminal amino groups ($NH_2$) which share a resonance-stabilized positive charge, which gives the moiety a bidentate character. Other amino acids, such as α-amino-β-guanidinopropionic acid, α-amino-γ-guanidinobutyric acid, or α-amino-ε-guanidinocaproic acid can also be used (containing 2, 3 or 5 linker atoms, respectively, between the backbone chain and the central guanidinium carbon).

In alternative embodiments, the peptides as disclosed herein, for example an RVG peptide and/or peptide carrier particles can comprise D-amino acids. Compositions containing exclusively D-amino acids have the advantage of decreased enzymatic degradation. However, they can also remain largely intact within the target cell. Such stability is generally not problematic if the agent being delivered to the cell is biologically active when a peptide carrier particle is still attached. For agents that are inactive when conjugated with a peptide carrier particle, a linker that is cleavable and can be cleaved by a suitable mechanism in a target cell (e.g., by enzyme- or solvent-mediated cleavage within a cell) can be included to promote release of the agent from the peptide carrier particle in the target cell.

Carrier Particles

The carrier particles of the effector agents include any carrier particle modifiable by attachment of a targeting agent known to the skilled artisan. Carrier particles include but are not limited to liposomal or polymeric nanoparticles such as liposomes, proteins, and non-protein polymers. Carrier particles can be selected according to their ability to transport the effector agent of choice and the ability to covalently attach the targeting agent to the carrier particle.

In some embodiments, carrier particles include colloidal dispersion systems, which include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. In some embodiments, the carrier particle comprises a plurality of liposomes. Liposomes are microscopic spheres having an aqueous core surrounded by one or more outer layers made up of lipids arranged in a bilayer configuration (see, generally, Chonn et al., Current Op. Biotech. 1995, 6, 698-708). Other carrier particles are cellular uptake or membrane-disruption moieties, for example polyamines, e.g. spermidine or spermine groups, or polylysines; lipids and lipophilic groups; polymyxin or polymyxin-derived peptides; octapeptin; membrane pore-forming peptides; ionophores; protamine; aminoglycosides; polyenes; and the like. Other potentially useful functional groups include intercalating agents; radical generators; alkylating agents; detectable labels; chelators; or the like.

One can use other carrier particles, for example lipid particle or vesicle, such as a liposome or microcrystal, which may be suitable for parenteral administration. The particles may be of any suitable structure, such as unilamellar or plurilamellar, so long as the antisense oligonucleotide is contained therein. Positively charged lipids such as N-[I-(2,3dioleoyloxi)propyl]-N,N,N-trimethyl-anunoniummethyl-sulfate, or "DOTAP," are particularly preferred for such particles and vesicles. The preparation of such lipid particles is well known. See, e.g., U.S. Pat. Nos. 4,880,635; 4,906,477; 4,911,928; 4,917,951; 4,920,016; and 4,921,757 which are incorporated herein by reference. Other non-toxic lipid based vehicle components may likewise be utilized to facilitate uptake of the antisense compound by the cell.

In some embodiments, a carrier particle is a liposome. The outer surface of the liposomes can be modified with a long-circulating agent, e.g., PEG, e.g., hyaluronic acid (HA). The liposomes can be modified with a cryoprotectant, e.g., a sugar, such as trehalose, sucrose, mannose or glucose, e.g., HA. In one embodiment, a liposome is coated with HA. HA acts as both a long-circulating agent and a cryoprotectant. The liposome is modified by attachment of the targeting moiety. In another embodiment, the targeting moiety is covalently attached to HA, which is bound to the liposome surface. Alternatively, the carrier particle is a micelle. Alternatively, the micelle is modified with a cryoprotectant, e.g., HA, PEG.

Liposomes useful in the methods and compositions as disclosed herein can be produced from combinations of lipid materials well known and routinely utilized in the art to produce liposomes. Lipids can include relatively rigid varieties, such as sphingomyelin, or fluid types, such as phospholipids having unsaturated acyl chains. "Phospholipid" refers to any one phospholipid or combination of phospholipids capable of forming liposomes. Phosphatidylcholines (PC), including those obtained from egg, soy beans or other plant sources or those that are partially or wholly synthetic, or of variable lipid chain length and unsaturation are suitable for use in the present invention. Synthetic, semisynthetic and natural product phosphatidylcholines including, but not limited to, distearoylphosphatidylcholine (DSPC), hydrogenated soy phosphatidylcholine (HSPC), soy phosphatidylcholine (soy PC), egg phosphatidylcholine (egg PC), hydrogenated egg phosphatidylcholine (HEPC), dipalmitoylphosphatidylcholine (DPPC) and dimyristoylphosphatidylcholine (DMPC) are suitable phosphatidylcholines for use in this invention. All of these phospholipids are commercially available. Further, phosphatidylglycerols (PG) and phosphatic acid (PA) are also suitable phospholipids for use in the present invention and include, but are not limited to, dimyristoylphosphatidylglycerol (DMPG), dilaurylphosphatidylglycerol (DLPG), dipalmitoylphosphatidylglycerol (DPPG), distearoylphosphatidylglycerol (DSPG) dimyristoylphosphatidic acid (DMPA), distearoylphosphatidic acid (DSPA), dilaurylphosphatidic acid (DLPA), and dipalmitoylphosphatidic acid (DPPA). Distearoylphosphatidylglycerol (DSPG) is the preferred negatively charged lipid when used in formulations. Other suitable phospholipids include phosphatidylethanolamines, phosphatidylinositols, sphingomyelins, and phosphatidic acids containing lauric, myristic, stearoyl, and palmitic acid chains. For the purpose of stabilizing the lipid membrane, it is preferred to add an additional lipid component, such as cholesterol. Preferred lipids for producing liposomes according to the invention include phosphatidylethanolamine (PE) and phosphatidylcholine (PC) in further combination with cholesterol (CH). According to one embodiment of the invention, a combination of lipids and cholesterol for producing the liposomes of the invention comprise a PE:PC:Chol molar ratio of 3:1:1. Further, incorporation of polyethylene glycol (PEG) containing phospholipids is also contemplated by the present invention.

Liposomes useful in the methods and compositions as disclosed herein can be obtained by any method known to the skilled artisan. For example, the liposome preparation of the present invention can be produced by reverse phase evaporation (REV) method (see U.S. Pat. No. 4,235,871), infusion procedures, or detergent dilution. A review of these and other methods for producing liposomes can be found in the text Liposomes, Marc Ostro, ed., Marcel Dekker, Inc., New York, 1983, Chapter 1. See also Szoka Jr. et al., (1980, Ann. Rev. Biophys. Bioeng., 9:467). A method for forming ULVs is described in Cullis et al., PCT Publication No. 87/00238, Jan. 16, 1986, entitled "Extrusion Technique for Producing Unilamellar Vesicles". Multilamellar liposomes (MLV) can be prepared by the lipid-film method, wherein the lipids are dissolved in a chloroform-methanol solution (3:1, vol/vol), evaporated to dryness under reduced pressure and hydrated by a swelling solution. Then, the solution is subjected to extensive agitation and incubation, e.g., 2 hour, e.g., at 37° C. After incubation, unilamellar liposomes (ULV) are obtained by extrusion. The extrusion step modifies liposomes by reducing the size of the liposomes to a preferred average diameter. Alternatively, liposomes of the desired size can be selected using techniques such as filtration or other size selection techniques. While the size-selected liposomes of the invention should have an average diameter of less than about 300 nm, it is preferred that they are selected to have an average diameter of less than about 200 nm with an average diameter of less than about 100 nm being particularly preferred. When the liposome of the present invention is a unilamellar liposome, it preferably is selected to have an average diameter of less than about 200 nm. The most preferred unilamellar liposomes of the invention have an average diameter of less than about 100 nm. It is understood, however, that multivesicular liposomes of the invention derived from smaller unilamellar liposomes will generally be larger and can have an average diameter of about less than 1000 nm. Preferred multivesicular liposomes of the invention have an average diameter of less than about 800 nm, and less than about 500 nm while most preferred multivesicular liposomes of the invention have an average diameter of less than about 300 nm.

A method for coating the liposomes or other polymeric nanoparticles with targeting agents, such as an RVG peptide comprising SEQ ID NO:13 or variants, derivatives or fragments thereof are disclosed in U.S. Provisional Application No. 60/794,361 filed Apr. 24, 2006, and International Patent Application: PCT/US07/10075 filed Apr. 24, 2007 with are incorporated in their entirety herein by reference.

In some embodiments, the outer surface of the liposomes can be further modified with a long-circulating agent. The modification of the liposomes with a hydrophilic polymer as the long-circulating agent is known to enable to prolong the half-life of the liposomes in the blood. Examples of the hydrophilic polymer include polyethylene glycol, polymethylethylene glycol, polyhydroxypropylene glycol, polypropylene glycol, polymethylpropylene glycol and polyhydroxypropylene oxide. In one embodiment, a hydrophilic polymer is polyethylene glycol (PEG). Glycosaminoglycans, e.g., hyaluronic acid, can also be used as long-circulating agents.

In some embodiments, the targeting agent, such as an RVG peptide comprising SEQ ID NO:13 or a derivative, variant or fragment thereof is conjugated to a cryoprotectant present on the liposome, e.g., HA. Crosslinking reagents include glutaraldehyde (GAD), bifunctional oxirane (OXR), ethylene glycol diglycidyl ether (EGDE), N-hydroxysuccinimide (NHS), and a water soluble carbodiimide, preferably 1-ethyl-3-(3-dimethylaminopropyl) carbodiimide (EDC). As is known to the skilled artisan, any crosslinking chemistry can be used, including, but not limited to, thioether, thioester, malimide and thiol, amine-carboxyl, amine-amine, and others listed in organic chemistry manuals, such as, Elements of Organic Chemistry, Isaak and Henry Zimmerman Macmillan Publishing Co., Inc. 866 Third Avenue, New York, N.Y. 10022. Through the complex chemistry of cross-linking, linkage of the amine residues of the recognizing substance and liposomes is established.

In some embodiments, after the targeting agent is conjugated or covalently attached to the lipid particle by way of covalent linkage to the cryoprotectant, or by way of covalent linkage to another targeting agent covalently linked to the cryoprotectant, the lipid particle may be lyophilized. The lipid particle may remain lyophilized prior to rehydration, or prior to rehydration and encapsulation of the agent of interest, for extended periods of time. In one embodiment, the lipid particle remains lyophilized for about 1 month, about 2 months, about 3 months, about 6 months, about 9 months, about 12 months, about 18 months, about 2 years or more prior to rehydration.

In another embodiment, the carrier particle is a cyclodextrin-based nanoparticle. Polycation formulated nanoparticles have been used for drug delivery into the brain as well as for systemic delivery of siRNA [114,115]. A unique cyclodextrin-based nanoparticle technology has been developed for targeted gene delivery in vivo [116-123]. This delivery system consists of two components. The first component is a biologically non-toxic cyclodextrin-containing polycation (CDP). CDPs self-assemble with siRNA to form colloidal particles about 50 nm in diameter and protects si/shRNA against degradation in body fluids. Moreover, the CDP has been engineered to contain imidazole groups at their termini to assist in the intracellular trafficking and release of the nucleic acid [123]. CDP also enables assembly with the second component. The second component is an adamantane-terminated polyethylene glycol (PEG) modifier for stabilizing the particles in order to minimize interactions with plasma and to attach cell surface targeting molecules such as transferrin or RVG peptides. Thus, the advantages of this delivery system are: 1) since the CDP protects the siRNA from degradation, chemical modification of the nucleic acid is unnecessary, 2) the colloidal particles do not aggregate and have extended life in biological fluids because of the surface decoration with PEG that occurs via inclusion complex formation between the terminal adamantane and the cyclodextrins [123], 3) cell type-specific targeted delivery is possible because some of the PEG chains contain targeting ligands, 4) it does not induce an immune response [116,119], and 5) in vivo delivery does not produce an interferon response even when a siRNA is used that contains a motif known to be immunostimulatory when delivered in vivo with lipids [116].

In another embodiment, the carrier particle is a cationic peptide, e.g., protamine. See, for example, WO 06/023491, which is specifically incorporated herein in its entirety by reference.

The glycosaminoglycan carrier particles disclosed in U.S. Patent Appl. No. 20040241248 and the glycoprotein carrier particles in WO 06/017195, which are incorporated herein in their entirety by reference, are useful in the methods of the present invention. Similar naturally occurring polymer-type carriers known to the skilled artisan are also useful in the methods of the present invention.

Soluble non-protein polymers are useful as carrier particles. Such polymers can include polyvinylpyrrolidone, pyran copolymer, polyhydroxypropylrnethacrylamidephenol, polyhydroxyethylaspartamidephenol, or polyethyleneoxidepolylysine substituted with palitoyl residues. Furthermore, the therapeutic agents can be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels. The therapeutic agents can also be affixed to rigid polymers and other structures such as fullerenes or Buckeyballs.

The carrier particle can be conjugated to the targeting agent, for example RVG peptide or variant thereof. The conjugation can be a non-covalent or covalent interaction, for example, by means of chemical crosslinkage or conjugation.

As used herein, the term "conjugate" or "conjugation" refers to the attachment of two or more entities to form one entity. For example, the methods of the present invention provide conjugation of a targeting agent (for example an RVG peptide or variant or fragment or derivative) joined with another entity, for example a carrier particle, for example a liposome or cell penetrating agent, for e.g. a cell penetrating peptide. The attachment can be by means of linkers, chemical modification, peptide linkers, chemical linkers, covalent or non-covalent bonds, or protein fusion or by any means known to one skilled in the art. The joining can be permanent or reversible. In some embodiments, several linkers can be included in order to take advantage of desired properties of each linker and each protein in the conjugate. Flexible linkers and linkers that increase the solubility of the conjugates are contemplated for use alone or with other linkers as disclosed herein. Peptide linkers can be linked by expressing DNA encoding the linker to one or more proteins in the conjugate. Linkers can be acid cleavable, photocleavable and heat sensitive linkers. Methods for conjugation are well known by persons skilled in the art and are encompassed for use in the present invention.

According to the present invention, the targeting agent, for example an RVG peptide, can be linked to the carrier particle entity via any suitable means, as known in the art, see for example U.S. Pat. Nos. 4,625,014, 5,057,301 and 5,514,363, which are incorporated herein in their entirety by reference. For example, the agent to be transported can be covalently conjugated to the transporting entity, either directly or through one or more linkers. In one embodiment, the transporting entity of the present invention is conjugated directly to an agent to be transported. In another embodiment, the transporting entity of the present invention is conjugated to an agent to be transported via a linker, e.g. a transport enhancing linker.

A large variety of methods for conjugation of targeting agents with carrier particles or diagnostic moieties are known in the art. Such methods are e.g. described by Hermanson (1996, Bioconjugate Techniques, Academic Press), in U.S. Pat. No. 6,180,084 and U.S. Pat. No. 6,264,914 which are incorporated herein in their entirety by reference and include e.g. methods used to link haptens to carriers proteins as routinely used in applied immunology (see Harlow and Lane, 1988, "Antibodies: A laboratory manual", Cold Spring Harbor Laboratory Press, Cold Spring Harbor, N.Y.). It is recognized that, in some cases, a targeting agent or carrier particle can lose efficacy or functionality upon conjugation depending, e.g., on the conjugation procedure or the chemical group utilised therein. However, given the large variety of methods for conjugation the skilled person is able to find a conjugation method that does not or least affects the efficacy or functionality of the entities to be conjugated.

Suitable methods for conjugation of a targeting agent with carrier particle include e.g. carbodimide conjugation (Bauminger and Wilchek, 1980, Meth. Enzymol. 70: 151-159). Alternatively, a moiety can be coupled to a targeting agent as described by Nagy et al., Proc. Natl. Acad. Sci. USA 93:7269-7273 (1996), and Nagy et al., Proc. Natl. Acad. Sci. USA 95:1794-1799 (1998), each of which are incorporated herein by reference. Another method for conjugating one can use is, for example sodium periodate oxidation followed by reductive alkylation of appropriate reactants and glutaraldehyde crosslinking.

One can use a variety of different linkers to conjugate the targeting agent, for example RVG peptide as described herein to a carrier particle, for example but not limited to aminocaproic horse radish peroxidase (HRP) or a heterobiofunctional cross-linker, e.g. carbonyl reactive and sulfhydryl-reactive cross-linker. Heterobiofunctional cross linking reagents usually contain two reactive groups that can be coupled to two different function targets on proteins and other macromolecules in a two or three-step process, which can limit the degree of polymerization often associated with using homobiofunctional cross-linkers. Such multistep protocols can offer a great control of conjugate size and the molar ratio of components.

The term "linker" refers to any means to join two or more entities, for example a peptide with another peptide, or a liposome. A linker can be a covalent linker or a non-covalent linker. Examples of covalent linkers include covalent bonds or a linker moiety covalently attached to one or more of the proteins to be linked. The linker can also be a non-covalent bond, e.g. an organometallic bond through a metal center such as platinum atom. For covalent linkages, various functionalities can be used, such as amide groups, including carbonic acid derivatives, ethers, esters, including organic and inorganic esters, amino, urethane, urea and the like. To provide for linking, the effector molecule and/or the probe can be modified by oxidation, hydroxylation, substitution, reduction etc. to provide a site for coupling. It will be appreciated that modification which do not significantly decrease the function of the target agent, for example RVG peptide and/or the carrier particle are preferred.

In some embodiments where the carrier particle is a liposome or polymeric nanoparticle, the effector agent and/or targeting agent, such as an RVG peptide is captured within a liposomes or polymeric nanoparticle or immunoliposomes. For example, a suspension of RVG peptide or variant or fragment thereof and/or effector agent can be encapsulated in micelles to form liposomes by conventional methods (U.S. Pat. No. 5,043,164, U.S. Pat. No. 4,957,735, I5 U.S. Pat. No. 4,925,661; Connor and Huang, (1985) J. Cell Biol. 101: 581; Lasic D. D. (1992) Nature 355: 279; Novel Drug Delivery (eds. Prescott and Nimmo, Wiley, New York, 1989); Reddy et al. (1992) J. Immunol. 148:1585), which are incorporated herein in their entirety by reference. Liposomes comprising targeting agent that binds specifically to neurons (e.g., neurons expressing acetylcholine receptor (AchR)) or cells of the blood brain barrier can be used to target the agents to those cells. The terms "encapsulation" and "entrapped," as used herein, refer to the incorporation of an agent in a lipid particle. The agent is present in the aqueous interior of the lipid particle. In one embodiment, a portion of the encapsulated agent takes the form of a precipitated salt in the interior of the liposome. The agent may also self precipitate in the interior of the liposome.

In another embodiment where the effector agent is a nucleic acid, e.g., DNA, RNA, siRNA, plasmid DNA, short-hairpin RNA, small temporal RNA (stRNA), microRNA (miRNA), RNA mimetics, or heterochromatic siRNA, the nucleic acid effector agent has a charged backbone that prevents efficient encapsulation in the lipid particle. Accordingly, the nucleic acid effector agent of interest may be condensed with a cationic polymer, e.g., PEI, polyamine spermidine, and spermine, or cationic peptide, e.g., protamine and polylysine, prior to encapsulation in the lipid particle. In some embodiments, the effector agent is not condensed with a cationic polymer.

In some embodiments, an effector agent is encapsulated in the lipid particle or other polymeric nanoparticle in the following manner. The lipid particle or polymeric nanoparticle, in which can additionally comprise a cryoprotectant and/or a targeting agent is provided lyophilized. The effector agent is in an aqueous solution. The effector agent in aqueous solution is utilized to rehydrate the lyophilized lipid particle or nanoparticle. Thus, the effector agent is encapsulated in the rehydrated lipid particle or polymeric nanoparticle. For example but not limited to, the cDNA for the glial cell line derived neurogrowth factor (GDNF) may be targeted to the dopamine cells at the substantia nigra in Parkinson's disease patients.

In some embodiments, two or more effector agents can be delivered by the lipid particle or polymeric nanoparticles by the methods as disclosed herein. In such embodiments, one agent can be hydrophobic and the other hydrophilic. The hydrophobic agent can be added to the lipid particle during formation of the lipid particle. The hydrophobic agent associates with the lipid portion of the lipid particle. The hydrophilic agent is added in the aqueous solution rehydrating the lyophilized lipid particle. An exemplary embodiment of two agent delivery is described below, wherein a condensed siRNA is encapsulated in a liposome and wherein a drug that is poorly soluble in aqueous solution is associated with the lipid portion of the lipid particle. As used herein, "poorly soluble in aqueous solution" refers to a composition that is less that 10% soluble in water.

Any suitable lipid: pharmaceutical agent ratio that is efficacious is contemplated by this invention. Preferred lipid: pharmaceutical agent molar ratios include about 2:1 to about 30:1, about 5:1 to about 100:1, about 10:1 to about 40:1, about 15:1 to about 25:1.

The preferred loading efficiency of therapeutic or pharmaceutical agent is a percent encapsulated pharmaceutical agent of about 50%, about 60%, about 70% or greater. In one embodiment, the loading efficiency for a hydrophilic agent is a range from 50-100%. The preferred loading efficiency of pharmaceutical agent associated with the lipid portion of the lipid particle, e.g., a pharmaceutical agent poorly soluble in aqueous solution, is a percent loaded pharmaceutical agent of about 50%, about 60%, about 70%, about 80%, about 90%, about 100%. In one embodiment, the loading efficiency for a hydrophobic agent in the lipid layer is a range from 80-100%.

In one aspect of the method, the liposome or polymeric nanoparticle is detectably labeled with a label selected from the group including a radioactive label, a fluorescent label, a non-fluorescent label, a dye, or a compound which enhances magnetic resonance imaging (MRI). In one embodiment, the liposome product is detected by acoustic reflectivity. The label may be attached to the exterior of the liposome or may be encapsulated in the interior of the liposome.

In some embodiments, and in the event that the carrier particle is a peptide or protein, and the targeting agent is also a peptide or antibody, or contains amino acids as part of its structure, the targeting agent (for example an RVG peptide) can be fused either in frame or out of frame with the carrier particle to form a fusion protein. In general, the targeting agent (i.e. an RVG peptide) and carrier particle can be fused directly or via one or more amino acid linkers. Any suitable amino acid linkers can be used to modify the stability, conformation, charge, or other structure features of the resulting fusion protein in order to facilitate its transport to target cells. In some embodiments, fusion proteins can also be formed from the carrier particle and effector agent, where both the carrier particle and effector agents are proteins or contain amino acids as part of their structure, and preferably the activity of the effector agent is not compromised by being fused with the carrier particle.

The term "fusion protein" refers to a recombinant protein of two or more fused proteins. Fusion proteins can be produced, for example, by a nucleic acid sequence encoding one protein joined to the nucleic acid encoding another protein such that they constitute a single open-reading frame that can be translated in the cells into a single polypeptide harboring all the intended proteins. The order of arrangement of the proteins can vary. As a non-limiting example, the nucleic acid sequence encoding an RVG peptide can be fused to either the 5' or the 3' end of the nucleic acid sequence encoding a carrier particle. In this manner, on expression of the nucleic acid construct, the RVG peptide is functionally expressed and fused to the N-terminal or C-terminal end of the carrier protein. In certain embodiments, the carrier peptide can be modified such that the carrier protein function (i.e ability to associate with the effector agent) remains unaffected by fusion to the RVG peptide and vice versa, the RVG peptide can be modified, for example RVG peptide variants can be used so that the RVG peptide retains the ability to penetrate or pass through the BBB even when fused with another protein, for example the carrier particle.

The targeted delivery composition can also be prepared via recombinant expression through bacterial or eukaryotic expression systems of a protein-based carrier particle, for example HIV-TAT (SEQ ID NO:15) or a fragment thereof, protamine, and an RVG peptide. Bacterial and eukaryotic expression systems are well known and used routinely by those skilled in the art. Accordingly, in one embodiment a targeted delivery composition comprises an RVG peptide or variant or fragment or derivative thereof, and a polymeric arginine residue of a varying length, such as 9R or 11R as disclosed herein. An example of one such targeted delivery composition is RVG-11dR:

(SEQ ID NO: 14)
YTIWMPENPRPGTPCDIFTNSRGKRASNGGGGRRRRRRRRRRR.

Another example of one such targeted delivery composition is RVG-9dR: YTIWMPENPRPGTPCDIFTNSRGKRASNGGGGRRRRRRRRR (SEQ ID NO: 34). Another example of such a targeted delivery composition comprise an RVG peptide and a protamine peptide: YTIWMPENPRPGTPCDIFTNSRGKRASNGGGGR-SQSRSRYYRQRQRSRRRRRRS (SEQ ID NO: 16). In another embodiment, a targeted delivery composition comprises an RVG peptide and TAT:

(SEQ ID NO: 15)
YTIWMPENPRPGTPCDIFTNSRGKRASNGGGGYGRKKRRQRRRKKRK.

In some embodiments, SEQ ID NO:14 and SEQ ID NO:34 can gave arginine (R) sequentially deleted or added from the C-terminal end, for example deleted by 1, 2, 3, 4, 5, or 6 C-terminal R residues.

In some embodiments, the carrier particle also comprises a cell penetrating agent. A cell penetrating agent can also be covalently attached to a carrier particle, e.g., a liposomal carrier particle. In some embodiments, the composition of the present invention includes a cell penetrating agent and a separate carrier particle. For example, a cell penetrating agent can be attached to a liposomal carrier particle.

Any peptide or fragment thereof, which is capable of crossing a biological membrane, either in vivo or in vitro, is encompassed for use in the methods and compositions of the present invention. Such peptides that are capable of crossing membranes are termed "cell penetrating agents". "Cell penetrating agents" or "translocation agents "comprise agents that facilitate delivery of an associated compound of interest or cargo across a cell membrane. It is known that certain peptides have the ability to penetrate a lipid bilayer (e.g., cell membranes) and translocate an attached cargo across the cell membrane. This is referred to herein as "translocation activity". Without being bound by theory, these membrane penetrating peptides appear to enter the cell, in part, via non-endocytic mechanisms, as indicated by the ability of the cell penetrating peptides to enter the cell at low temperatures (e.g., 4° C.) that would normally inhibit endocytic, receptor-based, internalization pathways.

Generally, the cell penetrating agents are capable of facilitating transfer of a cargo or compound such as an effector agent across a lipid bilayer in a non-selective manner because entry into the cell does not appear to occur by receptor-mediated endocytic pathway. Consequently, the cell penetrating agent is capable of translocating cargoes non-selectively into a variety of cell types. In some embodiments, to control delivery of the compositions into cell types, the compositions can further comprise a cell penetrating peptide inhibitor or an inhibitor of cell penetrating peptide. Modification of the inhibitor results in release of the inhibitory effect and formation of an active cell penetrating composition.

In some embodiments, the cell penetrating agent is a cell penetrating peptide. Methods to synthesize such peptides are well known to one of ordinary skill in the art. For example, several cell penetrating peptides have been identified which can be used as carrier peptides in the methods of the invention for transporting RNA interfering agents across biological membranes. These peptides include, for example, the homeodomain of antennapedia, a *Drosophila* transcription factor (Wang et al., (1995) PNAS USA., 92, 3318-3322); a fragment representing the hydrophobic region of the signal sequence of Kaposi fibroblast growth factor with or without NLS domain (Antopolsky et al. (1999) Bioconj. Chem., 10, 598-606); a signal peptide sequence of caiman crocodylus Ig(5) light chain (Chaloin et al. (1997) Biochem. Biophys. Res. Comm., 243, 601-608); a fusion sequence of HIV envelope glycoprotein gp4114, (Morris et al. (1997) Nucleic Acids Res., 25, 2730-2736); a transportan A-achimeric 27-mer consisting of N-terminal fragment of neuropeptide galanine and membrane interacting wasp venom peptide mastoporan (Lindgren et al., (2000), Bioconjugate Chem., 11, 619-626); a peptide derived from influenza virus hemagglutinin envelop glycoprotein (Bongartz et al., 1994, Nucleic Acids Res., 22, 468 1 4688); RGD peptide; and a peptide derived from the human immunodeficiency virus type-1 ("HIV-1"). Purified HIV-1 TAT protein is taken up from the surrounding medium by human cells growing in culture (Frankel and Pabo, (1988) Cell, 55, pp. 1189-93). TAT protein trans-activates certain HIV genes and is essential for viral replication. The full-length HIV-1 TAT protein has 86 amino acid residues. The HIV tat gene has two exons. TAT amino acids 1-72 are encoded by exon 1, and amino acids 73-86 are encoded by exon 2. The full-length TAT protein is characterized by a basic region which contains two lysines and six arginines (amino acids 47-57) and a cysteine-rich region which contains seven cysteine residues (amino acids 22-37). The basic region (i.e., amino acids 47-57) is thought to be important for nuclear localization and cell penetration (Ruben et al., J. Virol. 63: 1-8 (1989); Hauber et al., J. Virol. 63 1181-1187 (1989); Rudolph et al. (2003) 278(13):11411). The cysteine-rich region mediates the formation of metal-linked dimers in vitro (Frankel et al., Science 240: 70-73 (1988); Frankel, et al., Proc. Natl. Acad. Sci. USA 85: 6297-6300 (1988)) and is essential for its activity as a transactivator (Garcia et al., EMBO J. 7:3143 (1988); Sadaie. et al., J. Virol. 63: 1 (1989)). As in other regulatory proteins, the N-terminal region can be involved in protection against intracellular proteases (Bachmair et al., Cell 56: 1019-1032 (1989). See also, e.g., Morris, M. C. et al., Nature Biotechnol. 19:1173-1176 (2001); Dupont, A. J. and Prochiantz, A., CRC Handbook on Cell Penetrating Peptides, Langel, Editor, CRC Press, (2002); Chaloin, L. et al., Biochemistry 36(37):11179-87 (1997); and Lundberg, P. and Langel, U., J. Mol. Recognit. 16(5):227-233 (2003); all publications incorporated herein by reference.

In one embodiment of the invention, such a cell penetrating agent comprises the basic region comprising amino acids 47-57 of the HIV-1 TAT peptide (SEQ ID NO:1). In another embodiment, a cell penetrating agent comprises the basic region comprising amino acids 48-60 of the HIV-1 TAT peptide (SEQ ID NO:2). In yet another embodiment, a cell penetrating agent comprises the basic region comprising amino acids 49-57, 48-60, or 47-57 of the HIV-1 TAT peptide, does not comprise amino acids 22-36 of the HIV-1 TAT peptide, and does not comprise amino acids 73-86 of the HIV-1 TAT peptide. In still another embodiment, the specific peptides set forth in Table 1, below, or fragments thereof, can be used as cell penetrating agents in the methods and compositions as disclosed herein.

TABLE 1

| PEPTIDE | SEQUENCE | SEQ ID NO: |
|---|---|---|
| HIV-1 TAT (49-57) | RKKRRQRRR | 1 |
| HIV-1 TAT (48-60) | GRKKRRQRRRTPQ | 2 |
| HIV-1 TAT (47-57) | YGRKKRRQRRR | 3 |
| Kaposi fibroblast growth factor | AAV ALL PAV LLA LLA P VQR KRQ KLMP | 4 |
| of caiman crocodylus Ig(5) light chain | MGL GLH LLV LAA ALQ GA | 5 |
| HIV envelope glycoprotein gp41 | GAL FLG FLG AAG STM GA PKS KRK 5 (NLS of the SV40) | 6 |
| Drosophila Antennapedia | RQI KIW FQN RRM KWK K amide | 7 |
| RGD peptide | X-RGD-X | 8 |
| influenza virus hemagglutinin envelop glycoprotein | GLFEAIAGFIENGWEGMIDG GGYC | 9 |

TABLE 1-continued

| PEPTIDE | SEQUENCE | SEQ ID NO: |
|---|---|---|
| transportan A | GWT LNS AGY LLG KIN LKA LAA LAK KIL | 10 |
| Pre-S-peptide | (S)DH QLN PAF | 11 |
| Somatostatin (tyr-3-octreotate) | (S)*FC* YWK TCT | 12 |

(s)optional Serine for coupling
italic = optional D isomer for stability

In yet another embodiment, an active thiol at the 5' end of the sense strand can be coupled to a cysteine reside added to the C terminal end of a cell penetrating agent for delivery into the cytosol (such as a fragment of tat or a fragment of the Drosophila Antennapedia peptide). Internalization via these peptides bypasses the endocytic pathway and therefore removes the danger of rapid degradation in the harsh lysosomal environment, and can reduce the concentration required for biological efficiency compared to free oligonucleotides.

Other arginine rich peptides are also included for use as cell penetrating agents as disclosed herein. For example, a TAT analog can comprise D-amino acids and arginine-substituted TAT (47-60), RNA-binding peptides derived from virus proteins such as HIV-1 Rev, and flock house virus coat proteins, and the DNA binding sequences of leucine zipper proteins, such as cancer-related proteins c-Fos and c-Jun and the yeast transcription factor GCN4, all of which contain several arginine residues (see Futaki, et al. (2001) J. Biol Chem 276(8):5836-5840 and Futaki, S. (2002) Int J. Pharm 245(1-2):1-7, which are incorporated herein by reference). In one embodiment, the arginine rich peptide contains about 4 to about 11 arginine residues. In another embodiment, the arginine residues are contiguous residues.

In another embodiment, the cell penetrating peptides comprise a membrane signal peptide or membrane translocation sequence capable of translocating across the cell membrane. A cell penetrating "signal peptide" or "signal sequence" refers to a sequence of amino acids generally of a length of about 10 to about 50 or more amino acid residues, many (typically about 55-60%) residues of which are hydrophobic such that they have a hydrophobic, lipid-soluble portion. Generally, a signal peptide is a peptide capable of penetrating through the cell membrane to allow the import and/or export of cellular proteins.

As used herein a "signal sequence", also known as a "leader sequence" can be used, when desired, to direct the peptide through a membrane of a cell. Such a sequence refers to an amino acid sequence which can be naturally present on the peptides of the present invention or provided from heterologous sources by recombinant DNA techniques.

Signal peptides can be selected from the SIGPEP database (von Heijne, Protein Sequence Data Analysis 1:4142 (1987); von Heijne and Abrahmsen, L., FEBS Letters 224:439-446 (1989)). Algorithms can also predict signal peptide sequences for use in the compositions (see, e.g., SIGFIND— Signal Peptide Prediction Server version SignalP V2.0b2, Bendtsen et al. "Improved prediction of signal peptides: SignalP 3.0." J. Mol. Biol., 340:783-795, 2004; Nielsen et al. "Identification of prokaryotic and eukaryotic signal peptides and prediction of their cleavage sites." Protein Engineering, 10:1-6, 1997; Bairoch and Boeckmann, "The SWISS-PROT protein sequence data bank: current status" Nucleic Acids Res. 22:3578-3580, 1994.). When a specific cell type is to be targeted, a signal peptide used by that cell type can be chosen. For example, signal peptides encoded by a particular oncogene can be selected for use in targeting cells in which the oncogene is expressed. Additionally, signal peptides endogenous to the cell type can be chosen for importing biologically active molecules into that cell type. Any selected signal peptide can be routinely tested for the ability to translocate across the cell membrane of any given cell type (see, e.g., U.S. Pat. No. 5,807,746, which is incorporated herein in its entirety by reference). Exemplary signal peptide sequences with membrane translocation activity include, by way of example and not limitation, those of Karposi fibroblast growth factor AAVALLPAVLLALLAPA-AADQNQLMP. (SEQ ID NO: 17) or a derivative, variant or fragment thereof.

In another embodiment of the present invention, cell penetrating agents comprise Herpes Simplex Virus VP22 tegument protein, its analogues, derivatives and variants (Elliott, G. and O'Hare, P., Gene Ther. 6:12-21 (1999); Derer, W. et al., J. Mol. Med. 77:609-613 (1999)). VP22, encoded by the UL49 gene, is a structural component of the tegument compartment of the HSV virus. A composition containing the C-terminal amino acids 159-301 of HSV VP22 protein is capable of translocating different types of cargoes into cells. Translocating activity is observed with a minimal sequence of DAATATRGRSAASRPTERPRA-PARSASRPRRPVE (SEQ ID NO: 18). Homologues of VP22 found in herpes viruses are also capable of delivery of attached compounds of interest across cell membranes (Harms, J. S. et al., J. Virol. 74:3301-3312 (2000); Dorange, F. et al., J. Gen. Virol. 81:2219-2230 (2000), which are incorporated herein in their entirety by reference).

In another embodiment the present invention, the cell penetrating peptides comprise cationic peptides with membrane translocation activity. Cationic amino acids include for example, but are not limited to, arginine, lysine, and ornithine. Active peptides with arginine rich sequences are present in the Grb2 binding protein, having the sequence RRWRRWWRRWWRRWRR (SEQ ID NO: 19) (Williams, E. J. et al., J. Biol. Chem. 272:22349-22354 (1997)) and polyarginine heptapeptide RRRRRRR (7R) (SEQ ID NO: 20) (Chen, L. et al., Chem. Biol. 8:1123-1129 (2001); Futaki, S. et al., J. Biol. Chem. 276:5836-5840 (2001); and Rothbard, J. B. et al., Nat. Med. 6(11):1253-7 (2000) which are incorporated herein in their entirety by reference). An exemplary cell penetrating peptide of this type has the sequence RPKKRKVRRR (SEQ ID NO: 21), which is found to penetrate the membranes of a variety of cell types. Also useful are branched cationic peptides capable of translocation across membranes, including by way of example and not limitation, $(KKKK)_2GGC$ (SEQ ID NO:22), $(KWKK)_2GCC$ (SEQ ID NO: 23), and $(RWRR)_2GGC$ (SEQ ID NO: 24) (Plank, C. et al., Human Gene Ther. 10:319-332 (1999) which are incorporated herein in their entirety by reference).

In a further embodiment, the cell penetrating peptides comprise chimeric sequences of cell penetrating peptides that are capable of translocating across cell membrane. An exemplary molecule of this type is transportan GALFLG-FLGGAAGSTMGAWSQPKSKRKV (SEQ ID NO:25), a chimeric peptide derived from the first twelve amino acids of galanin and a 14 amino acid sequence from mastoporan (Pooga, M et al., Nature Biotechnol. 16:857-861 (1998). Analogues of transportans are described in Soomets, U. et al., Biochim Biophys Acta. 1467(1): 165-76 (2000) and Lindgren, M. et al. Bioconjug Chem. 11 (5):619-26 (2000).

An exemplary deletion analogue, transportan-10, has the sequence AGYLLGKINLKALAALAKKIL (SEQ ID NO: 26).

Other types of cell penetrating peptides are the VT5 sequences DPKGDPKGVTVTVTVTVTGKGDPKPD (SEQ ID NO: 27), which is an amphipathic, beta-sheet forming peptide (Oehlke, J., FEBS Lett. 415(2):196-9 (1997); unstructured peptides described in Oehlke J., Biochim Biophys Acta. 1330(1):50-60 (1997); alpha helical amphipatic peptide with the sequence KLALKLALKAL-KAALKLA (SEQ ID NO: 28) (Oehlke, J. et al., Biochim Biophys Acta. 1414(1-2):127-39 (1998); sequences based on murine cell adhesion molecule vascular endothelial cadherin, amino acids 615-632 LLIILRRRIRKQAHAHSK (SEQ ID NO: 29) (Elmquist, A. et al., Exp Cell Res. 269(2):237-44 (2001); sequences based on third helix of the islet 1 gene enhancer protein RVIRVWFQNKRCKDKK (SEQ ID NO: 30) (Kilk, K. et al., Bioconjug. Chem. 12(6):911-6 (2001)); amphipathic peptide carrier Pep-1 KETWWETWWTEWSQPKKKRKV (SEQ ID NO: 31) (Morris, M. C. et al., Nat. Biotechnol. 19(12):1173-6 (2001)); and the amino terminal sequence of mouse prion protein MANLGYWLLALFVTMWTDVGLCKKRPKP (SEQ ID NO: 32) (Lundberg, P. et al., Biochem. Biophys. Res. Commun. 299(1):85-90 (2002)). In some embodiments, the cell penetrating peptides are variants, fragments of derivatives of SEQ ID NOS: 17 to 32.

In some embodiments of the present invention, a cell penetrating agent does not comprise amino acids. In such an embodiment, the cell penetrating agents is a small molecule or comprises polymers of subunits other than amino acids. For example such subunits can include, but are not limited to, hydroxy amino acids, N-methyl-amino acids amino aldehydes, and the like, which result in polymers with reduced peptide bonds. Other subunit types can be used, depending on the nature of the selected backbone. A variety of backbone types can be used to order and position the sidechain guanidino and/or amidino moieties, such as alkyl backbone moieties joined by thioethers or sulfonyl groups, hydroxy acid esters (equivalent to replacing amide linkages with ester linkages), replacing the alpha carbon with nitrogen to form an aza analog, alkyl backbone moieties joined by carbamate groups, polyethyleneimines (PEIs), and amino aldehydes, which result in polymers composed of secondary amines.

A more detailed backbone list includes N-substituted amide (CONR replaces CONH linkages), esters ($CO_2$), ketomethylene ($COCH_2$) reduced or methyleneamino ($CH_2NH$), thioamide (CSNH), phosphinate ($PO_2RCH_2$), phosphonamidate and phosphonamidate ester ($PO_2RNH$), retropeptide (NHCO), transalkene (CR=CH), fluoroalkene (CF=CH), dimethylene ($CH_22CH_2$), thioether ($CH_2S$), hydroxyethylene ($CH(OH)CH_2$), methyleneoxy ($CH_2O$), tetrazole ($CN_24$), retrothioamide (NHCS), retroreduced ($NHCH_2$), sulfonamido ($SO_2NH$), methylenesulfonamido ($CHRSO_2NH$), retrosulfonamide ($NHSO_2$), and peptoids (N-substituted glycines), and backbones with malonate and/or gem-diaminoalkyl subunits, for example, as reviewed by Fletcher et al. (1998) and detailed by references cited therein. Peptoid backbones (N-substituted glycines) can also be used. Many of the foregoing substitutions result in approximately isosteric polymer backbones relative to backbones formed from α-amino acids.

Polymers are constructed by any method known in the art. Exemplary peptide polymers can be produced synthetically, preferably using a peptide synthesizer (Applied Biosystems Model 433) or can be synthesized recombinantly by methods well known in the art.

Alternatively, peptides and polypeptides of the present invention, for example targeting agents, for example RVG peptide or cell permeable peptides can be obtained directly by chemical synthesis, e.g., using a commercial peptide synthesizer according to vendor's instructions. Methods and materials for chemical synthesis of polypeptides are well known in the art. See, e.g., Merrifield, 1963, "Solid Phase Synthesis," J. Am. Chem. Soc. 83:2149-2154.

A peptide of the present invention, for example RVG peptide or cell permeable peptides can be introduced into a cell using conventional techniques for transporting proteins into intact cells. In some embodiments, the RVG peptide is conjugated to a cell permeable protein by fusion as discussed herein, and in some embodiments the conjugate is further fused to an internalization peptide sequence, for example an internalization sequence derived from Antennapedia (Bonfanti et al., Cancer Res. 57:1442-1446) or to a nuclear localization protein such as HIV TAT peptide (U.S. Pat. No. 5,652,122, which is specifically incorporated herein in its entirety by reference).

Alternatively, the polypeptides of the present invention, for example an RVG peptide and/or a cell permeable peptide can be expressed in the cell following introduction of a DNA encoding the protein, e.g., a nucleic acid encoding the RVG peptide and/or cell permeable protein. In some embodiments, the nucleic acid comprises the nucleic acid sequence encoding an RVG peptide and a nucleic acid sequence encoding a cell permeable protein, for example to generate an RVG peptide-cell permeable protein fusion protein. In such embodiments, conventional expression vectors are useful in the methods of as described herein, and in some embodiments the subject can be administered the cells expressing the nucleic acid, or the nucleic acids can be administered directly to the subject by means commonly known in the art, for example by using a catheter.

In some embodiments, the peptides or peptide constructs as described herein, for example an RVG peptide and/or a cell permeable peptide or derivatives thereof, are cleavable peptides. A cleavable peptide is a peptide comprising an amino acid sequence that is recognized by a protease or peptidase or other cleaving agent present in a cell, for example a target cell, or found in surrounding tissue, or produced by a microbe capable of establishing an infection in a mammal.

Peptides that are cleavable typically have, but are not required to comprise one or more amino acids in addition to the amino acid recognition sequence; for example additional amino acids at the amino- or carboxy terminal, or both, ends of the recognition sequence. Means of adding amino acids to an amino acid sequence, e.g., in an automated peptide synthesizer, as well as means of detecting cleavage of a peptide, e.g., by chromatographic analysis for the amino acid products of such cleavage, are well known to ordinarily skilled artisans given the teachings of this invention. Peptide recognition sequences typically range from about 2 to 20 amino acids in length, and are typically located between the two fragments of the peptide to be cleaved, for example but not limited to, an RVG peptide and a cell permeable peptide.

The peptides or polypeptides useful in the present invention, for example RVG peptide and/or a cell permeable peptide or derivatives thereof can be modified at their amino termini, for example, so as to increase their hydrophilicity. Increased hydrophilicity enhances exposure of the peptides on the surfaces of lipid-based carriers into which the parent peptide-lipid conjugates have been incorporated. Polar groups suitable for attachment to peptides so as to increase their hydrophilicity are well known, and include, for example and without limitation: acetyl ("Ac"), 3-cyclohexylalanyl ("Cha"), acetyl-serine ("Ac Ser"), acetyl-seryl-serine ("Ac-Ser-Ser-"), succinyl ("Suc"), succinyl-serine ("Suc-Ser"), succinyl-seryl-serine ("Suc-Ser-Ser"), methoxy succinyl ("MeO-Suc"), methoxy succinyl-serine ("MeO-Suc-Ser"), methoxy succinyl-seryl-serine ("MeO-Suc-Ser-Ser") and seryl-serine ("Ser-Ser-") groups, polyethylene glycol ("PEG"), polyacrylamide, polyacrylomorpholine, polyvinylpyrrolidine, a polyhydroxyl group and carboxy sugars, e.g., lactobionic, N-acetyl neuraminic and sialic acids, groups. The carboxy groups of these sugars would be linked to the N-terminus of the peptide via an amide linkage. Presently, the preferred N-terminal modification is a methoxy-succinyl modification.

It will be appreciated that peptides often contain amino acids other than the 20 amino acids commonly referred to as the 20 naturally occurring amino acids, and many amino acids, including the terminal amino acids, can be modified either by natural processes such as glycosylation and other post-translational modifications, or by chemical modification techniques which are well known in the art. Even the common modifications that occur naturally in polypeptides are too numerous to list exhaustively here, but they are well described in basic texts and in more detailed monographs, as well as in a voluminous research literature, and they are well known to those of skill in the art. Among the known modifications which can be present in polypeptides of the present invention are, to name an illustrative few, acetylation, acylation, ADP-ribosylation, amidation, covalent attachment of flavin, covalent attachment of a heme moiety, covalent attachment of a polynucleotide or polynucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance, l. E. Creighton, Proteins-Structure and Molecular Properties, 2nd Ed., W.H. Freeman and Company, New York, 1993. Many detailed reviews are available on this subject, such as, for example, those provided by Wold, F., in Posttranslational Covalent Modification of Proteins, B. C. Johnson, Ed., Academic Press, New York, pp 1-12, 1983; Sifter et al., Meth. Enzymol. 182: 626-646, 1990 and Rattan et al., Protein Synthesis: Posttranslational Modifications and Aging, Ann. N.Y. Acad. Sci. 663: 48-62, 1992.

It will also be appreciated, as is well known and as noted above, that peptides and polypeptides are not always entirely linear. For instance, polypeptides can be branched as a result of ubiquitination, and they can be circular, with or without branching, generally as a result of posttranslational events, including natural processing events and events brought about by human manipulation which do not occur naturally. Circular, branched and branched circular polypeptides can be synthesized by non translational natural processes and by entirely synthetic methods.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and; synthetic polypeptides and such modifications can be present in polypeptides of the present invention, as well. For instance, the amino terminal residue of polypeptides made in E. coli, prior to proteolytic processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as E. coli. Accordingly, when glycosylation is desired, a polypeptide should be expressed in a glycosylation host, generally a eukaryotic cell. Insect cells often carry out the same posttranslational glycosylation as mammalian cells and, for this reason, insect cell expression systems have been developed to efficiently express mammalian proteins having native patterns of glycosylation, inter alia. Similar considerations apply to other modifications.

It will be appreciated that the same type of modification can be present to the same or varying degree at several sites in a given polypeptide. Also, a given peptide or polypeptide can contain many types of modifications.

In some embodiments, N-methyl and hydroxy-amino acids can be substituted for conventional amino acids in solid phase peptide synthesis. However, production of polymers with reduced peptide bonds requires synthesis of the dimmer of amino acids containing the reduced peptide bond. Such dimers are incorporated into polymers using standard solid phase synthesis procedures. Other synthesis procedures are well known in the art.

Effector Agents

The present invention provides a method to deliver effector agents across the blood brain barrier using, for example, an RVG peptide or variant thereof. Effector agents delivered by this approach can include, for example but not limited to, therapeutic agents, diagnostic agents and imaging agents among others.

In some embodiments, an RVG peptide is conjugated to a carrier particle, and an effector agent is associated with the carrier particle. In some embodiments, the carrier particle is a cell permeable agent (for example but not limited to a polymeric arginine residue of varying lengths such as 9R or 11R as disclosed herein or TAT), and in alternative embodiments a carrier particle is for example, a liposomal or polymeric nanoparticles such as a liposome. In some embodiments, where the carrier particle is for example a liposome, the carrier particle can further comprise cell permeable agents and/or targeting agents.

An "effector agent" as used herein refers to an agent that is transported by the carrier particle and targeting agent (i.e. an RVG peptide) across the BBB. An effector agent can be a chemical molecule of synthetic or biological origin. In some embodiments, an effector agent is generally a molecule that can be used in a pharmaceutical composition, for example the effector agent is a therapeutic agent. An effector agent as used herein also refers to any chemical entity or biological product, or combination of chemical entities or biological products, administered to a subject to treat or prevent or control a disease or condition, and are herein referred to as "therapeutic agents".

In alternative embodiments, an effector agents can be a chemical entity or biological product, or combination of chemical entities or biological products, administered to a subject for imaging purposes in the subject, for example to monitor the presence or progression of disease or condition, and are herein referred to as "imaging agents" or "diagnostic agents".

A chemical entity or biological product as disclosed herein is preferably, but not necessarily a low molecular weight compound, but can also be a larger compound, or any organic or inorganic molecule, including modified and unmodified nucleic acids such as antisense nucleic acids, RNAi, such as siRNA, shRNA, miRNA, nucleic acid analogues, miRNA analogues, antigomirs, peptides, peptidomimetics, avimers, receptors, ligands, and antibodies, aptamers, polypeptides or analogues, derivatives or variants thereof. For example, oligomers of nucleic acids, amino acids, carbohydrates include without limitation proteins, oligonucleotides, ribozymes, DNAzymes, glycoproteins, siRNAs, lipoproteins, aptamers, and modifications, derivatives and combinations thereof A therapeutic agent is an agent useful in the treatment of a disease, disorder or malignancy. In some embodiments, the disease, disorder or malignancy is a central nervous system (CNS) disorder, for example but not limited to a neurodegenerative disease. In some embodiment, the disease or disorder is associated with cells expressing the acetylcholine receptor.

As used herein, the terms "treating" or "treatment" of a disease include preventing the disease, i.e. preventing clinical symptoms of the disease in a subject that can be exposed to, or predisposed to, the disease, but does not yet experience or display a symptom of the disease; inhibiting the disease, i.e., arresting the development of the disease or a clinical symptom of the disease; or relieving the disease, i.e., causing regression of the disease or a clinical symptom of the disease.

Effector agents useful in the present invention include, for example effector agents for the treatment of diseases associated with cells expressing the α subunit of the acetylcholine receptor, e.g., cells protected by the BBB, e.g., neuronal cells, e.g., brain cancer cells. Useful therapeutic agents include nucleic acids such as siRNA, small molecule drugs, peptides. More than one therapeutic agent can be delivered by the delivery agent of the present invention.

Effector agents delivered by the compositions and methods of the present invention include siRNAs targeting viruses infecting neuronal cells, such as siRNAs targeting flaviviruses, e.g., Japanese encephalitis virus, (see U.S. Prov. Appl. 60/723,686 and Kumar et al. PLoS Med. 2006 April; 3(4):e96) which are incorporated herein in their entirety by reference, siRNAs targeting herpesviruses, e.g., HSV-1, HSV-2, varicella zoster virus (see U.S. Prov. Appl. 60/687, 216 and Palliser et al., 2006, Nature 439, 89-94) which are incorporated herein in their entirety by reference. In one embodiment, the siRNAs targeting herpesvirus target the latency associated transcript (e.g., GenBank Accession no. M17921).

Effector agents delivered by the composition and methods as disclosed herein include therapeutic agents for prevention and/or treatment of brain tumors. For example, RNAi-induced down-regulation of the oncogenic EGFR can serve as an effective therapy for brain tumors [37]. A significant (~50%) decline in the growth of intracranial gliomas also has been attained by RNAi-mediated knockdown of proteases, such as the receptor-bound urokinase plasminogen activator, cathepsin B, or matrix metalloprotease-9, which enable tumor progression [36,87]. Complete regression of the tumor growth was achieved with osmotic minipump-aided intratumoral infusion of a combination of shRNAs.

Effector agents for the treatment of neuronal diseases can be delivered by the methods as disclosed herein to treat, for example, neurological disorders and neurodegenerative disease for example but not limited to, Alzheimer's disease, Parkinson's disease, Huntington's disease, A.L.S., multiple sclerosis, neuro-AIDS, brain cancer, stroke, brain injury, spinal cord injury, autism, lysosomal storage disorders, fragile X syndrome, inherited mental retardation, inherited ataxias, blindness, paralysis, stroke, traumatic brain injury and spinal cord injury.

Effector agents delivered by the methods as disclosed herein include small molecules chemical and peptides to block intracellular signaling cascades, enzymes (kinases), proteasome function, lipid metabolism, cell cycle and membrane trafficking Agents delivered by the methods of the present invention include agents that promote neuronal growth, e.g., axonal outgrowth. Such therapeutic agents can be useful in the treatment of neuronal injury, e.g., spinal cord injury, stroke and traumatic brain injury.

A wide variety of therapeutic agents are available and are encompassed for use as effector agents, for example but not limited to: protein neurotrophic factors (for example, nerve growth factor) to treat brain injury, neurological diseases or disorders and neurodegenerative diseases; enzymes to replace enzymatic activities lost through genetic defects where the loss causes severe metabolic storage diseases such as Tay-Sachs disease; neurotransmitters and neuromodulators, such as dopamine and β-endorphin, that would be useful for treating Parkinson's disease and intractable pain, respectively, or conditions including disorders of movement, cognition, and behavior: antibiotics for treating infectious diseases, such as neurosyphilis or AIDS, where penetration into the brain of systemically administered antibiotics is presently a block to treatment; chemotherapeutic agents for treating brain tumors with agents that do not reach the tumor in sufficient amounts when tolerable doses are administered systemically; and diagnostic agents, such as specific contrast media for brain imaging, that are currently not used because of poor penetration into the brain upon systemic administration.

Further exemplary therapeutic agents useful in the methods as described herein include for example, but are not limited to; various neurotrophic factors, growth factors, or neurite inhibitory factors that can help prevent or repair various forms of neuronal damage caused by CNS disorders such as neurodegenerative diseases, or by ischemic or hypoxic crises such as stroke, cardiac arrest, suffocation, blood loss, or other types of physical injury or trauma. In some embodiments, therapeutic agents are also various neurotrophic hormones, growth factors, or neurite inhibitory factors that can help stimulate the formation of new synaptic connections between existing neurons and/or guide the outgrowth of neuronal processes to facilitate some connections and discourage others. In some subjects, this type of treatment can help facilitate the recovery of nervous function lost due to aging or various diseases. It can also help subjects regain muscular, speech, and other functions after a stroke, head injury, or other ischemic, hypoxic, excitotoxic, or similar crisis.

In further embodiments, therapeutic agents for use as effector agents can include various types of endocrine, paracrine, and related or similar polypeptides that can help treat various glandular, growth-related, maturation-related, sexual, and other disorders. Effector agents can be, for example, polypeptides that increase the quantities of certain neurotransmitter molecules inside the BBB to treat various neurodegenerative diseases. For example, polypeptides that can increase dopamine levels inside the brain (by acting as enzymes, hormones, or release factors, or through various other mechanisms) can be used to treat Parkinson's disease. Alternately, polypeptides that can increase acetylcholine levels can be useful for treating Alzheimer's disease.

In some embodiments of the present invention, effector agents, for example therapeutic agents can be any desired entity, e.g. polypeptide, polynucleotide, chemical compound, growth factor, hormone, antibody, cytokine, or the like including entities that cannot pass across the blood-brain barrier by themselves.

Usually, an agent that is a therapeutic agent is useful for treating neuronal cells or other target cells associated with any neurologically related disorder. For example, an effector agent to be delivered by the compositions and methods as disclosed herein can be a pharmaceutically active agent or a combination thereof that at least as part of its action targets the central nervous system, olfactory, visual system, or any other system associated with neurologically related disorders.

Examples of such therapeutic agents useful as effector agents are, but are not limited to neurotrophic factor including, without any limitation, nerve growth factor (NGF), ciliary neurotrophic factor (CNTF), brain-derived neurotrophic factor (DNTF), and glial-derived neurotrophic factor (GDNF). In another embodiment, effector agent useful to be delivered by the compositions and methods as disclosed herein include, without limitation cardiotrophin-1 (CT1), insulin-like growth factor-1 (IGF1), transforming growth factor-32 (TGF-32), epidermal growth factor (EGF), fibroblast growth factor (FGF), vascular endothelial growth factor (VEGF) and interferon α.

In yet another embodiment, the effector agents useful in the methods as disclosed herein are for example, insulin, glia-derived nexin, gangliosides, phosphatylserine, extracellular matrix remodeling enzymes and their inhibitors, integrins and their ligands, nerve toxins, nerve transmitters, protein chaperones, or protease inhibitors, e.g. serine protease inhibitors such as 4-(2-aminoethyl)-benzenesulfonyl fluoride (AEBSF) and horseradish-peroxidase (HRP).

In another embodiment, the effector agent, for example a siRNA therapeutic agent as disclosed herein can be prepared to be delivered in a "prodrug" form. The term "prodrug" indicates a therapeutic agent that is prepared in an inactive form that is converted to an active form (i.e., drug) within the body or cells thereof by the action of endogenous enzymes or other chemicals and/or conditions.

According to the present invention, the effector agent of the present invention can be transported to various target cells or tissues. For example, the effector agent of the present invention can be transported to any nerve cell, e.g. nerve cell in the central nervous system, olfactory, or visual system. The effector agent of the present invention can also be transported to a neurologically related target cell or tissue, e.g. cells or tissues that interact with or are targets of the nervous system.

In some embodiments, the therapeutic agents useful as effector agents are cytotoxic or growth-suppressing polypeptides that can be used inside the BBB to treat certain types of cancer or other diseases. Therapeutic agents useful in the present invention include, for example, various types of receptor antagonists, antibodies, and other polypeptides that can block or suppress one or more types of neuronal activity and can be used to help control and reduce neuropathic pain, hyperalgesia, and similar problems.

In some embodiments, lysosomal storage diseases due to lack of a particular polypeptide in the CNS can be treated by delivery of an agent comprising that polypeptide or a mimetic thereof into the CNS by the methods of the present invention.

In further embodiments, infections of the CNS by viruses, prions, or bacteria can be treated by delivering into the CNS effector agents that help control or reduce the spread of the infection. For example, delivery of effector agents comprising polypeptides that bind to the receptors and inhibit virus docking and/or viral transport can be able to reduce the spread of viruses, such as HIV or HSV within the CNS. Further embodiments include, for example, effector agents which are recombinant antibodies to antigens within the CNS that can be used to modulate physiological processes in a beneficial or useful way. For example, delivery of recombinant antibodies to myelin associated neurite inhibitory molecules such as No-Go can be able to enable regrowth and regeneration of CNS nerves, following spinal cord injury and other traumatic injuries.

In some embodiments, an effector agent is a therapeutic agent for the treatment of brain tumors and gliomas which can be delivered by the methods as described herein, for example such therapeutic agents are chemotherapy agents. The term "chemotherapeutic agent" or "chemotherapy agent" are used interchangeably herein and refers to an agent that can be used in the treatment of cancers and neoplasms, for example brain cancers and gliomas and that is capable of treating such a disorder. In some embodiments, a chemotherapeutic agent can be in the form of a prodrug which can be activated to a cytotoxic form. Chemotherapeutic agents are commonly known by persons of ordinary skill in the art and are encompassed for use in the present invention. For example, chemotherapeutic drugs for the treatment of brain tumors and gliomas include, but are not limited to: temozolomide (Temodar), procarbazine (Matulane), and lomustine (CCNU). Chemotherapy given intravenously (by IV, via needle inserted into a vein) includes vincristine (Oncovin or Vincasar PFS), cisplatin (Platinol), carmustine (BCNU, BiCNU), and carboplatin (Paraplatin), Mexotrexate (Rheumatrex or Trexall).

The term "effective amount" as used herein refers to the amount of therapeutic agent of pharmaceutical composition to alleviate at least some of the symptoms of the disease or disorder. The term "effective amount" includes within its meaning a sufficient amount of pharmacological composition to provide the desired effect. The exact amount required will vary depending on factors such as the type of tumor to be treated, the severity of the tumor, the drug resistance level of the tumor, the species being treated, the age and general condition of the subject, the mode of administration and so forth. Thus, it is not possible to specify the exact "effective amount". However, for any given case, an appropriate "effective amount" can be determined by one of ordinary skill in the art using only routine experimentation.

In one embodiment, the carrier particle is a liposomal or polymeric nanoparticles, for example a liposome. The therapeutic agents can be associated with nanoparticles such as liposomes by any method known to the skilled artisan, including encapsulation in the interior, association with the lipid portion of the molecule or association with the exterior of the liposome. Small molecule drugs soluble in aqueous solution can be encapsulated in the interior of the liposome. Small molecule drugs that are poor soluble in aqueous solution can associate with the lipid portion of the liposome. siRNAs can associate with the exterior of the liposome. siRNAs can be condensed with cationic polymers, e.g., PEI, or cationic peptides, e.g., protamines, and encapsulated in the interior of the liposome. Therapeutic peptides can be encapsulated in the interior of the liposome. In some embodiments, therapeutic peptides, and/or targeting agents, for example, transferrin, insulin like growth factor (IGF) and II and peptidomimetics and antibodies thereof can be covalently attached to the exterior of the liposome.

In one embodiment, an effector agent is a nucleic acid, e.g., plasmid, DNA, shRNA, miRNA, stRNA, siRNA, miRNA mimetic or antigomir. In such embodiments where the effector agent is a nucleic acid, the carrier particles associated with the effector agent can be liposomal or polymeric nanoparticles such as a liposome or in some embodiments the carrier particle is a peptide, for example, TAT, or an polymeric arginine peptide of varying length, such as 11R or 9R as disclosed herein (Melikov et al., Cell Mol Life Sci. 2005; 62: 2739-49). Alternatively, carrier particles useful for transporting nucleic acid effector agents to the BBB include, for example protamines, liposomes and polymers. In another embodiment, the effector agent a siRNA and the carrier particle is a carrier protein such as an polymeric arginine peptide of varying length, such as 11R or 9R as disclosed herein.

In some embodiments, an effector agent, for example RNA interfering agent and the carrier particle are combined together prior to contacting a biological membrane. Combining the RNA interfering agent and the carrier particle results in an association of the effector agent and the carrier particle. In one embodiment, an RNA interfering agent and the carrier particle are directly linked together, and thus, linkers are not required for association of the effector agent, for example RNA interference molecule) with the carrier particle. In another embodiment, the RNA interfering agent and the carrier polymer are bound together via electrostatic bonding.

In some embodiments, the effector agent functions as an RNA interference molecule. The term "RNAi" as used herein refers to interfering RNA, or RNA interference molecules are nucleic acid molecules or analogues thereof for example RNA-based molecules that inhibit gene expression. RNAi refers to a means of selective post-transcriptional gene silencing. RNAi can result in the destruction of specific mRNA, or prevents the processing or translation of RNA, such as mRNA.

In some embodiments, an effector agent is a siRNA. The term "short interfering RNA" (siRNA), also referred to herein as "small interfering RNA" is defined as an agent which functions to inhibit expression of a target gene, e.g., by RNAi. An siRNA can be chemically synthesized, it can be produced by in vitro transcription, or it can be produced within a host cell. siRNA molecules can also be generated by cleavage of double stranded RNA, where one strand is identical to the message to be inactivated.

In one embodiment, an siRNA effector agent is a double stranded RNA (dsRNA) molecule of about 15, 16, 17, 18, 19, 20, 21, 22, 23, 24, 25, 26, 27, 28, or 30 nucleotides in length, preferably about 15 to about 28 nucleotides, more preferably about 19, 20, 21, 22, 23, 24, or 25 nucleotides in length, and more preferably about 19, 20, 21, 22, or 23 nucleotides in length, and can contain a 3' and/or 5' overhang on each strand having a length of about 1, 2, 3, 4, or 5 nucleotides. The length of the overhang is independent between the two strands, i.e., the length of the over hang on one strand is not dependent on the length of the overhang on the second strand. Preferably the siRNA is capable of promoting RNA interference through degradation or specific post-transcriptional gene silencing (PTGS) of the target messenger RNA (mRNA).

An siRNAs effector agent for use in the methods as disclosed herein also include small hairpin (also called stem loop) RNAs (shRNAs). In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow. These shRNAs can be contained in plasmids, retroviruses, and lentiviruses and expressed from, for example, the pol III U6 promoter, or another promoter (see, e.g., Stewart, et al. (2003) RNA April; 9(4):493-501, incorporated by reference herein in its entirety).

The term "shRNA" as used herein refers to short hairpin RNA which functions as RNAi and/or siRNA species but differs in that shRNA species are double stranded hairpin-like structure for increased stability.

In some embodiments, the effector agent is an avimer. Avimers are multi-domain proteins with binding and inhibiting properties and are comprised typically of multiple independent binding domains linked together, and as such creates avidity and improved affinity and specificity as compared to conventional single epitope binding proteins such as antibodies. In some embodiments, one can use an avimer that is a protein or polypeptide that can bind simultaneously to a single protein target and/or multiple protein targets, as known as multi-point attachment in the art. Avimers are useful as therapeutic agents which function son multiple drug targets simultaneously for the progenitor cell and/or treatment of multifactorial diseases or disorders, for example multifactorial neurodegenerative diseases or neurological disease.

In some embodiments, the effector agent is a antigomir. Antigomirs are oligonucleotides, for example synthetic oligonucleotides capable of gene silencing endogenous miRNAs.

The term "association" or "interaction" as used herein in reference to the association or interaction of an effector agent, e.g., siRNA, with a carrier particle, refers to any association between the effector agent, e.g., siRNA, with a carrier particle, e.g., a peptide carrier, either by a direct linkage or an indirect linkage. An indirect linkage includes an association between a effector agent, e.g., siRNA, and a carrier particle wherein said effector agent, e.g., siRNA, and said carrier particle are attached via a linker moiety, e.g., they are not directly linked. Linker moieties include, but are not limited to, e.g., nucleic acid linker molecules, e.g., biodegradable nucleic acid linker molecules. A nucleic acid linker molecule can be, for example, a dimer, trimer, tetramer, or longer nucleic acid molecule, for example an oligonucleotide of about 2, 3, 4, 5, 6, 7, 8, 9, 10, 11, 12, 13, 14, 15, 16, 17, 18, 19, 20, 21, 22, 23, 24, 25, or more nucleotides in length.

A direct linkage includes any linkage wherein a linker moiety is not required. In one embodiment, a direct linkage includes a chemical or a physical interaction wherein the two moieties, the therapeutic agent, e.g., siRNA, and the carrier particle, interact such that they are attracted to each other. Examples of direct interactions include non-covalent interactions, hydrophobic/hydrophilic, ionic (e.g., electrostatic, coulombic attraction, ion-dipole, charge-transfer), Van der Waals, or hydrogen bonding, and chemical bonding, including the formation of a covalent bond. Accordingly, in one embodiment, an effector agent, e.g., siRNA, and the carrier particle are not linked via a linker, e.g., they are directly linked. In a further embodiment, the therapeutic agent, e.g., siRNA, and the carrier particle are electrostatically associated with each other.

In some embodiments, the effector agent can be an imaging agent. In order to function as a suitable effector agent for medical imaging, the effector agent is useful in a molecular imaging diagnosis procedure, for example but not limited to, magnetic resonance (MR) imaging. Delivery of such effector agents using the methods and compositions as disclosed herein can enhance the imaging of CNS (i.e. brain and spinal cord) structures and function by MRI or PET for example. Contrast enhancement can be provided by gadolinium, for example, gadolinium in the form of Gd-DTPA-aminohexanoic acid. Other imaging agents are useful in the methods as disclosed herein include, for example other lanthanide ion coordination complexes can allow for even greater enhanced relaxation at higher field strength (Aime, S., et al., Chem. Soc. Rev. 27:19-29, 1998; Aime et al., J. Mannet. Reson. Iman. 16:394-406, 2002). Paramagnetic CES T agents are useful as imaging agents in the methods and compositions as disclosed herein, for example as $Eu^{+3}$, $Tb^{+3}$, $Dy^{+3}$, $Er^{+3}$, $Tm^{+3}$, or $Yb^{+3}$ alter tissue contrast via chemical exchange saturation transfer of presaturated spins to bulk I water (Elst, L. V., et al., Mann. Reson. Med. 47:1121-1130, 2002). In some embodiments, more than one imaging agent can be used simultaneously in the composition and methods of the present invention, with techniques available for attachment of multiple imaging agents, for example Gd-DTPA to proteins to enhance the MR signal known by persons of ordinary skill in the art. The T1 acceleration and contrast enhancement of Gd and especially Fe have been shown to saturate at very high field strength, however, while these other lanthanides do not, thus taking full advantage of the increased resolution of very high field strengths.

In some embodiments, an imaging effector agent is useful as diagnostic agent capable of detection in vivo following administration. Exemplary imaging effector agents useful for diagnostic purposes include electron dense material, magnetic resonance imaging agents, radiopharmaceuticals and fluorescent molecules. Radionucleotides useful for imaging include radioisotopes of copper, gallium, indium, rhenium, and technetium, including isotopes $^{64}Cu$, $^{67}Cu$, $^{111}In$, $^{99m}Tc$, $^{67}Ga$ or $^{68}Ga$. Imaging agents disclosed by Low et al. in U.S. Pat. No. 5,688,488, incorporated herein by reference, are also useful in the compositions as disclosed herein.

Accordingly in some embodiments, the methods as disclosed herein provides methods that are useful for diagnostic purposes, for example but not limited to visualization of plaques and other structures in the CNS of a subject, for example visualization of plaques in the brain of subject with Alzheimer's Disease. In further embodiments, the compositions and methods of the present invention are useful for monitoring the effect of a therapeutic intervention and/or for prognostic purposes. For example, in some embodiments the present invention can be used for monitoring the efficacy of a therapeutic treatment in a subject treated with a therapy for Alzheimer's Disease and monitoring the reduction of plaques in the subject brain.

Accordingly, as disclosed herein the method provides a means to deliver nucleic acids, such as siRNA, nucleic acids, nucleic acid analogues, miRNA, miRNA mimetics, antigomirs and the like to neuronal cells in vivo and in vivo. The methods as disclosed herein are useful for delivering effector agents to neuronal cells in vitro, in vivo or ex vivo for multiple purposes, such as (i) research purposes including but not limited to investigating or studying neuronal function and responses, increasing our understanding of neuronal survival, development, and response to agents as well as general neuronal function and neuronal toxicity assays, and (ii) therapeutic purposes.

Central Nervous System (CNS) Disorders

In some embodiments, the present invention provides methods to deliver effector agents across the blood brain barrier in a subject. In an alternative embodiment, the present invention provides methods to treat CNS disorders, the method comprising administering to a subject a composition comprising an effector agent, a targeting agent (for example, an RVG peptide or variant or fragment or derivative thereof) and a carrier particle, wherein the effector agent is associated with the carrier particle. Examples of carrier particles are for example, but not limited to cell permeable agents and various forms of liposomal or polymeric nanoparticles such as liposomes. Thus, the present invention provides methods to treat CNS disorders, such as neurological disorders and neurodegenerative diseases.

CNS disorders include disorders of the central nervous system as well as disorders of the peripheral nervous system. CNS disorders include, but are not limited such as neurological disorders, neurodegenerative diseases, brain and spinal cord injuries, cerebrovascular ischemia, neurodegenerative diseases, dementia, traumatic brain injury, stroke, post-stroke, post-traumatic brain injury, small-vessel cerebrovascular disease, and neurological disorders: for example pugilist, pain, neuropathy, neurotrauma, organophosphate poisoning, depression, schizophrenia, anxiety disorders, epilepsy and bipolar disorder and cognitive-related disorders such as dementia and memory loss.

Examples of neurodegenerative diseases useful to be treated by the method and compositions as disclosed herein include, for example but not limited to: amyotrophic lateral sclerosis (ALS), Parkinson's disease, Huntington's disease, Wilson's disease, multi-system atrophy, Alzheimer's disease, Pick's disease, Lewy-body disease, Hallervorden-Spatz disease, torsion dystonia, hereditary sensorimotor neuropathies (HMSN), Gerstmann-Skaussler-Schanker; disease, Creutzfeld-Jakob-disease, Machado-Joseph disease, Friedreich ataxia, Non-Friedreich ataxias, Gilles de la Tourette syndrome, familial tremors, olivopontocerebellar degenerations, paraneoplastic cerebral syndromes, hereditary spastic paraplegias, hereditary optic neuropathy (Leber), retinitis pigmentosa, Stargardt disease, and Kearns-Sayre syndrome.

Other neurodegenerative disorders include, for example e.g. Alpers' disease, Autosomal Dominant Neurodegenerative Disorder, Batten Disease, Cerebral calcinosis, Cockayne Syndrome, corticobasal ganglionic degeneration, Dementia with Lewy Bodies, Lewy Body Variant, Multiple System Atrophy, Neuronal inkanuclear inclusion disease, Olivopontocerebellar Atrophy, Postpoliomyelitis Syndrome, Progressive Supranuclear Palsy, Rett Syndrome, Shy-Drager Syndrome, Tauopathies, Tri-nucleotide repeat diseases, and Tuberous Sclerosis.

Further examples of neurodegenerative disorders, include for example cerebrovascular accidents (CVA), vascular-related dementia, bovine spongiform encephalopathy (BSE), multiple sclerosis (MS), peripheral disorders with a CNS component, such as septic shock, hepatic encephalopathy, (diabetic) hypertension, diabetic microangiopathy, sleeping sickness, Whipple disease, Duchenne muscular dystrophy (DMD) and (pre)eclampsia, neuropsychiatric disorders, such as depression, autism, anxiety attention deficit hyperactivity disorder (ADHD), bipolar disorder, schizophrenia and other psychoses.

Other CNS disorders include, for example brain tumors, epilepsy, migraine, narcolepsy, insomnia, chronic fatigue syndrome, mountain sickness, encephalitis, meningitis, AIDS-related dementia.

Parkinson's disease (which is classically characterized chiefly by depigmentation of the substantia nigra and by the presence of Lewy bodies) and Parkinsonian Syndromes (or Parkinsonian disorders) are useful to be treated by the method and compositions as disclosed herein. Parkinson's disease differs from other parkinsonian disorders based on clinicopathologic criteria. (Dauer and Przedborski (2003), Neuron, 39, 889-909). Examples of Parkinsonism syndromes include, for example but not limited to; Parkinson's disease, Secondary Parkinsonism, a familial neurodegenerative disease or a Parkinsonism plus syndrome. Classification of Parkinsonism is briefly, Primary (idiopathic) Parkinsonism-Parkinson's disease (sporadic, familial), Secondary (acquired, symptomatic) Parkinsonism-infectious (postencephalitic, slow virus), drug-induced (dopamine antagonists and depletors), Hemiatrophy (hemiparkinsonism), Hydrocephalus (normal pressure hydrocephalus), hypoxia, infectious (postencephalistis), metabolic (parathyroid dysfunction), toxin (MPTP, CO, Mn, Hg. CS2, methanol, ethanol), Trauma (pugilistic encephalopathy), tumor, and vascular (multinfarct state), Heredodegenerative Parkinsonism-Huntington's disease, Wilson's disease, Hallervorden-Spatz disease, Olivopontocerebellar and spinocerebeller degenerations, neuroacanthocytosis, Lubag (X-linked dystonia-parkinsonism), and mitochondrial cytopathies with stratial necrosis Multiple system degenerations (parkinsonism plus)—Cortical-basal ganglionic degeneration, Dementia syndromes (Alzheimer's diseases, diffuse Lewy body disease, frontotemporal dementia), Lytico-Bodig (Guamanian Parkinsonism-dementia-ALS), Multiple system atrophy syndromes (striatonigral degeneration, Shy-Drager syndrome, sporadic olivopontocerebellar degeneration (OPAC), motor neuron disease parkinsonism), Progressive pallidal atrophy, and progressive supranuclear palsy.

The methods and compositions as disclosed herein are also useful in the treatment of dementias, for example but not limited to, vascular dementia, dementia with Lewy bodies, frontotemporal dementia and Parkinsonism linked to chromosome 17, front and temporal dementias, progressive nuclear palsy, corticobasal degeneration, Huntington's disease, thalamic degeneration, Creutzfeldt-Jakob dementia, HIV dementia, schizophrenia with dementia, and Korsakoff s psychosis.

Similarly, cognitive-related disorders, such as mild cognitive impairment, age-associated memory impairment, age-related cognitive decline, vascular cognitive impairment, attention deficit disorders (ADD), attention deficit hyperactivity disorders (ADHD), and memory disturbances in children with reaming disabilities can be treated using the methods and compositions as disclosed herein.

The methods and compositions as disclosed herein are also useful in treatment of depression. Depression is characterized by sadness, loss of interest in activities, and decreased energy. Other symptoms include loss of confidence and self-esteem, inappropriate guilt, thoughts of death and suicide, diminished concentration, and disturbance of sleep and appetite. A variety of somatic symptoms can also be present. Though depressive feelings are common, especially after experiencing setbacks in life, depressive disorder is diagnosed only when the symptoms reach a threshold and last at least two weeks. Depression can vary in severity from mild to very severe, and includes polar (constant) and unipolar (mainic or bi-polar) depression, as well as seasonal affective disorder (SAD). Depression is typically characterized into eight basic dimensions i.e., Pessimism, Weak Concentration, Sleep Problems, Anhedonia, Fatigue, Loneliness, Low Self-esteem, and Somatic Complaints to define the profile of children's and adolescents' depression. Depression can occur as an idiopathic disease (with no somatic disease associated with it), or it can be a psychiatric symptom of a somatic disorder, especially a number of neurodegenerative disorders.

Depressive disorders (DDs) are frequent psychiatric comorbidities of neurological disorders like multiple sclerosis, stroke, dementia, migraine, Parkinson's disease, and epilepsy. The clinical manifestations of DDs in these neurological disorders are identical to those of idiopathic mood disorders, for example, Multiple Sclerosis, Traumatic brain injury, stroke: dementia, Alzheimer's disease, Migraine, Parkinson's disease, Epilepsy and Huntington's Disease.

In some embodiments, the methods and compositions as disclosed herein are also useful for modulating neuronal physiology by delivery of agents that alter the expression of neuropeptide genes, for example agents that act as agonists or antagonists or activate or inhibit genes, for example genes that (i) express polypeptides that can block and suppress pain (such as so-called "endorphins"); (ii) genes that express growth factors; (iii) genes that express polypeptides to promote regeneration or prolong the life-spans of cells; and genes express toxic polypeptides, such as to kill tumor cells In some embodiments, the methods and compositions as disclosed herein are also useful in the treatment of pain and pain disorders. Pain includes, for example, nociceptive pain (pain as a result of injury to bodily tissues), including inflammatory pain, allodynia, hyperallodynia, and neuropathic (pain as a result of abnormalities to nerves, spinal cord and brain), including phantom limb pain, post-therapeutic neuralgia. Pain can be acute or chronic pain, and also includes psychogenic pain (pain related to a physiological disorder). Nociceptive pain includes somatic and visceral pain (for example pancreatits, intestinal cystitis, dysmenorrheal, irritable Bowel syndrome, Crohn's disease, biliary colic, urethral colic, myocardial infarction and pain syndromes of the pelvic cavity, e.g., vulvodynia, orchialgia, urethral syndrome and protatodynia.). Neuropathic pain includes sympathetic pain. Pain can be associated with CNS disorders, for example, multiple sclerosis, spinal cord injury, sciatica, failed back surgery syndrome, traumatic brain injury, epilepsy, Parkinson's disease, post-stroke, and vascular lesions in the brain and spinal cord (e.g., infarct, hemorrhage, vascular malformation).

Neuropathic pain relates to pathological condition that affects neurons, in a manner that generates unwanted and excessive pain signals. This is often some anatomical reorganization of the nerve connections within the BBB, such that there is chronic or inappropriate pain response. The term "hyperalgesia" is also used, as a descriptive term that translates directly to "excessive pain" and the term "allodynia" is also used to refer to this condition. Neuropathic pain includes post mastectomy pain, "phantom limb" pain, reflex sympathetic dystrophy (RSD), trigeminal neuralgia-radioculopathy, post-surgical pain, HIV/AIDS related pain, cancer pain, metabolic neuropathies (e.g., diabetic neuropathy, vasculitic neuropathy secondary to connective tissue disease), paraneoplastic polyneuropathy associated, for example, with carcinoma of lung, or leukemia, or lymphoma, or carcinoma of prostate, colon or stomach, trigeminal neuralgia, diabetic neuropathy, cranial neuralgias, and post-herpetic neuralgia, arachnoiditis, post-infective pain (such as outbreaks of "shingles", caused by herpes zoster virus and lingering chronic pain that arises after a traumatic injury. Pain associated with peripheral nerve damage, central pain (i.e. due to cerebral ischemia) and various chronic pain i.e. lumbago, back pain (low back pain), sciatica inflammatory and/or rheumatic pain. Headache pain (for example, migraine with aura, migraine without aura, and other migraine disorders), episodic and chronic tension-type headache, tension-type like headache, cluster headache, and chronic paroxysmal hemicrania. Causalgia is another type of neuropathic pain well as other types of neuropathic pain are well known by persons of skill in the art Neuropathic pain can range over a very wide span of intensity and starting at annoying up to excruciating, debilitating and unbearable.

In some embodiments, the methods and compositions as disclosed herein useful for treating some cases of learning or memory dysfunction, for example, such as occur in aging, dementia, after brain trauma or injury, and after various types of major surgery, especially surgery involving a cardiopulmonary bypass machine.

In further embodiments, the methods and compositions as disclosed herein useful for treating disorders due to excitotoxic damage of neurons, or resulting from diseases or injuries that involve ischemia (inadequate blood flow, as occurs during a stroke or cardiac arrest) or hypoxia (inadequate oxygen supply, as occurs during drowning, carbon monoxide poisoning, etc.) or traumatic head injury. For example, in animal studies NGF infusion can slow or reverse the retrograde atrophy of cholinergic cell bodies and fiber networks and other changes in the cholinergic system that are caused by infarction or measured by infarct volumes or severity (e.g., Cuello et al 1992). Administration of NGF (or induction of NGF synthesis in viva by clenbuterol) has been shown to reduce infarct volume in rat models of permanent middle cerebral artery occlusion (Semkova et al 1999). Other animal data indicates that NGF is able to act after a brain insult to block progression of neuronal damage (e.g., Guegan et al 1998). Accordingly, by delivering agents, for example NGF to the BBB after a stroke or other brain injury or insult, it likely will be able to reduce the extent and severity of subsequent neuronal loss.

In some embodiments, the methods and compositions as disclosed herein are also useful to treat pathogen infections of the brain and spinal cord, for example but not limited to pathogen is Meningococci (*Neisseria meningitidis*) can cause infection of the layers covering the brain and spinal cord (meningitis).

In some embodiments, the methods and compositions as disclosed herein are also useful in treatment of neurological and psychiatric diseases associated with neural cell death include septic shock, intracerebral bleeding, subarachnoidal hemorrhage, multiinfarct dementia, inflammatory diseases (such as vasculitis, multiple sclerosis, and Guillain-Barre-; syndrome), neurotrauma, peripheral neuropathies, polyneuropathies, epilepsies, schizophrenia, depression, metabolic encephalopathies, and infections of the central nervous system (viral, bacterial, fungal).

In yet another embodiment, the methods and compositions as disclosed herein are also useful to treat disorders where the tissue affected is in contact with neurons and/or the CNS, for example Anterior Horn Diseases including Poliomyelitis, Spinal Muscular Atrophy (e.g. Werding-Hoffman), Muscle Disorders, (e.g. Muscular Dystrophies including Duchene dystrophy, Becker dystrophy, Limb Girdle dystrophy, Congenital Dystrophy, Facioscapulohumeral dystrophy, Distal dystrophy, and Oculopharyngeal dystrophy, Necrotizing Myopathies including Polymyositis, and Dermatomyositis, Metabolic Myopathies including Malignant Hyperthermia, Mitochondrial Myopathies, Myotonic Disorders, and Congenital Myopathies), diseases of the Neuromuscular Junction, (e.g. Myasthenia Gravis, and Eaton-Lambert Syndrome), diseases of the Peripheral Nerve, (e.g. Metabolic Neuropathies including Diabetes Mellitus, Vitamin deficiency, Uremia, and Porphyria, Toxic Neuropathies including alcohol, vincristine, isoniazid, arsenic, lead, hexane, hexachlorophene, acrylamide, and triethyltin, Vasculitic Neuropathies including Polyarteritis nodosa, Churg-Strauss Syndrome, and Rheumatoid artritis, Inflammatory Neuropathies including Guillain-Barre and Chronic Inflammatory demyelinating neuropathy, Hypertrophic Neuropathies including Charcot-Marie-Tooth Disease, Dejerine-Sottas Neuropathy, and Refsum's Disease, Genetic Neuropathies including the various forms of leukodystrophy, Ataxia-telangiectasia and Giant Axonal Neuropathy, Infectious Neuropathies including Herpes Zoster Neuritis, Herpes Simplex, and Leprosy, Diabetic Neuropathies including Distal symmetrical primarily sensory neuropathy, Autonomic Neuropathy, Proximal asymmetrical painful primary neuropathy, and Cranial mononeuropathy.

In other embodiments, the methods of the present invention are also useful to treat CNS disorders where the CNS disorder is a tumor or cancer. Tumors or cancers of the brain are referred to as a brain tumor or cancer, glioma or oligodenrogliomia and are included as CNS disorders herein.

The term "brain tumor" as used herein is any intracranial tumor created by abnormal and uncontrolled cell division, normally either found in the brain itself (neurons, glial cells (astrocytes, oligodendrocytes, ependymal cells), lymphatic tissue, blood vessels), in the cranial nerves (myelin-producing Schwann cells), in the brain envelopes (meninges), skull, pituitary and pineal gland, or spread from cancers primarily located in other organs (metastatic tumors). Primary (true) brain tumors are commonly located in the posterior cranial fossa in children and in the anterior two-thirds of the cerebral hemispheres in adults, although they can affect any part of the brain. Most primary brain tumors originate from glia (gliomas), astrocytes (astrocytomas), oligodendrocytes (oligodendrogliomas), or ependymal cells (ependymoma). There are also mixed forms, with both an astrocytic and an oligodendroglial cell component. These are called mixed gliomas or oligoastrocytomas. Additionally, mixed glioneuronal tumors (tumors displaying a neuronal, as well as a glial component, e.g. gangliogliomas, disembryoplastic neuroepithelial tumors) and tumors originating from neuronal cells (e.g. gangliocytoma, central gangliocytoma) can also be encountered.

Other varieties of primary brain tumors include: primitive neuroectodermal tumors (PNET, e.g. medulloblastoma, meningiomas, medulloepithelioma, neuroblastoma, retinoblastoma, ependymoblastoma), tumors of the pineal parenchyma (e.g. pineocytoma, pineoblastoma), ependymal cell tumors, choroid plexus tumors, neuroepithelial tumors of uncertain origin (e.g. gliomatosis cerebri, astroblastoma), etc. Another type of primary intracranial tumor is primary cerebral lymphoma, also known as primary CNS lymphoma, which is a type of non-Hodgkin's lymphoma.

As used herein, the term "glioma" refers to a tumor originating in the neuroglia of the brain or spinal cord. Gliomas are derived form the glial cell types such as astrocytes and oligodendrocytes, thus gliomas include astrocytomas and oligodendrogliomas, as well as anaplastic gliomas, glioblastomas, and ependymomas. Astrocytomas and ependymomas can occur in all areas of the brain and spinal cord in both children and adults.

In some embodiments, the present invention is useful for treating neurodegenerative disorders of the CNS (such as Alzheimer's disease), by delivering agents such as neurotrophic or neuroprotective factors to neurons at risk of degenerating. In some embodiments, delivery of effector agents, for example neurotrophic factors to target cells, is for example but not limited to the affected neurons. As a non-limiting example, where the treatment is for Alzheimer's Disease, the methods and compositions can be used to deliver effector agents, for example, to the basal forebrain cholinergic neurons in a subject having or at risk of developing Alzheimer's disease. Such a delivery of such therapeutic agents can slow, and potentially halt, the neurodegenerative process. In some embodiments, the methods and compositions as disclosed herein are useful for treating trauma or injury to the CNS (such as that which occurs in head injury), by delivering an effector agent such as a neuronal growth factor (such as neurotrophic factors) to the target cells, where the target cells are injured and surviving neurons. As an example, GDNF can be an effector agent which is delivered to target cells such as cortical motor neurons for treatment of subjects following stroke and/or head trauma and/or for the treatment of ALS.

In further embodiments, the present invention can be adapted to treatment of various types of CNS-related neurological disorders or deficiencies which are correlated with either too little or too much of some particular polypeptide. This can be accomplished by using this method to deliver an agent into BBB-protected CNS tissue, either: (i) an agent, for example a polypeptide which provides an additional quantity of a polypeptide, to reduce or eliminate a deficiency; or, (ii) an agent, for example an RNAi or polypeptide which blocks, antagonizes, or otherwise suppresses a certain molecule, receptor, or reaction, thereby helping to controlling a CNS disorder that is caused or characterized by too much of a particular molecule.

Therapeutic Administration

In one embodiment, the present invention provides a composition comprising a targeting agent, for example an RVG peptide and a carrier particle, wherein an effector agent is associated with the carrier particle. In some embodiments, the carrier particle is a liposomal or polymeric nanoparticles such as a liposome or a cell permeable agent. In some embodiments, the composition comprises an RVG peptide or fragment or variant thereof, and a carrier peptide and can further comprise a cell permeable agent.

In some embodiments, the composition comprises targeting agents, for example RVG peptides conjugated to carrier particles, and at least one effector agent. In some embodiments, where the composition comprises a plurality of targeting agents and carrier particles, there can be various different of targeting agents, which can be conjugated all to the same type of carrier particle, or different carrier particles. By way of a non-limiting example, the composition can comprise an RVG peptide as a targeting agent which is conjugated to a liposomal or polymeric nanoparticles such as a liposome carrier peptide, and the composition can also comprise another targeting agent-carrier particle conjugate comprising a transferrin peptide as the targeting agent and a polymeric arginine residue of various length, such as 9R or 11R as disclosed herein as the carrier peptide. In other words, the composition can comprise a plurality of targeting agent-carrier particle conjugates with effector agents associated with the carrier particles. Accordingly, in some embodiments the targeting agent and carrier particle of each targeting agent-carrier particle conjugate can be the same or different types of targeting agent and carrier particles respectively. In some embodiments, the composition comprises a plurality of targeting agents conjugated to a plurality of different types of carrier particles. In some embodiments, any combination of targeting agent can be used with any combination of carrier particle. Accordingly, depending on the carrier particles present in the composition will also determines the types of effector agents also in the composition. As a non-limiting example, if the composition comprises a targeting agent-carrier particle conjugate comprising a liposome carrier particle, the effector agent associated with the carrier particle can be, for example a small molecule, whereas in alternative embodiments, where the composition comprises a targeting agent-carrier particle conjugate comprising a peptide carrier particle, for example 9dR or 11dR, the effector agent associated with the carrier particle can be, for example a nucleic acid for example a RNAi.

In further embodiments where the composition comprises a plurality of targeting agents and carrier particles, the effector agent also present in the composition that is associated with the carrier particle can also be different. For instance, an effector agent associated with the carrier particle can be a different type of effector agent, for example nucleic acid effector agent or a peptide effector agent. In some embodiments, the effector agent can be different variant of the same type of effector agent, for example if the effector agent is a nucleic acid, the composition can comprise both RNA and DNA effector agents. In further embodiments, the composition can comprise a plurality of effector agents that are variants of the same type of agent, for example variants or derivatives of siRNA. By way of a non-limiting example, the composition can comprise a plurality of RNAi effector agents that associate with the carrier peptide, where the RNAi effector agents are different, for example the RNAi effector agent silences different gene targets or targets different regions on the same gene.

Compositions as disclosed herein wherein the carrier particle is a liposome or polymeric nanoparticle can be administered by any convenient route, including parenteral, enteral, mucosal, topical, e.g., subcutaneous, intravenous, topical, intramuscular, intraperitoneal, transdermal, rectal, vaginal, intranasal or intraocular. In one embodiment, the compositions as disclosed herein are not topically administered. In one embodiment, the delivery is by oral administration of the composition formulation. In one embodiment, the delivery is by intranasal administration of the composition, especially for use in therapy of the brain and related organs (e.g., meninges and spinal cord). Along these lines, intraocular administration is also possible. In another embodiment, the delivery means is by intravenous (i.v.) administration of the composition, which is especially advantageous when a longer-lasting i.v. formulation is desired. Suitable formulations can be found in Remington's Pharmaceutical Sciences, 16th and 18th Eds., Mack Publishing, Easton, Pa. (1980 and 1990), and Introduction to Pharmaceutical Dosage Forms, 4th Edition, Lea & Febiger, Philadelphia (1985), each of which is incorporated herein by reference.

The compositions as disclosed herein can be administered in prophylatically or therapeutically effective amounts. The targeted delivery compositions as disclosed herein can be administered along with a pharmaceutically acceptable carrier. A prophylatically or therapeutically effective amount means that amount necessary, at least partly, to attain the desired effect, or to delay the onset of, inhibit the progression of, or halt altogether, the onset or progression of the particular disease or disorder being treated. Such amounts will depend, of course, on the particular condition being treated, the severity of the condition and individual patient parameters including age, physical condition, size, weight and concurrent treatment. These factors are well known to those of ordinary skill in the art and can be addressed with no more than routine experimentation. It is preferred generally that a maximum dose be used, that is, the highest safe dose according to sound medical judgment. It will be understood by those of ordinary skill in the art, however, that a lower dose or tolerable dose can be administered for medical reasons, psychological reasons or for virtually any other reasons.

The terms "composition" or "pharmaceutical composition" are used interchangeably herein and refers to compositions or formulations that usually comprise an excipient, such as a pharmaceutically acceptable carrier that is conventional in the art and that is suitable for administration to mammals, and preferably humans or human cells. Such compositions can be specifically formulated for administration via one or more of a number of routes, including but not limited to, oral, parenteral, intravenous, intraarterial, subcutaneous, intranasal, sublingual, intraspinal, intracerebroventricular, and the like. Cells administered a composition as disclosed herein can be part of a subject, for example for therapeutic, diagnostic, or prophylactic purposes. The cells can also be cultured, for example cells as part of an assay for screening potential pharmaceutical compositions, and the cells can be part of a transgenic animal for research purposes. In addition, compositions for topical (e.g., oral mucosa, respiratory mucosa) and/or oral administration can form solutions, suspensions, tablets, pills, capsules, sustained-release formulations, oral rinses, or powders, as known in the art are described herein. The compositions also can include stabilizers and preservatives. For examples of carriers, stabilizers and adjuvants, University of the Sciences in Philadelphia (2005) *Remington: The Science and Practice of Pharmacy with Facts and Comparisons,* 21st Ed.

The "pharmaceutically acceptable carrier" means any pharmaceutically acceptable means to mix and/or deliver the targeted delivery composition to a subject. The term "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation and is compatible with administration to a subject, for example a human. For the clinical use of the methods of the present invention, targeted delivery composition of the invention is formulated into pharmaceutical compositions or pharmaceutical formulations for parenteral administration, e.g., intravenous; mucosal, e.g., intranasal; enteral, e.g., oral; topical, e.g., transdermal; ocular, e.g., via corneal scarification or other mode of administration. The pharmaceutical composition contains a compound of the invention in combination with one or more pharmaceutically acceptable ingredients. The carrier can be in the form of a solid, semi-solid or liquid diluent, cream or a capsule. These pharmaceutical preparations are a further object of the invention. Usually the amount of active compounds is between 0.1-95% by weight of the preparation, preferably between 0.2-20% by weight in preparations for parenteral use and preferably between 1 and 50% by weight in preparations for oral administration.

The term "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. The phrases "systemic administration," "administered systemically," "peripheral administration" and "administered peripherally" as used herein mean the administration of a compound, drug or other material other than directly into the central nervous system, such that it enters the animal's system and, thus, is subject to metabolism and other like processes, for example, subcutaneous administration.

As used herein, the terms "administering," and "introducing" are used interchangeably herein and refer to the placement of the pharmaceutical composition comprising the RVG peptide and associated agents of the present invention into a subject by a method or route which results in at least partial localization of the agents at a desired site. The agents of the present invention can be administered by any appropriate route which results in an effective treatment in the subject.

In the preparation of pharmaceutical formulations containing the targeted delivery composition of the present invention in the form of dosage units for oral administration the compound selected can be mixed with solid, powdered ingredients, such as lactose, saccharose, sorbitol, mannitol, starch, arnylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture is then processed into granules or pressed into tablets.

Soft gelatin capsules can be prepared with capsules containing a mixture of the active compound or compounds of the invention in vegetable oil, fat, or other suitable vehicle for soft gelatin capsules. Hard gelatin capsules can contain granules of the active compound. Hard gelatin capsules can also contain the targeted delivery composition including the targeting moiety and the carrier particle as well as the therapeutic agent in combination with solid powdered ingredients such as lactose, saccharose, sorbitol, mannitol, potato starch, corn starch, arnylopectin, cellulose derivatives or gelatin.

Dosage units for rectal or vaginal administration can be prepared (i) in the form of suppositories which contain the active substance mixed with a neutral fat base; (ii) in the form of a gelatin rectal capsule which contains the active substance in a mixture with a vegetable oil, paraffin oil or other suitable vehicle for gelatin rectal capsules; (iii) in the form of a ready-made micro enema; or (iv) in the form of a dry micro enema formulation to be reconstituted in a suitable solvent just prior to administration.

Liquid preparations for oral administration can be prepared in the form of syrups or suspensions, e.g. solutions or suspensions containing from 0.2% to 20% by weight of the active ingredient and the remainder consisting of sugar or sugar alcohols and a mixture of ethanol, water, glycerol, propylene glycol and polyethylene glycol. If desired, such liquid preparations can contain coloring agents, flavoring agents, saccharin and carboxymethyl cellulose or other thickening agents. Liquid preparations for oral administration can also be prepared in the form of a dry powder to be reconstituted with a suitable solvent prior to use.

Solutions for parenteral administration can be prepared as a solution of a compound of the invention in a pharmaceutically acceptable solvent, preferably in a concentration from 0.1% to 10% by weight. These solutions can also contain stabilizing ingredients and/or buffering ingredients and are dispensed into unit doses in the form of ampoules or vials. Solutions for parenteral administration can also be prepared as a dry preparation to be reconstituted with a suitable solvent extemporaneously before use.

The methods of the present invention to deliver the targeted delivery composition can also be used to deliver the targeted delivery composition orally in granular form including sprayed dried particles, or complexed to form micro or nanoparticles.

Methods for delivery of an agent to a discrete area of the brain are well known in the art, and can include the use of stereotactic imaging and delivery devices.

The present invention encompasses any suitable method for intracranial administration of a targeted delivery composition to a selected target tissue, including injection of an aqueous solution of a targeted delivery composition and implantation of a controlled release system, such as a targeted delivery composition incorporating polymeric implant at the selected target site. Use of a controlled release implant reduces the need for repeat injections. Intracranial implants are known. For example, brachytherapy for malignant gliomas can include stereotatically implanted, temporary, iodine-125 interstitial catheters. Scharfen. C. O., et al., High Activity Iodine-125 Intersitial Implant For Gliomas, Int. J. Radiation Oncology Biol Phys 24(4); 583-591:1992. Additionally, permanent, intracranial, low dose I-125 seeded catheter implants have been used to treat brain tumors. Gaspar, et al., Permanent I-125 Implants for Recurrent Malignant Gliomas, Int J Radiation Oncology Biol Phys 43(5); 977-982:1999. See also chapter 66, pages 577-580, Bellezza D., et al., Stereotactic Interstitial Brachytherapy, in Gildenberg P. L. et al., Textbook of Stereotactic and Functional Neurosurgery, McGraw-Hill (1998).

Furthermore, local administration of a targeted delivery composition to treat malignant gliomas by interstitial chemotherapy using surgically implanted, biodegradable implants is known. For example, intracranial administration of 3-bis(chloro-ethyl)-1-nitrosourea (BCNU) (Carmustine) containing polyanhydride waters, has found therapeutic application. Brem, H. et al., J Neuro-Oncology 26:111-123: 1995.

A polyanhydride polymer, Gliadel® (Stolle R & D, Inc., Cincinnati, Ohio) a copolymer of poly-carboxyphenoxypropane and sebacic acid in a ratio of 20:80 has been used to make implants, intracranially implanted to treat malignant gliomas. Polymer and BCNU can be co-dissolved in methylene chloride and spray-dried into microspheres. The microspheres can then be pressed into discs 1.4 cm in diameter and 1.0 mm thick by compression molding, packaged in aluminum foil pouches under nitrogen atmosphere and sterilized by 2.2 megaRads of gamma irradiation. The polymer permits release of carmustine over a 2-3 week period, although it can take more than a year for the polymer to be largely degraded. Brem, H., et al, Placebo-Controlled Trial of Safety and Efficacy of Intraoperative Controlled Delivery by Biodegradable Polymers of Chemotherapy for Recurrent Gilomas, Lancet 345; 10081012:1995.

Stereotactic procedures can be used for precise intracranial administration of targeted delivery composition in aqueous form or as an implant. A cranial neuroblastoma is also treated in this manner. Thus, intracranial administration of a targeted delivery composition can be carried out as follows.

A preliminary MRI scan of the patient can be carried out to obtain the length of the anterior commissure-posterior commissure line and its orientation to external bony landmarks. The base of the frame can then be aligned to the plane of the anterior commissure-posterior commissure line. CT guidance is used and can be supplemented with ventriculography. The posterior commissure can be visualized on 2-mm CT slices and used as a reference point.

Physiological corroboration of target tissue localization can be by use of high and low frequency stimulation through an electrode accompanying or incorporated into the long needle syringe used. A thermistor electrode 1.6 mm in diameter with a 2 mm exposed tip can be used (Radionics, Burlington, Mass.). With electrode high frequency stimulation (75 Hz) paraesthetic responses can be elicited in the forearm and hand at 0.5-1.0 V using a Radionics lesion generator (Radionics Radiofrequency Lesion Generator Model RFG3AV). At low frequency (5 Hz) activation or disruption of tremor in the affected limb occurred at 2-3 V. With the methods of the present invention, the electrode is not used to create a lesion. Following confirmation of target tissue localization, the targeted delivery composition can be injected. A typical injection is the desired number of units (i.e. about 0.1 to about 5 units of the targeted delivery composition in about 0.1 ml to about 0.5 ml of water or saline. A low injection volume can be used to minimize toxin diffusion away from target. Typically, the targeted delivery composition effect can be expected to wear off within a few days to about 2-4 months depending on the compound. Thus, an alternate targeted delivery composition format, targeted delivery composition incorporated within a polymeric implant, can be used to provide controlled, continuous release of a therapeutic amount of the targeted delivery composition at the desired location over a prolonged period (i.e. from about 1 year to about 6 years), thereby obviating the need for repeated targeted delivery composition injections.

Several methods can be used for stereotactically guided injection of the targeted delivery composition to various intracranial targets, such as the arcuate nucleus (AN) for treatment of acromegaly. Thus a stereotactic magnetic resonance (MRI) method relying on three-dimensional (3D) T1-weighted images for surgical planning and multiplanar T2-weighted images for direct visualization of the AN, coupled with electrophysiological recording and injection guidance for AN injection can be used. See e.g. Bejjani, B. P., et al., Bilateral Subthalamic Stimulation for Parkinson's Disease by Using Three-Dimensional Stereotactic Magnetic Resonance Imaging and Electrophysiological Guidance, J Neurosurg 92(4); 615-25:2000. The coordinates of the center of the AN can be determined with reference to the patient's anterior commissure-posterior commissure line and a brain atlas.

Electrophysiological monitoring through several parallel tracks can be performed simultaneously to define the functional target accurately. The central track, which is directed at the predetermined target by using MRI imaging, can be selected for neurotoxin injection. No surgical complications are expected.

Computer-aided atlas-based functional neurosurgery methodology can be used to accurately and precisely inject the desired neurotoxin or implant a neurotoxin controlled release implant. Such methodologies permit three-dimensional display and real-time manipulation of hypothalamic structures. Neurosurgical planning with mutually preregistered multiple brain atlases in all three orthogonal orientations is therefore possible and permits increased accuracy of target definition for targeted delivery composition injection or implantation, reduced time of the surgical procedure by decreasing the number of tracts, and facilitates planning of more sophisticated trajectories. See for example Nowinski W. L. et al., Computer-Aided Stereotactic Functional Neurosurgery Enhanced by the Use of the Multiple Brain Atlas Database, IEEE Trans Med Imaging 19(1); 62-69:2000.

In addition to polymeric implants, osmotic pumps can also be utilized for delivery of the targeted delivery composition of the present invention by continuous infusion. An osmotic minipump contains a high-osmolality chamber that surrounds a flexible, yet impermeable, reservoir filled with the targeted delivery composition-containing vehicle. Subsequent to the subcutaneous implantation of this minipump, extracellular fluid enters through an outer semi-permeable membrane into the high-osmolality chamber, thereby compressing the reservoir to release the targeted delivery composition at a controlled, pre-determined rate. The targeted delivery composition, released from the pump, is directed via a catheter to a stereotaxically placed cannula for infusion into the cerebroventricular space, as described herein.

The term "subject" and "individual" are used interchangeably herein, and refer to an animal, for example a human, to whom treatment, including prophylactic treatment, with the cells according to the present invention, is provided. The term "mammal" is intended to encompass a singular "mammal" and plural "mammals," and includes, but is not limited: to humans, primates such as apes, monkeys, orangutans, and chimpanzees; canids such as dogs and wolves; felids such as cats, lions, and tigers; equids such as horses, donkeys, and zebras, food animals such as cows, pigs, and sheep; ungulates such as deer and giraffes; rodents such as mice, rats, hamsters and guinea pigs; and bears. Preferably, the mammal is a human subject.

For the methods of the invention, the therapeutically effective amount or dose can be estimated initially from cell culture assays. Then, the dosage can be formulated for use in animal models so as to achieve a circulating concentration range that includes the $IC_{50}$ as determined in cell culture. Such information can then be used to more accurately determine useful doses in humans.

Toxicity and therapeutic effective amount of the compounds described herein can be determined by standard pharmaceutical procedures in cell cultures or experimental animals, e.g., by determining the $IC_{50}$ and the $LD_{50}$. The data obtained from these cell culture assays and animal studies can be used in formulating a range of dosage for use in humans. The dosage can vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval can be adjusted individually to provide plasma levels of the carrier portion containing the targeting and immune response triggering portions. These plasma levels are referred to as minimal effective concentrations (MECs). The MEC will vary for each compound but can be estimated from in vitro data. Dosages necessary to achieve the MEC will depend on individual characteristics and route of administration.

Dosage intervals can also be determined using MEC value. Compounds should be administered using a regimen that maintains plasma levels above the MEC for 10-90% of the time, preferably between 30-90% and most preferably between 50-90%.

In cases of local administration or selective uptake, the effective local concentration of the carrier portion containing the targeting and immune response triggering portions can not be related to plasma concentration. In such cases, other procedures known in the art can be employed to determine the correct dosage amount and interval.

The amount of the pharmaceutical composition of the preferred embodiments of the present invention administered will, of course, be dependent on the subject being treated, the severity of the affliction, the manner of administration, the judgment of the prescribing physician, etc.

The pharmaceutical composition can, if desired, be presented in a suitable container (e.g., a pack or dispenser device), such as an FDA approved kit, which can contain one or more unit dosage forms containing the carrier portion containing the targeting and immune response triggering portions.

The method can further comprise administering to a subject a second therapy, wherein the second therapy is therapy for the treatment of CNS disorders, or an anti-cancer therapy, for example an anti-angiogenic therapy, chemotherapy, immunotherapy, surgery, radiotherapy, immunosuppresive agents, or gene therapy with a therapeutic polynucleotide. The second therapy can be administered to the subject before, during, after or a combination thereof relative to the administration of the composition of the present invention. Anti-cancer therapies are well known in the art and are encompassed for use in the methods of the present invention. Chemotherapy includes, but is not limited to an alkylating agent, mitotic inhibitor, antibiotic, or antimetabolite, anti-angliogenic agents eyc. The chemotherapy can comprise administration of CPT-11, temozolomide, or a platin compound. Radiotherapy can include, for example, x-ray irradiation, w-irradiation, γ-irradiation, or microwaves It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages may mean±1%.

The invention is further illustrated by the following examples which should not be construed as limiting. The contents of all references cited throughout this application, including the U.S. provisional application 60/802,337 as well as the figures and table are incorporated herein by reference.

EXAMPLES

Methods:

Lentiviral experiments. Lentiviruses pseudotyped with VSV-G or RVG were generated by cotransfection of the lentiviral vector plasmids along with the helper plasmid pHR'8.9ΔVPR (core protein) and either the pVSV-g or pLTR-RVG envelope construct into 293T cells. Culture supernatants were harvested after 48 h and viral particles concentrated by ultracentrifugation. Lentiviruses were spin-infected onto Neuro 2a or HeLa cells in the presence of polybrene and after 48 h, transduction efficiency was determined by analyzing GFP expression by flow cytometry. shFVEJ and shLuc lentiviral constructs and experiments to test protection against intracranial JEV infections in mice have been previously reported[8].

Peptides and siRNAs. RVG (YTIWMPENPRPGTPCDIFTNSRGKRASNG) (SEQ ID NO: 13); RV-MAT (MNLLRKIVKNRRDEDTQKSSPASAPLDDG) (SEQ ID NO:33); RVG-9dR (YTIWMPENPRPGTPCDIFTNSRGKRASNGGGGRRRRRRRRR) (SEQ ID NO: 34); and RV-MAT-9dR (MNLLRKIVKNRRDEDTQKSSPASAPLDDGGGGRRRRRRRRR) (SEQ ID NO:35) peptides were synthesized and purified by HPLC at the Tufts University Core Facility. RVG and RVMAT peptides were also biotinylated at the carboxy terminus. siRNAs used in the studies included those targeting GFP (siGFP), firefly luciferase (siLuc), the envelope gene of JEV (siFvEJ) described in Kumar et al[8], murine Cu—Zn superoxide dismutase (SOD-1)[19], and β-galactosidase (βgal724) bearing a motif that elicits interferon production[26]. For some experiments, siRNA with FITC-label at the 3' end of the sense strand was used. siRNAs were obtained from Dharmacon, Inc or synthesized at Samchully Pharm. Co. Ltd, Seoul, Korea.

Peptide binding assay For peptide binding studies, Neuro 2a, HeLa, CHO, 293T and BHK21 cell lines and single cell suspensions made from freshly isolated mouse brain, spleen or liver were used. Cells were incubated with biotinylated peptides at a 2.5 µM in PBS for 20 min at 4° C., washed 3 times with PBS and then treated with streptavidin-PE (SAPE, BD Pharmingen) and analyzed by flow cytometry. For competition experiments, cells were incubated with biotinylated RVG peptide in the absence or presence of different concentrations of α-bungarotoxin (BTX, Sigma).

EMSA For gel mobility shift assays, 100 pmol siRNA was incubated with peptides at 1:0.1, 1:1 and 1:10 molar ratios of siRNA:peptide for 15 min, electrophoresed on a 2% agarose gel and stained with ethidium bromide. siRNA without peptide or incubated with RVG-bio (without 9R) served as controls.

Cytotoxicity assay To test the cytotoxicity of RVG-9R/siRNA complexes, Neuro 2a cells (triplicates of $2\times10^5$ cells/well in 12-well plates) were incubated at different concentrations of peptide/siRNA complexes for 24-48 h before determining the viability by a standard MTT assay.

siRNA transduction and gene silencing in vitro. Uptake of siRNA into cells was monitored using FITC-labeled siGFP. siRNA (100 pmoles) was incubated with different concentrations of RVG-9R or RV-MAT-9R in serum free DMEM for 15 min at RT. The complexes were then incubated with Neuro2a and HeLa cells (the cells were plated at $5\times10^4$ cells per well in 12-well plates the previous day). After 4 h incubation at 37° C. the medium was replaced with 2 ml of fresh medium supplemented with 10% fetal bovine serum (FBS; Hyclone) and the cells were cultured for an additional 8-10 h before examining by flow cytometry. Transfection with Lipofectamine 2000 was done as per the manufacturers' instructions.

To test gene silencing, Neuro 2a cells stably expressing GFP after transduction with the pLL3.7 lentiviral vector were incubated with 100 pmoles of siGFP complexed with peptides at 10:1 peptide/siRNA ratio and GFP expression analyzed 48 h after transduction.

Animal experiments for testing siRNA delivery and gene silencing. Balb/c, C57BL/6-Tg(ACTB-EGFP)1Osb/J and NOD/SCID were purchased from Jackson Labs and used at 4-6 weeks of age. All mouse experiments had been approved by the CBRI institutional review board and animal infection experiments were done in a biosafety level 3 animal facility at the CBRI.

To test peptide uptake by brain cells, 50 µg of biotinylated peptides in 0.2 ml PBS were injected into the tail veins of Balb/c mice and 4 h later, single cell suspension of brains were permeabilized, treated with SAPE and analyzed by flow cytometry. For all siRNA delivery experiments, peptide/siRNA complexes (at a peptide:siRNA molar ratio of 10:1) were prepared in 100 µl of 5% glucose and injected iv at 50 µg siRNA/mouse/injection. FITC-siRNA delivery and SOD-1 gene knockdown experiments were done in Balb/c mice. GFP silencing experiments were carried out in C57BL/6-Tg(ACTB-EGFP)1Osb/J mice. For testing protection against JEV encephalitis, NOD/SCID mice were intraperitoneally challenged with 5 $LD_{50}$ of JEV ($LD_{50}$ was predetermined using serial dilutions of the virus) 4 h before beginning iv peptide/siRNA treatment.

Staining of brain sections. Mice were injected twice with RVG-9R bound siRNA-FITC and brains harvested 10-12 hours later. Brains were sectioned frozen on a sliding microtome to 40 µm thickness and incubated for 48 h at 4° C. with mouse anti-FITC antibodies (Jackson Immuno Research, 20 µg/ml) or isotype controls (IgG1 from murine myeloma, Sigma, 20 µg/ml). Sections were washed and FITC immunoreactivity visualized with Alexa 488 goat anti-mouse secondary antibodies (1:500, Invitrogen).

Quantitative RT-PCR. Total RNA was isolated form different organs of peptide/SOD1 siRNA treated mice using RNeasy RNA isolation kit (Qiagen). The RNA was reverse transcribed using Superscript III and random hexamers (Invitrogen) according to the manufacturer's protocol. Real-time PCR was performed on 1 µl of complementary DNA, or a comparable amount of RNA without reverse transcriptase, using the QuantiTect™ SYBR Green PCR kit (Qiagen) according to the manufacturer's instructions. Amplification conditions were: 40 cycles of denaturation at 95° C. for 20 s, annealing at 60° C. for 30 s, and extension at 69° C. for 30 s using Biorad icycler. Primers for GAPDH and SOD-1 have been previously described(27). Standard curves were generated and the relative amount of mRNA was normalized to GAPDH mRNA. Specificity was re-verified by melt curve analysis and agarose gel electrophoresis.

Northern blot to detect siRNA. 5 µg of RNA extracted from cell suspensions by the small RNeasy mini kit (Qiagen,), were electrophoresed on a 15% TBE-UREA PAGE gel (Invitrogen), transferred to a positively charged nylon membrane (BrightStar-plus; Ambion) and probed with sense siRNA probes as described earlier (8).

Western blot analysis. Mouse tissue cell suspensions were homogenized in buffer containing 25 mM HEPES pH 7.5, 300 mM NaCl, 1.5 mM MgCl2 0.1% Triton X 100, 0.2 mM EDTA and 0.5 mM DTT and protease-inhibitor cocktail (Complete-Mini; Roche Diagnostic). The samples (10 µg protein each) were electrophoresed on 15% SDS-polyacrylamide mini gels (Bio-Rad) and transferred to a polyvinylidene difluoride membrane. The membrane was probed with anti-β-actin antibodies (Sigma) or anti-SOD1 antibodies (Stressgen Biotechnologies) and visualized using ECL Western blot system (Pierce Biotechnologies).

IFN response. Balb/c mice were iv injected with 50 µg of either siFvEJ or siβgal728 complexed with RVG-9R peptide. siRNA βgal728 complexed to Lipofectamine-2000™ served as a positive control. Serum samples obtained 7 h after siRNA treatment were tested for interferon-alpha levels using mouse type-I IFN detection ELISA kit (PBL Biomedical Laboratories), according to the manufacturer's instructions.

Quantification and statistical analysis. Western blot experiments were quantified by determination of band intensities using ImageJ public domain software from the National Institutes of Health (http://rsb.info.nih.gov/ij/). All statistical analysis comparing groups of mice treated with test and control peptides were performed by one-way ANOVA followed by Bonferroni's post test. $P<0.05$ was considered significant.

Example 1

Figure 1:
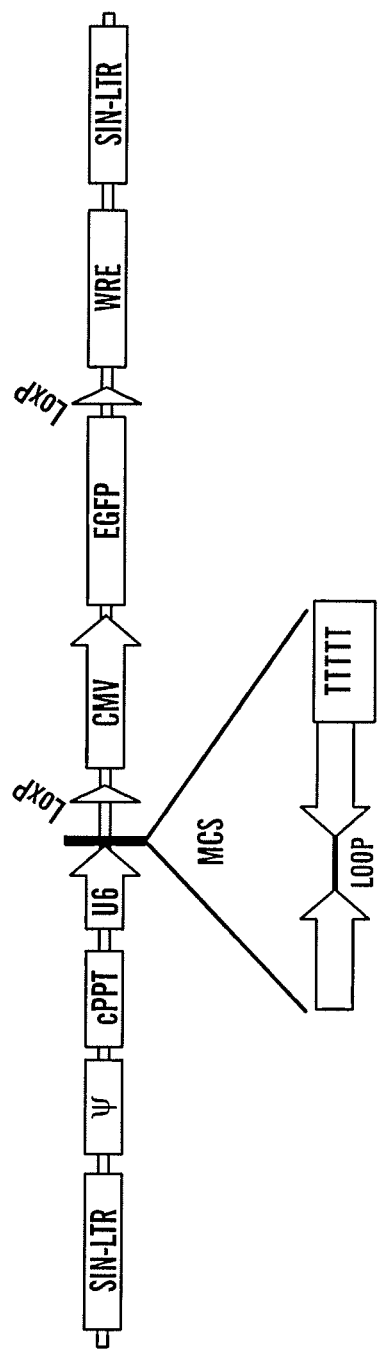
Figure 2:
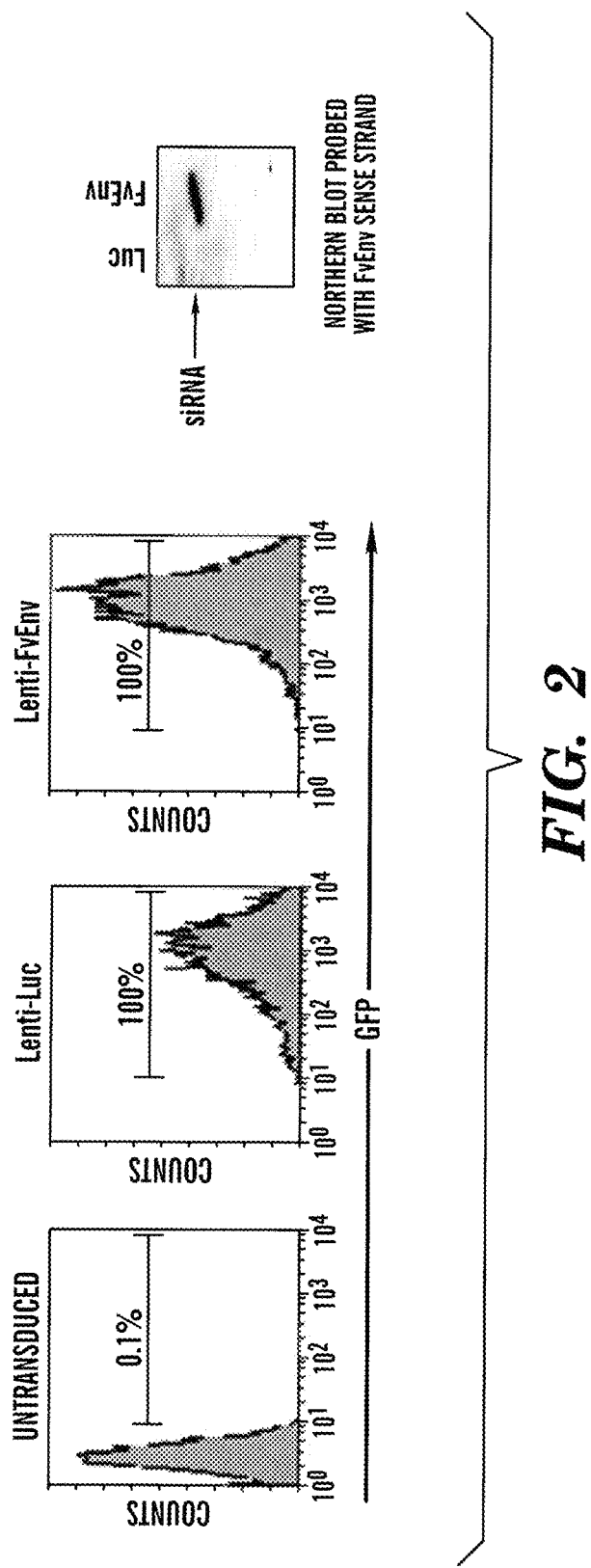
Figure 3:
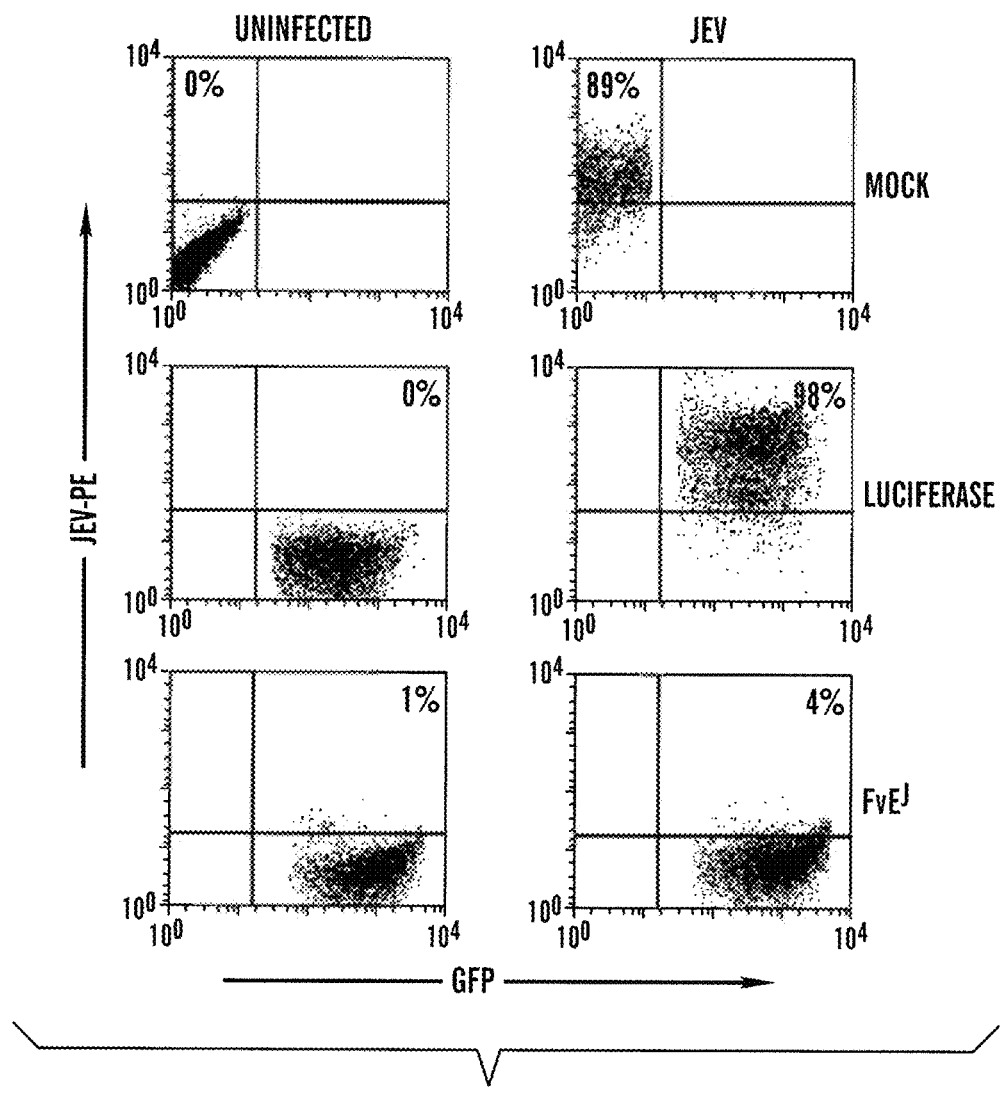
Figure 4:
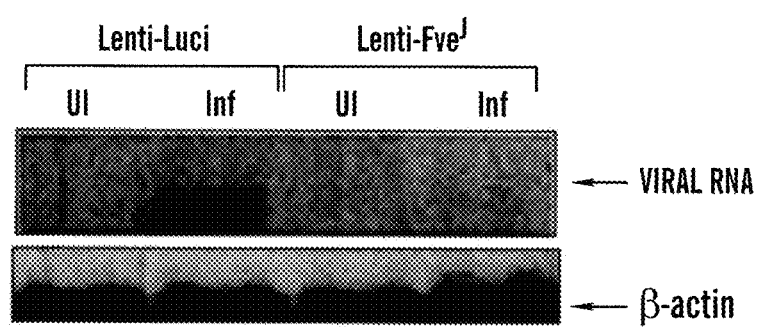

Generation of lentiviral vectors for stable expression of shRNAs and testing their antiviral properties. After testing several viral gene targets, the inventors discovered that a siRNA designed to target the envelope gene of JEV ($FvE^J$, nt 1287-1305 of the genomic RNA) could afford robust protection against JEV infection in cell lines. For stable endogenous expression of this siRNA, the inventors used the lentiviral vector Lentilox pLL3.7 described by Rubinson et al [88]. This vector contains an RNA polymerase III U6 promoter to drive shRNA expression as well as a GFP reporter gene driven off the CMV promoter to enable easy identification of transduced cells (FIG. 1). Two complementary oligonucleotides with the siRNA sequence followed by a 9 nt loop, a reverse complement of the siRNA and transcription termination signal were commercially synthesized, annealed and cloned into Xho and Hpa digested pLL3.7 vector. Lentiviral particles were generated in 293 T cells by transfection with pLL3.7/$FvE^J$ or pLL3.7/Luc (encoding luciferase shRNA to serve as control) constructs along with plasmids encoding VSV-G and delta vpr (to supply envelope and regulatory proteins in trans) using Fugene reagent. Viral supernatants were harvested 48 hours after transfection. The virus was titrated in 293T cells using GFP expression as a marker and expressed as transduction units (TU)/ml. When BHK-21 cells were infected with the lentivirus by spinfection in the presence of 8 ug/ml polybrene, nearly 100% cells were transduced as evidenced by GFP expression (FIG. 2, left). Stable intracellular production of $FvE^J$ specific siRNA was ascertained 10 days after transduction by Northern analysis using $^{32}P$ labeled synthetic siRNA sense strand as probe (FIG. 2, right). To test the ability of shRNA to inhibit JEV replication, stably transduced BHK-21 cells were infected with JEV at a multiplicity of infection (moi) of 1 and the viral replication monitored by flow cytometry after staining with a JEV-specific monoclonal 48 h postinfection. As shown in FIG. 3, compared with mock and control luciferase shRNA, $FvE^J$ shRNA was able to abrogate JEV infection. That the antiviral effect of FvE mediated protection is due to siRNA-induced degradation of viral RNA was confirmed in Northern blots using viral cDNA probe (FIG. 4).

Figure 5:
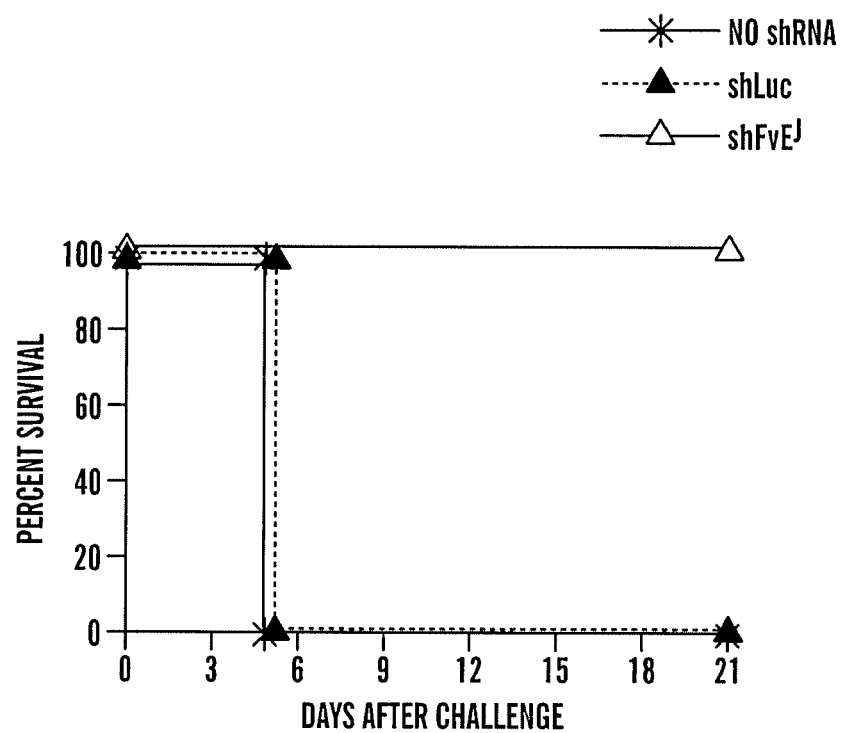
Figure 6:
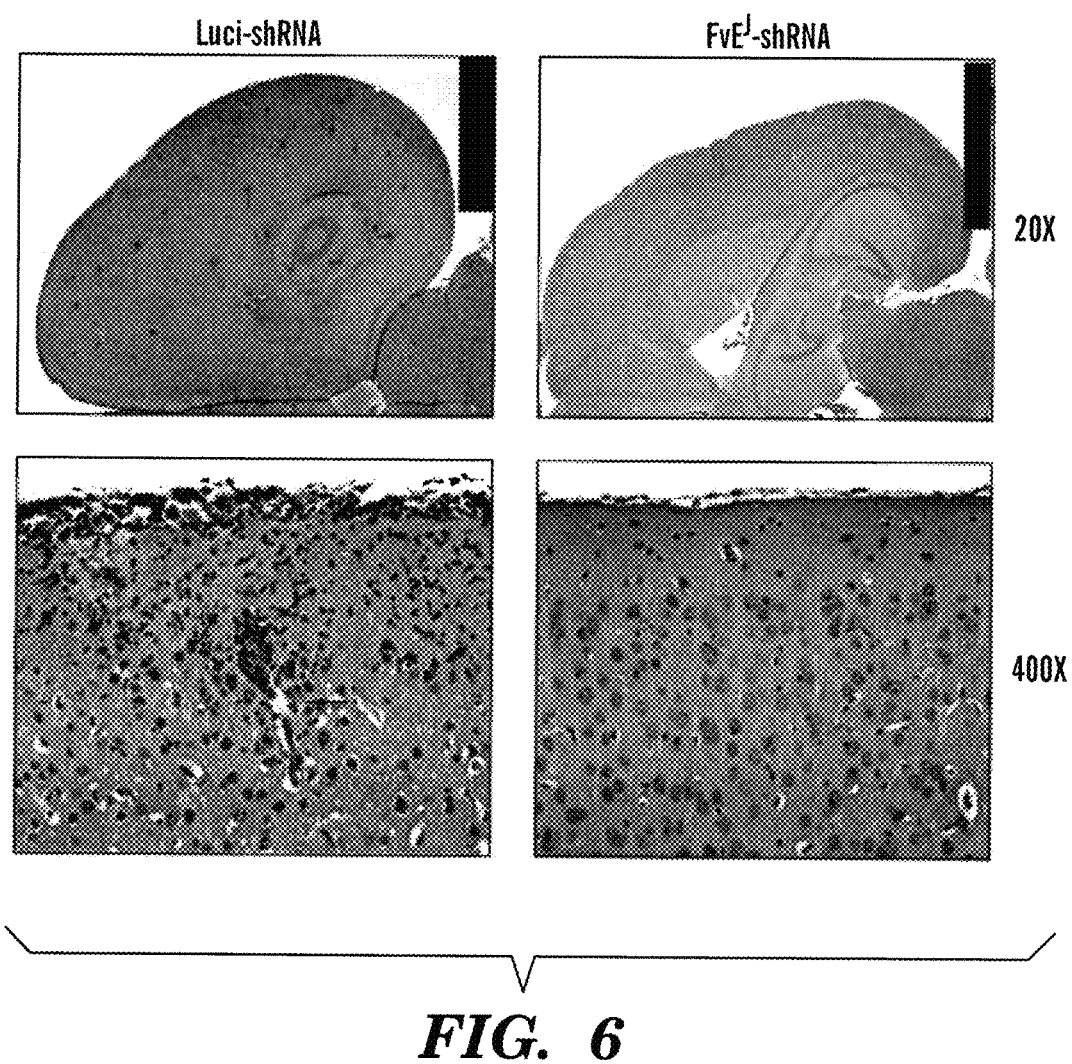
Figures 7A, 7B:
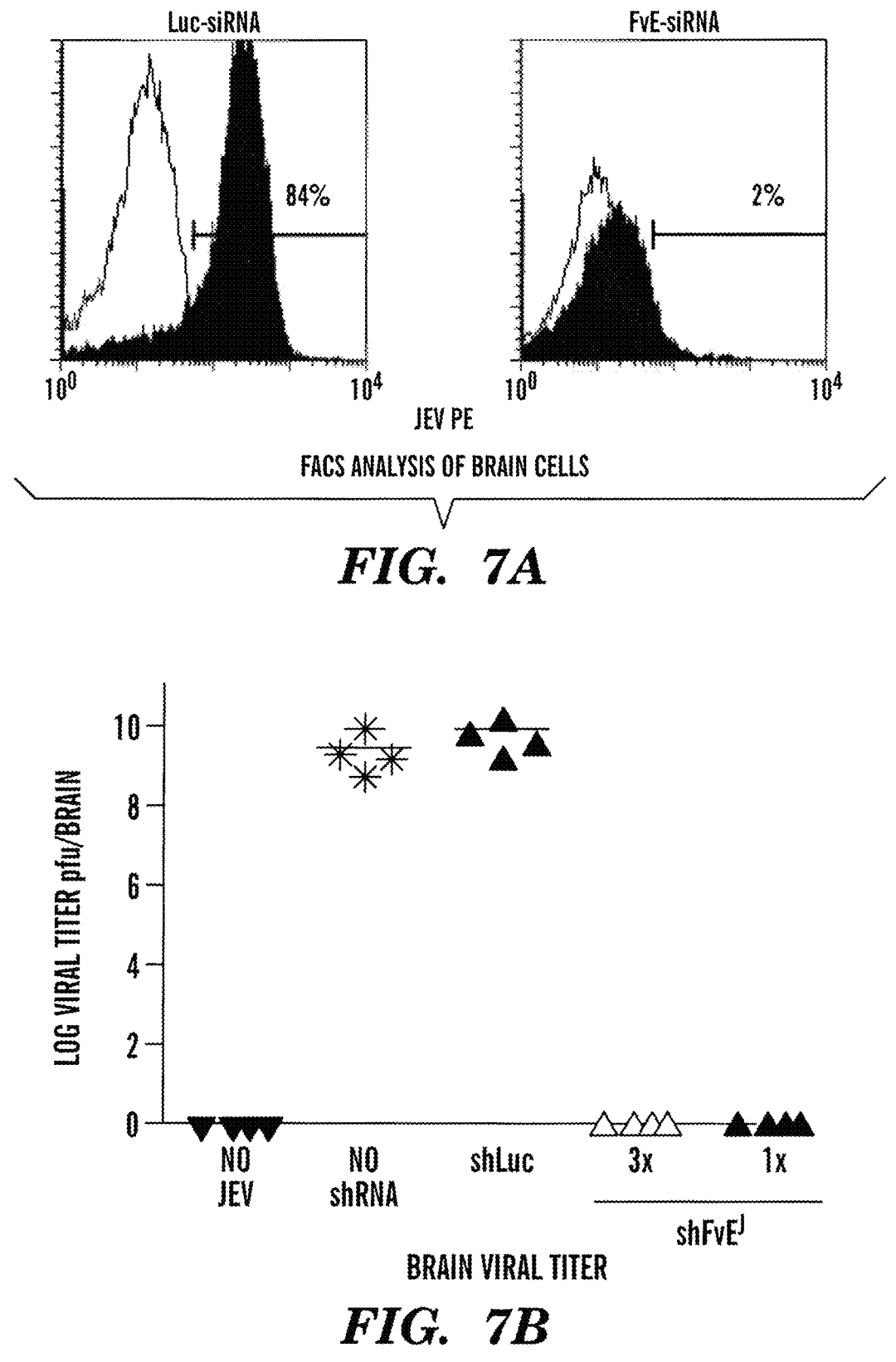

In vivo effectiveness of $FvE^J$. The inventors also tested the $FvE^J$ shRNA for conferring protection against JEV-induced encephalitis. Balb/c mice were injected with 2×10$^5$ TU of either luciferase or $FvE^J$ shRNA encoding lentiviruses intracranially into the frontal lobe as detailed in Kumar et al [6]. Two days later, the mice were again injected with lentiviruses along with the challenge JE virus at the earlier injection site and monitored for survival over time. While all 10 mice injected with no or control shRNA died within 7 days, all 10 mice injected with $FvE^J$ shRNA survived indefinitely (FIG. 5). The brains of control mice on day 5 after JEV challenge showed the typical histopathological features of viral encephalitis with leukocyte infiltration and neuronal apoptosis, while no brain inflammation or neuropathology was observed in the $FvE^J$ shRNA treated mice (FIG. 6). Virus titration of brain homogenates revealed extremely high levels of viral replication in the control mice, whereas the FvE$^J$ shRNA-treated mice remained virus free (FIG. 7).

Figure 8A:
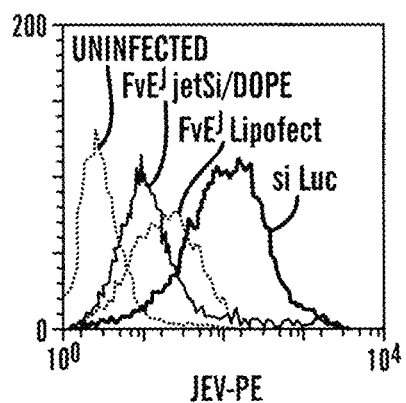
Figure 8B:
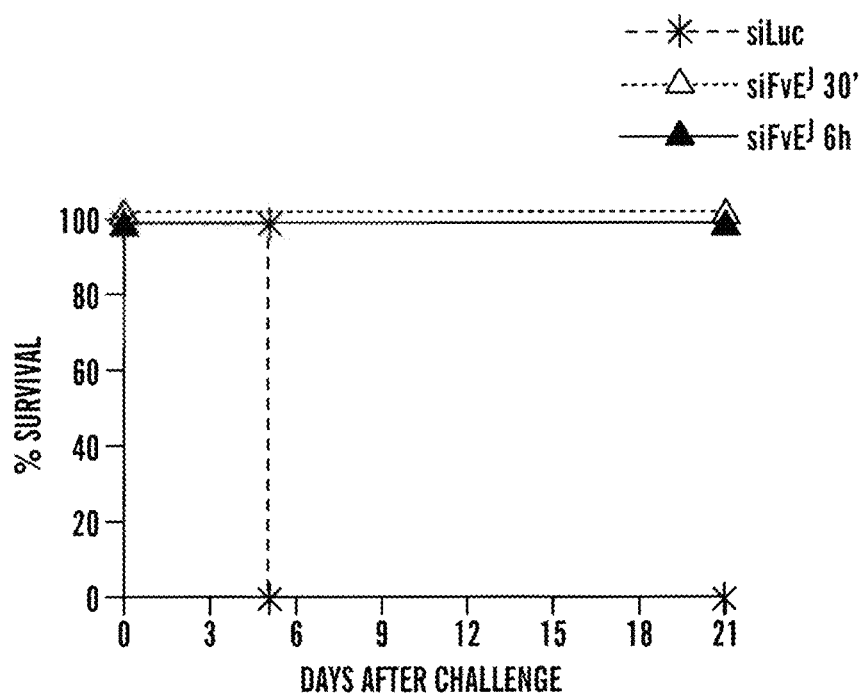

Synthetic siRNAs can also protect mice from JEV-induced encephalitis. Because synthetic siRNA provides a drug like approach for treatment without the safety concerns associated with integration of lentiviral vectors, the inventors also tested the FvE$^J$ siRNA for protection. To enable uptake of siRNA by brain cells, the inventors complexed the siFvE$^J$ or the control siLuc siRNAs with the cationic lipid formulation, JetSI along with the fusogenic lipid dioleoyl-phosphatidyl-ethanolamine (DOPE), which has been recently used to deliver siRNA to brain cells in vivo without toxicity [66]. After ascertaining that JetSI/DOPE can successfully deliver siFvE$^J$ into Neuro 2a cells to inhibit JEV replication (FIG. 8a), the inventors injected approximately 40 μg (3.2 nmoles) of siRNAs, complexed with JetSI/DOPE intracranially 30 min or 6 h after JEV challenge. While in both groups, all mice injected with the control siLuc died within 5-7 days, all siFvE$^J$-treated mice in both groups survived indefinitely (FIG. 8b). The siRNA treatment neither induced IFN responsive genes as measured by RT-PCR analysis nor led to increased levels of serum IFN levels as measured by ELISA (data not shown). Moreover, the siFvE$^J$-treated mice were completely healthy and brain sections taken 21 days after challenge showed no histopathological alterations, demonstrating that the treatment was non-toxic (FIG. 6). These results show that a single treatment with siFvE$^J$ can protect against fatal encephalitis even when administered after the infection has already been established. A siRNA targeting the envelope gene of WNV (siFvEW) was also effective in suppressing WN encephalitis.

Figure 9A:
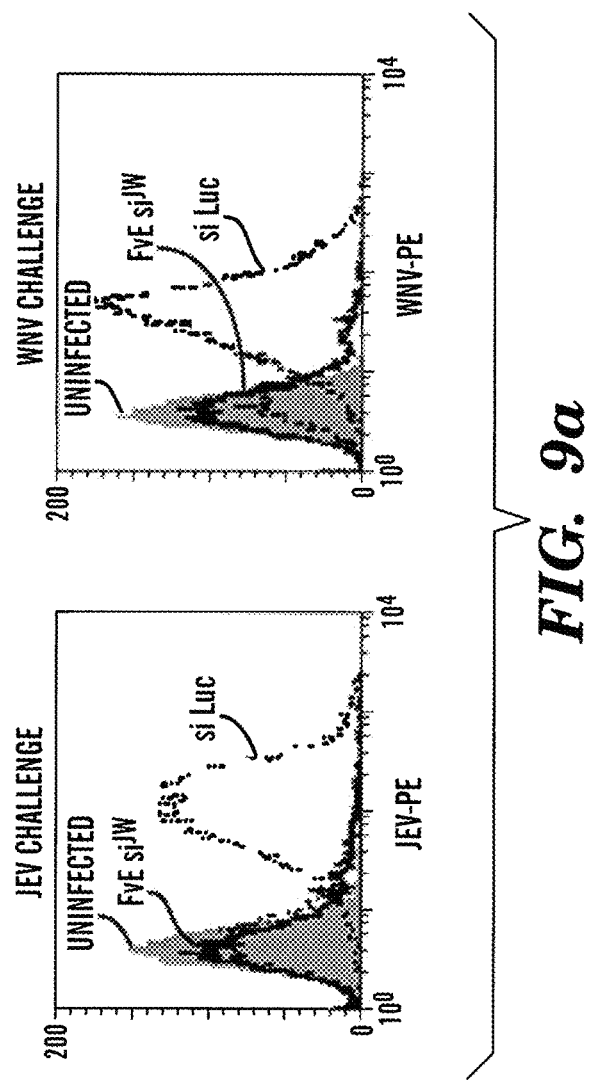
Figure 9B:
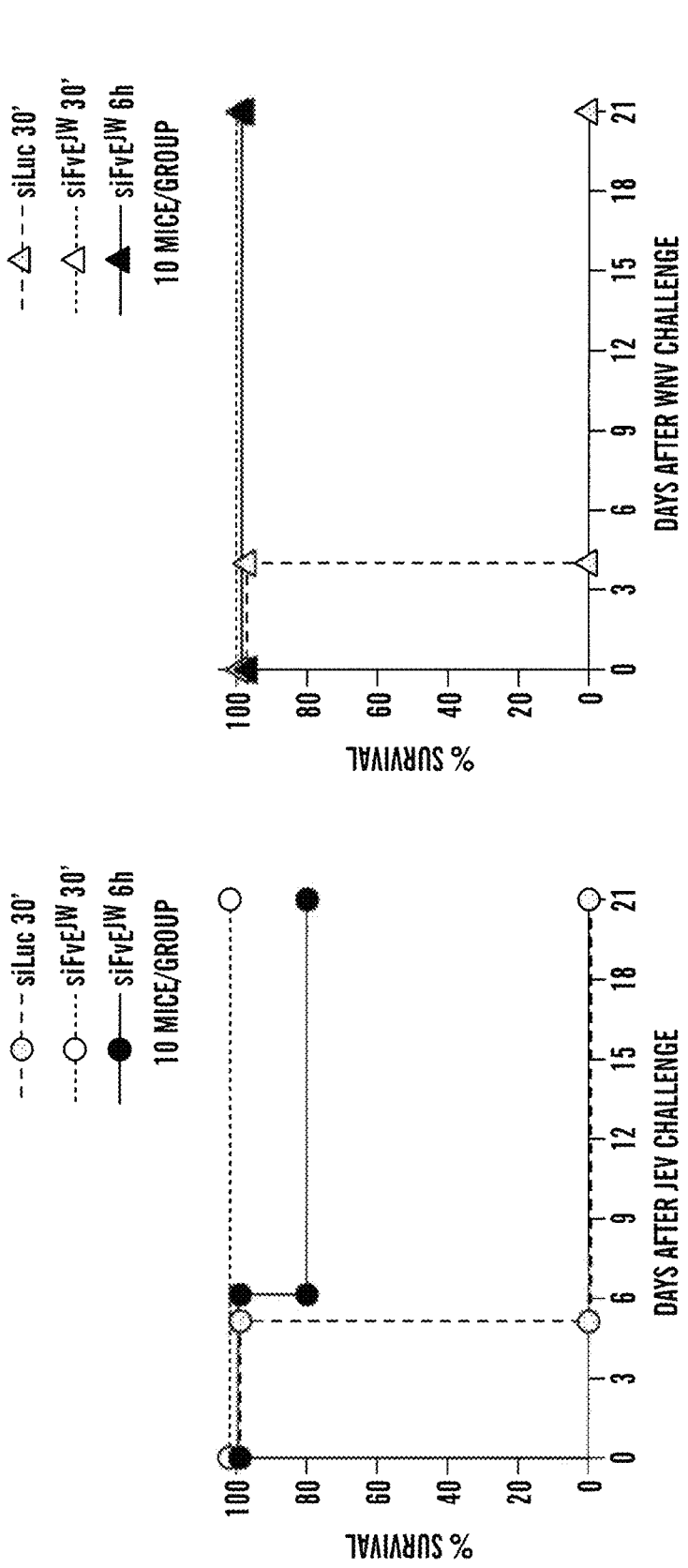

A single siRNA targeting a region that is highly conserved among different flaviviruses can suppress encephalitis induced by Both JEV and WNV. In contrast to siFvE$^J$ sequence (nt 1287-1305), which is only conserved within the strains of JEV, a contiguous sequence in the E gene comprising the cd loop (nt 1307-1328) is essential for mediating viral entry and thus, is highly conserved even at the nucleotide level between all sequenced strains of JEV, WNV as well as St. Louis encephalitis virus [89]. Thus the inventors designed a 21 nt siRNA (siFvE$^{JW}$) corresponding to this region. This sequence is identical between the two viruses except for a single nucleotide mismatch at positions 3 and 21 in the JEV and WNV target sequence respectively, positions where mutations are reported to be well tolerated with no significant effect on siRNA efficacy [90]. As shown in FIG. 9a, siFvE$^{JW}$ effectively suppressed both viruses in the Neuro 2a cell line. Moreover, it was also able to afford 80-100% protection against lethal encephalitis induced by either JEV or WNV (FIG. 9b). These results indicate that by careful design of conserved target sites, it can be possible to use a single siRNA to suppress related viruses across species. Importantly, the inventors have discovered that siRNA treatment after infection can also be effective. The inventors have also observed that siRNA treatment even after 18 h of infection protected 80% of mice against encephalitis. However, it was unable to protect when administered 24 h after infection, when progeny virus has already infected distant areas of brain.

Figure 10:
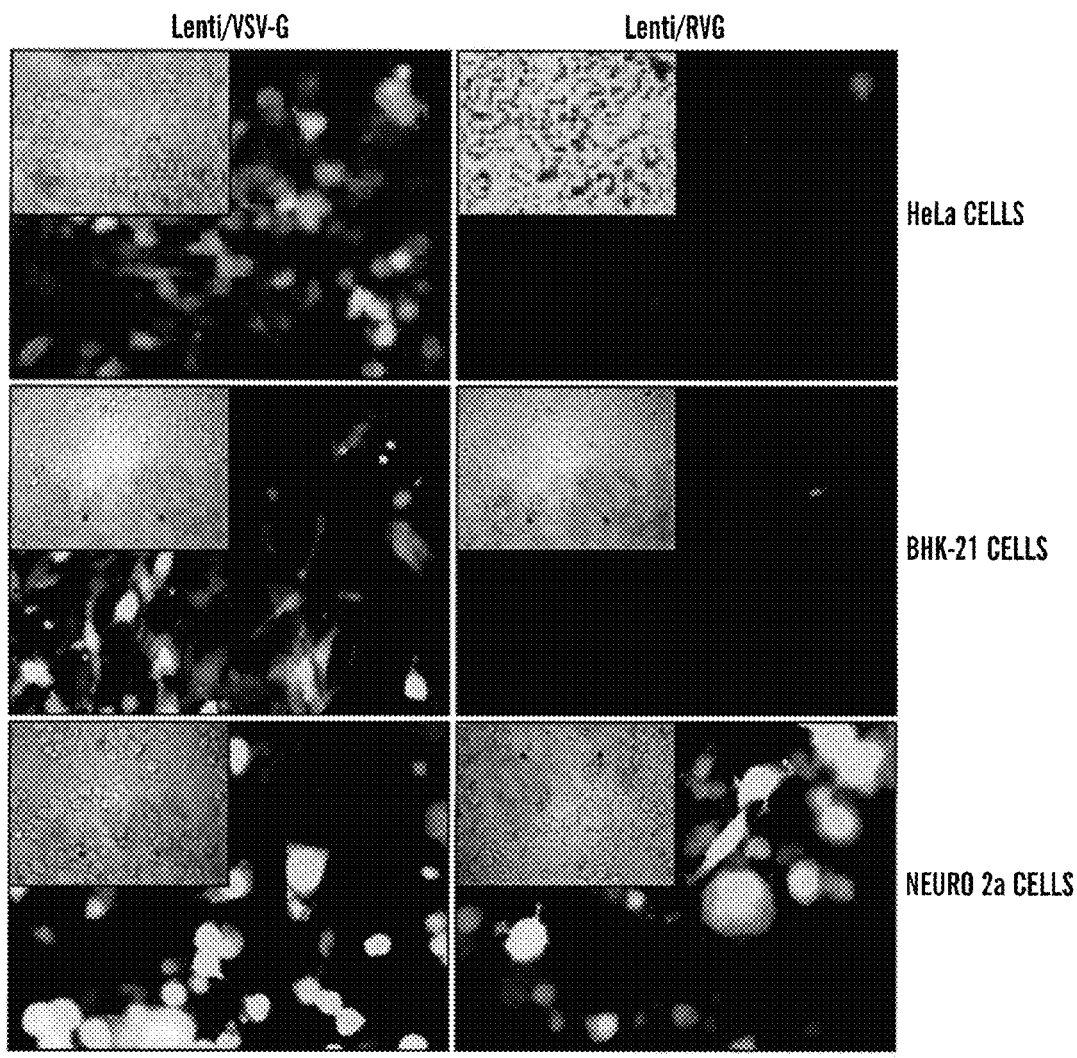

Pseudotyping the lentivirus with RVG permits neuronal cell-specific targeting and enhances RNAi effectiveness in the CNS. Pseudotyping the lentivirus with the neurotropic Rabies virus glycoprotein (RVG) instead of the conventionally used VSV-G allows retrograde axonal transport to distal neurons and results in more extensive spread of the transduced genes [11]. Moreover, RVG pseudotyping can also allow neuronal cell specific targeting, which could be an advantage to prevent si/shRNA uptake by irrelevant cells. Thus, the inventors tested lentiviruses pseudotyped with either VSV-G or RVG for their ability to deliver shRNA to non-neuronal or neuronal cells. Indeed, whereas the VSV-G pseudotyped lentivirus uniformly transduced both HeLa and the mouse neuroblastoma cell line Neuro 2a, RVG pseudotyping allowed transduction exclusively of Neuro 2a, but not HeLa or BHK-21 non-neuronal cells (FIG. 10). Further, the RVG-pseudotyped shFvE$^J$ exhibited a more potent antiviral activity compared to the corresponding VSV-G pseudotyped lentivirus in that, it abrogated JEV infection in Neuro 2a even at an moi of 50 (highest dose tested) while the protection offered by VSVG-pseudotyped shFvE$^J$ diminished at moi's higher than 25. This can be due to differences in the respective receptor density, enabling better entry of RVG pseudotyped virus in neuronal cells.

Figure 11:
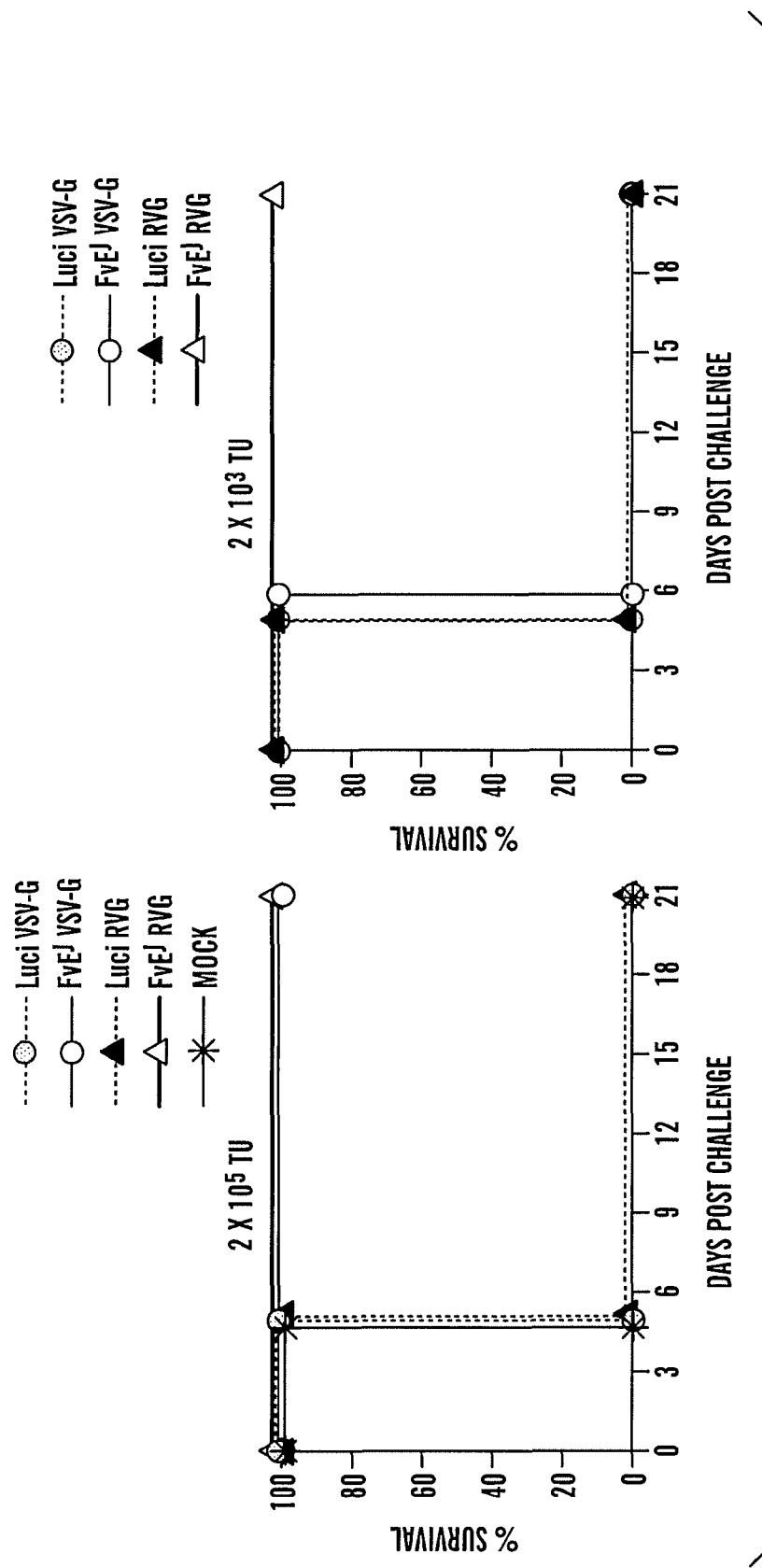

The inventors compared the VSV-G- or RVG-pseudotyped shFvE$^J$ lentiviruses for relative efficacy in vivo by titrating the dose of lentivirus required to provide complete protection against a lethal intracranial challenge with JEV. Mice received either 2×10$^5$ or 2×10$^3$ transduction units (TU) of the control shLuc or shFvE$^J$, pseudotyped with either VSV-G or RVG. Mice were challenged with 4 LD$_{50}$ of JEV injected at the same site and observed for mortality for 21 days. All mice injected with the control shLuc, whether pseudotyped with VSV-G or RVG developed encephalitis and succumbed by day 6. In contrast, all mice receiving a high dose of shFvE$^J$ lentivirus with either pseudotyping were protected. However, when a lower dose of lentivirus (2×10$^3$ TU) was used, all mice receiving VSV-G-pseudotyped shFvE$^J$ died, while all mice injected with RVG-pseudotyped shFvE$^J$ lentivirus survived indefinitely (FIG. 11). When the extent of protection was further analyzed by serially increasing the dose of JEV challenge, we could show that the RVG-pseudotyped lentivirus could protect against JEV challenge at as high a dose as 50 LD$_{50}$. This enhanced protective efficacy is probably due to the capacity of RVG-pseudotyped lentivirus to mediate retrograde axonal transport and increase lateral spread from the injection site [11], resulting in a more extensive protection of neighboring cells.

Figure 12:
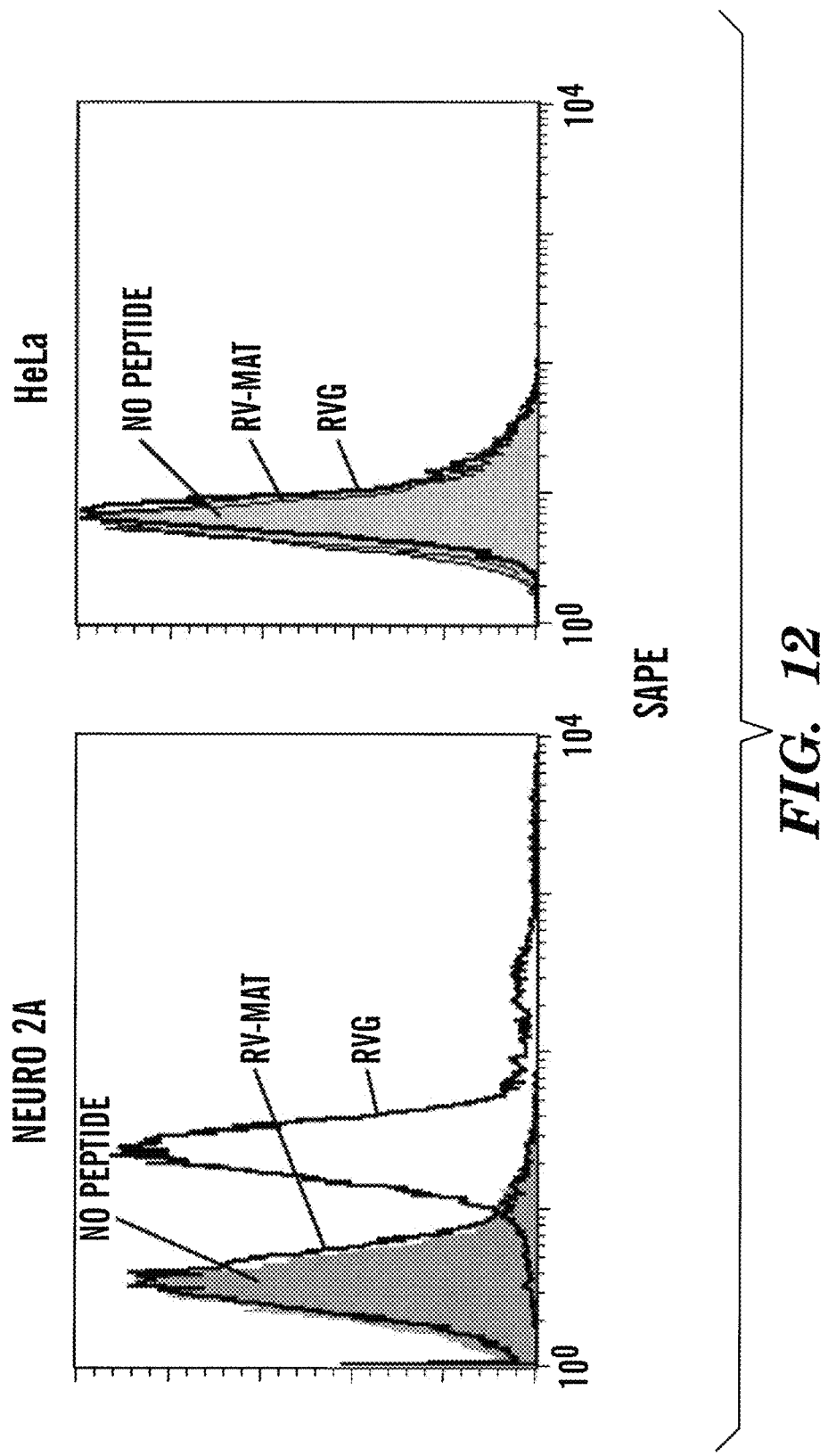
Figure 13:
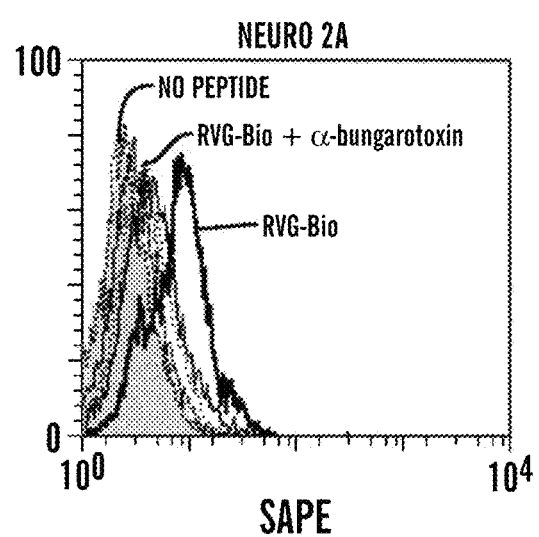
Figure 14:
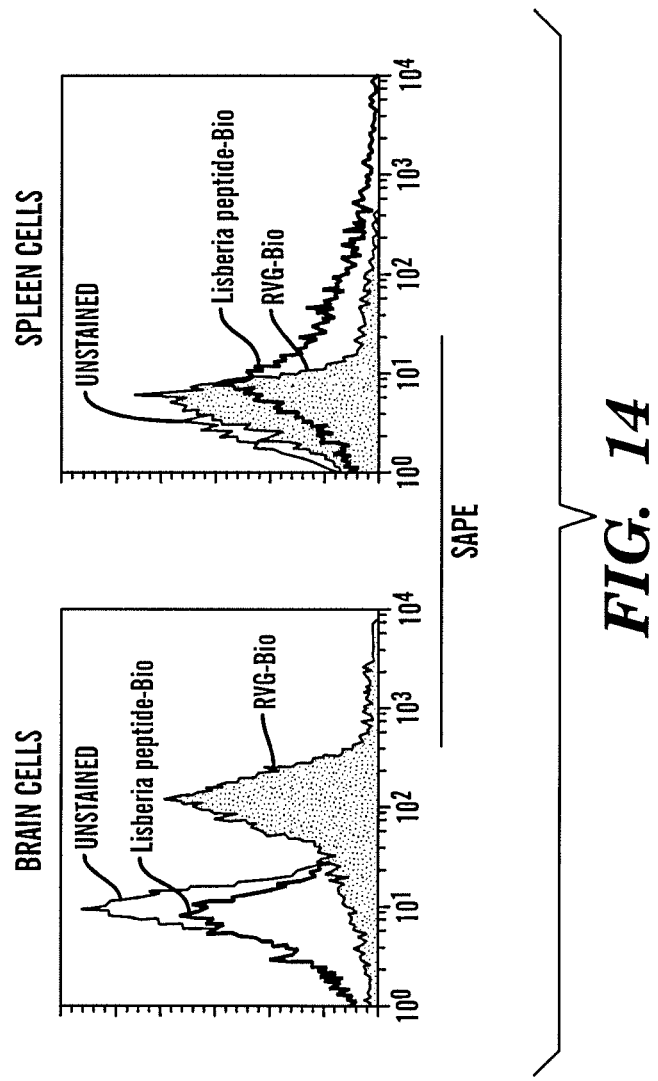
Figure 15:
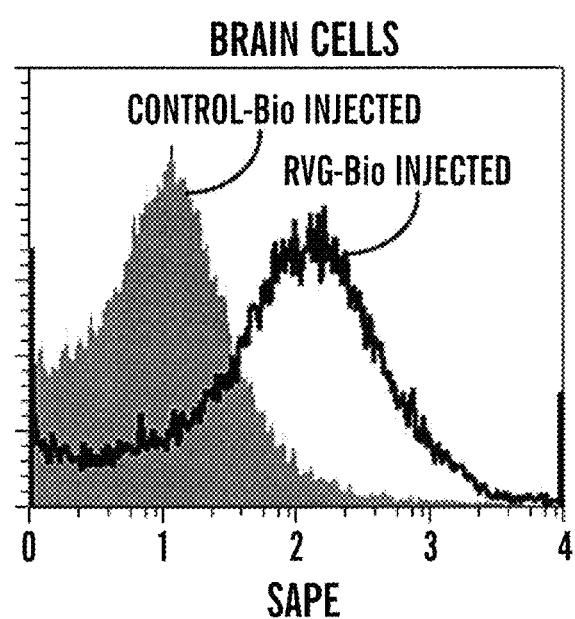

A short synthetic peptide derived from RVG specifically binds neuronal cells. The glycoprotein from the neurotropic Rabies virus shows a significant homology with the snake venom alpha neurotoxin that binds to the nicotinic acetylcholine receptor [91]. In fact, further studies showed that the acetylcholine receptor is also a Rabies virus receptor [92, 93]. Interestingly an RVG peptide was also found to competitively inhibit α-bungarotoxin binding to the acetylcholine receptor [94]. Structure-function analysis of the binding domain identified a 29 aa peptide (spanning aa 173-202 in the RVG) as sufficient for competition with bungarotoxin binding [95]. However, there has been no indication that this 29 mer RVG peptide (RVG) (SEQ ID NO:13) binds to neuronal cells that express the α subunit of the acetylcholine receptor, nor that it can facilitate delivery to such cells. To detect binding, the inventors synthesized a biotinylated 29mer RVG peptide (SEQ ID NO:13). For control purpose, the inventors also synthesized a 29mer scrambled RVG peptide (herein termed "RV-MAT"). Acetylcholine expressing Neuro 2a [96,97] and the receptor negative HeLa cells were incubated with the peptides, washed and stained with streptavidin PE (SAPE). As shown in FIG. 12, Neuro 2a but not HeLa cells specifically bound the RVG peptide corresponding to SEQ ID NO:13, but not the scrambled RVG peptide. To further confirm the binding specificity, the inventors tested if a bungarotoxin can inhibit RVG peptide binding. Neuro 2a cells were first treated with different concentrations (10-9 to 10-3 M) of α-bungarotoxin and then tested for RVG peptide (10-7 M) binding. As shown in FIG. 13, α-bungarotoxin could effectively inhibit RVG peptide binding. The inventors also tested if the RVG peptide can bind primary neuronal cells isolated ex vivo from the mouse brain. Single cell suspensions of freshly isolated brain cells and splenocytes (for control) were treated with RVG-Bio or a control biotinylated listeria peptide and SAPE and examined by flow cytometry. Again, the brain cells but not splenocytes were capable of binding the RVG peptide (FIG. 14). These results demonstrate that the RVG peptide corresponding to SEQ ID NO:13 can specifically bind primary neuronal cells. Because actelylcholine receptor α7 subunit is widely expressed by many cell types in the brain including the neurons, astrocytes and glia cells as well as the brain capillary endothelial cells [98], the inventors also tested if RVG peptide delivered intravenously in mice can be taken up by the brain cells. Mice were injected IV with 100 μg of biotinylated RVG peptide or a control listeria peptide and 2 h later, single cell suspensions of brain examined by flow cytometry after staining with SAPE. As shown in FIG. 15, brain cells from mice treated with RVG but not control peptide were positive for PE fluorescence, demonstrating that the RVG peptide can allow transvascular delivery of si/shRNAs.

Figure 16:
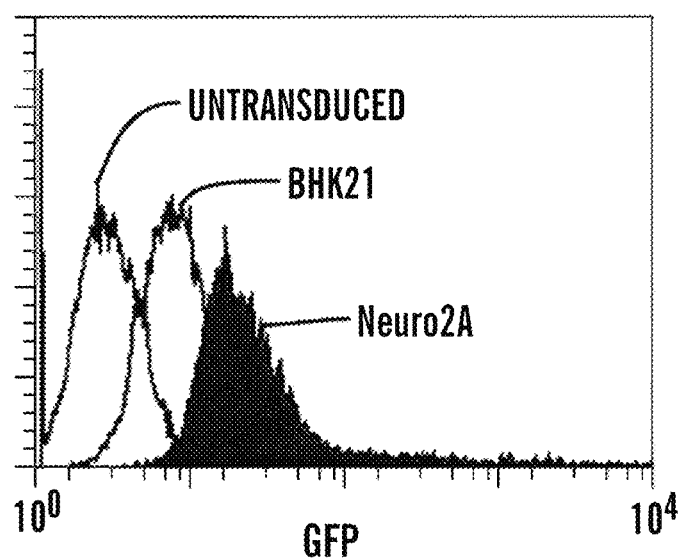

RVG peptide fused to the cell penetrating HIV TAT peptide can deliver shRNA vector to neuronal cells. Although the RVG peptide can bind neuronal cells, it does not bind nucleic acids and therefore cannot be used alone to transport naked nucleic acids, for example si/shRNAs. However, if the RVG peptide corresponding to SEQ ID NO:13 is coated on nanoparticles or liposomes, the RVG peptide can be used to deliver nucleic acids to neuronal cells. Alternatively, a peptide from HIV-TAT can bind the negatively charged nucleic acids by charge interaction. HIV-TAT is also useful as it also functions as a cell penetrating peptide[7-9]. Thus, the inventors synthesized a chimeric RVGTAT peptide consisting of the 29mer RVG and 15mer TAT peptide. For testing delivery, the inventors first incubated the pLL37 lentiviral vector DNA with the RVG-TAT peptide (5 μg of DNA with 5-10 fold excess of peptide on a molar basis in a total volume of 0.5 ml DMEM without serum) for 15-20 min and then, this mixture was added to Neuro 2a or BHK-21 cells. After incubating for 4 h, the cells were washed and cultured with serum containing culture media. Two days later, the cells were examined for GFP expression by flow cytometry. As shown in FIG. 16, Neuro 2a cells expressed GFP at a high level compared to minimal GFP expression by BHK-21 cells. Since BHK-21 cells do not bind the RVG peptide, the small level of GFP expression seen probably represents transduction mediated by the TAT peptide alone as has been previously reported [7,8]. This demonstrates that the RVG peptide by enhancing cell binding can greatly enhance delivery in neuronal cells. Thus, RVG-TAT peptide can also be used for neuronal nucleic acid (such as DNA or RNA) delivery.

Figure 17:
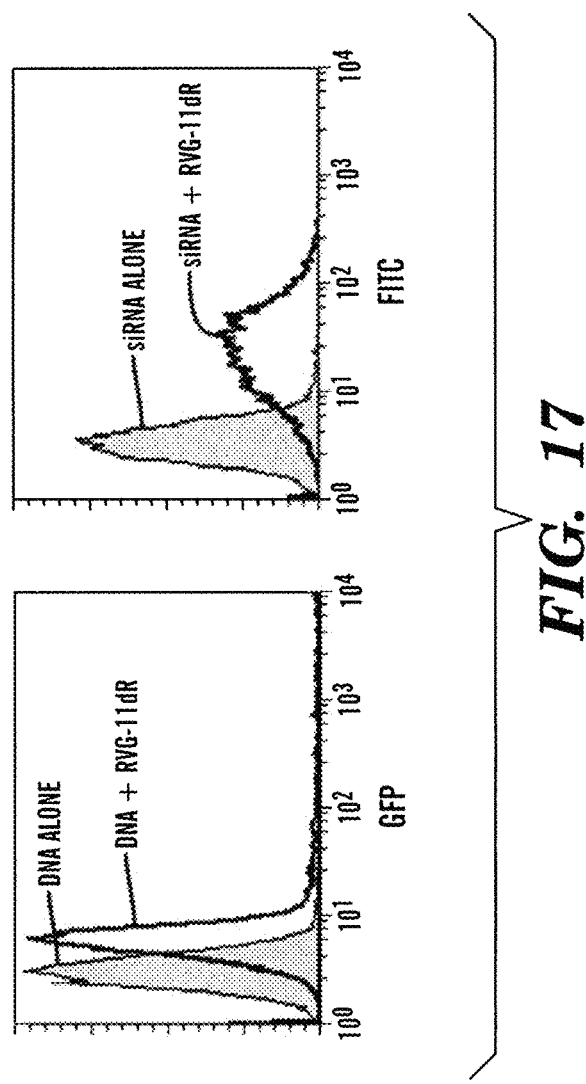
Figure 18:
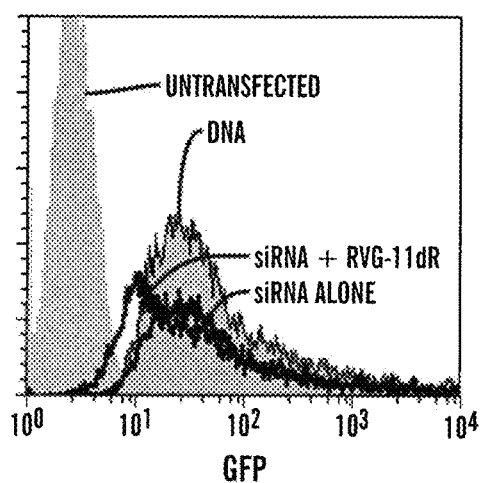
FIG. 18 shows RVG-11dR delivered siRNA is functional. Neuro 2a cells were first transfected with GFP DNA and then treated with GFP siRNA alone or bound to RVG-11dR and examined 2 days later.

RVG peptide fused to the cell penetrating 11dR peptide can deliver synthetic siRNA to neuronal cells. A 9-11 mer of 1-arginine (9R or 11R) peptide has been shown to be 20-fold more efficient than the TAT peptide at cellular uptake, and substitution of 1 with d-arginine was found to enhance uptake by >100 fold [100]. The inventors tested if the RVG peptide fused to an 11mer dR (RVG-11dR) could deliver shRNA vector and siRNAs to neuronal cells. The pLL3.7 shRNA vector or a FITC conjugated GFP siRNA was bound to RVG-11dR peptide as described for the RVG-TAT and was used to transduce Neuro 2a cells. GFP expression and siRNA delivery was determined by flow cytometry 2 days later after thoroughly washing the cells. As FIG. 17 shows, 11dR was able to deliver both the DNA vector and siRNA efficiently. The inventors also tested if the siRNA delivered via RVG-11dR can mediate gene silencing. For this, Neuro 2a cells were first transduced with a GFP encoding plasmid via RVG-TAT and 2 days later, the cells were transduced with anti-GFP siRNA bound to RVG-11dR and GFP expression determined 2 days later. Indeed, RVG-11dR delivered siRNA could inhibit GFP expression significantly (FIG. 18).

Figure 19:
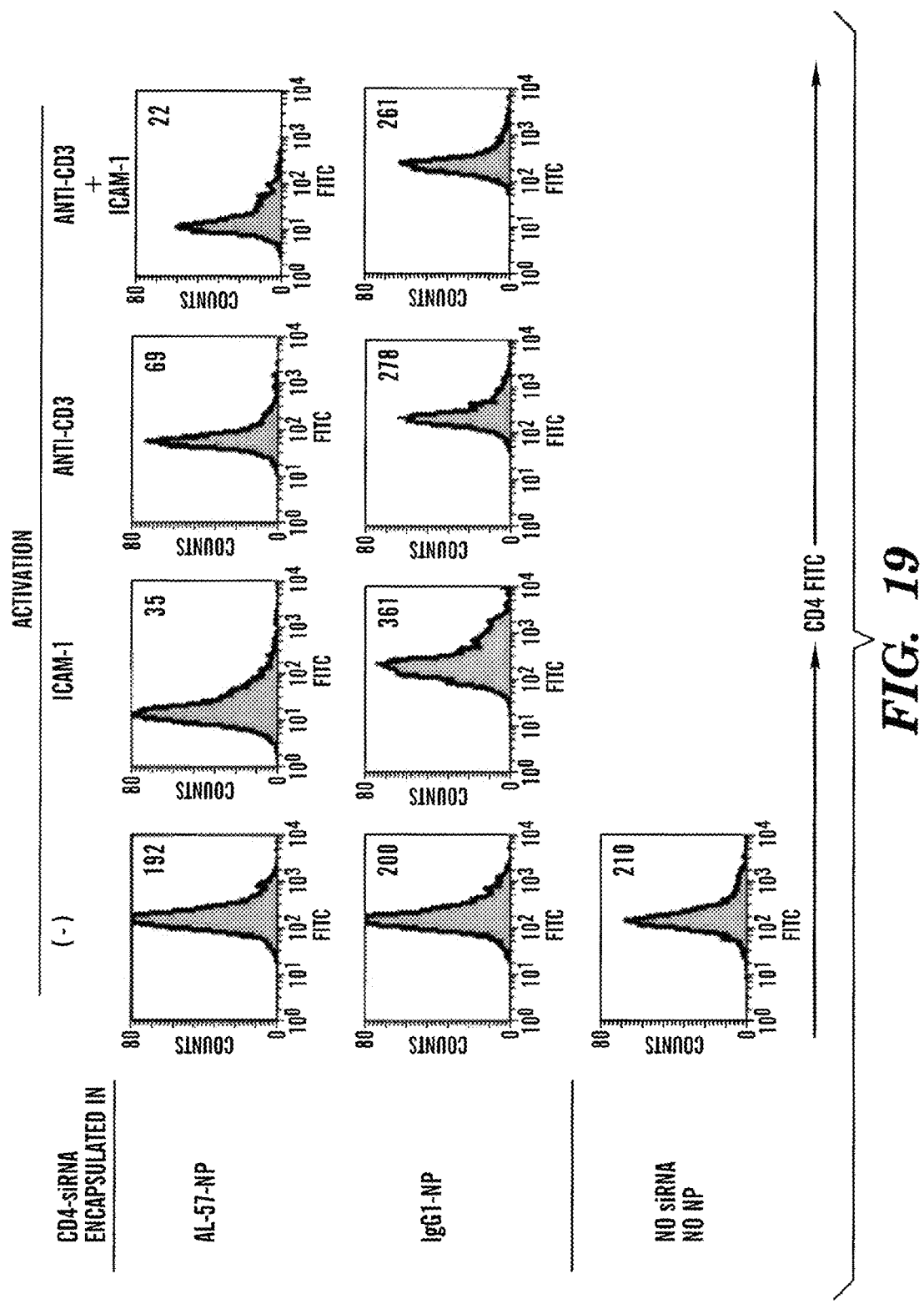
FIG. 19 shows immunoliposomes for targeted delivery of siRNA. Activated CD4 T cells were incubated with CD4 siRNA-encapsulated hyaluran liposomes coated with LFA-1 (AL-57) or an isotype control (IgG1) antibody and examined for CD4 expression 2 days later.

Targeting Liposomes. The inventors describe herein the use of RVG-coated liposomes for in vivo neuronal delivery. A novel nanoscale hyaluronan-coated liposome formulation for nontoxic, targeted in vivo delivery was recently developed, as described in U.S. Provisional Appl. 60/723,686, which is incorporated herein in its entirety by reference. Here, the siRNA is encapsulated with a liposome for protection against enzymes in the body fluids. The liposome is also coated with hyaluran, which enables covalent linkage with targeting molecules such as antibodies or peptides. To specifically target activated T cells, the liposome was coated with the AL-57 antibody that recognizes the form of LFA-1 that is expressed on activated T cells [101]. CD4 T cells were activated with ICAM-1 or αCD3 antibody alone or together. On day 7 after activation, the cells were treated with CD4 siRNA (1 nmol) encapsulated liposomes coated with the LFA-1 or an isotype control antibody and CD4 expression determined 2 days later. CD4 expression was specifically reduced after delivery of CD4 siRNA with LFA-1 antibody coated liposomes (FIG. 19, top panel), but not with control antibody coated liposomes (FIG. 19, middle panel).

Example 2

To address the question of whether different carrier particles could be fused to an RVG peptide for delivery of nucleic acids, for example RNAi to neuronal cells for functional knock down of gene expression, the inventors used a short peptide derived from the Rabies virus (RVG) that binds to the nicotinic acetylcholine receptor as a means of neuronal cell targeting. The RVG was biotinylated to detect neuronal cell-specific binding (as shown in FIG. 20A) and was inhibited by α-bungarotoxin as shown in FIG. 20B. The RVG peptide could also be detected in the mouse brain 2 hours after intravenous injection (FIG. 21). A chimeric peptide, termed "CORVUS" or "RVG-9R" herein comprises an RVG peptide of SEQ ID NO:13 fused to a carrier particle which is a cell penetrating peptide such as a polymeric arginine residue of various lengths was used to test siRNA binding and delivery. As used in Example 2, CORVUS (an RVG peptide comprising SEQ ID NO:13 fused to a 9 or 11 mer of 1-arginine (called R9 or 11R)), was assessed for its ability to deliver shRNA vector and RNAi to neuronal cells in vitro and in vivo and to deliver functional RNAi. CORVUS binds and delivers siRNA to neuronal cells in vitro (FIG. 22), and CORVUS carrying anti-GFP RNAi was functional and silenced GFP expression in GFP expressing Neuro 2a cells (FIG. 23). Furthermore, i.v. injection of CORVUS loaded with FITC labeled RNAi was significantly detected in brain tissue of mice (FIG. 24C) compared to the control peptide (FIG. 24A). GFP siRNA complexed with CORVUS specifically silenced GFP expression in the brain of GFP transgenic mice after intravenous (i.v.) administration (FIG. 25B), and SOD-1 siRNA complexed with CORVUS specifically silenced mouse SOD1 expression at the mRNA level and protein level in the brain (FIG. 29B).

Example 3

Pseudotyping lentivirus with RVG confers neuronal cell-specificity. The envelope glycoprotein of Rabies virus (RVG) specifically interacts with the nicotinic acetylcholine receptor (AchR) on neuronal cells to infect brain cells[153,154]. The inventors assessed if pseudotyping lentivirus with RVG, instead of the conventionally used vesicular stomatitis virus glycoprotein (VSV-G) could confer neuronal cell-specificity. GFP encoding lentiviral vector Lentilox pLL3.7[155] pseudotyped with either RVG or VSV-G was tested for ability to infect neuronal or non-neuronal cells. While VSV-G pseudotyped lentivirus infected both cell types, RVG pseudotyping resulted in infection exclusively of Neuro 2a, but not HeLa cells (FIG. 10). RVG has been shown to mediate retrograde axonal transport and increase the spread of a viral vector within the brain[156], the inventors also tested if RVG pseudotyping of pLL3.7 encoding a shRNA (shFvE$^J$)[157] targeting Japanese encephalitis virus (JEV) increases its antiviral efficacy. Different concentrations of shFvE$^J$ lentivirus, pseudotyped with RVG or VSV-G were tested for protection efficacy in an intracranial (ic) JEV challenge assay[157]. While at a high dose ($2 \times 10_5$ TU) both lentiviruses equally afforded protection, at a lower dose ($2 \times 10_3$ TU), all mice treated with RVG pseudotyped lentivirus survived but all those treated with VSV-G-pseudotyped lentivirus succumbed to JEV infection (FIG. 11). Collectively, these results suggest that RVG confers neuronal cell-specificity and in addition, by facilitating retro-axonal and trans-synaptic spread[156] also enhances transduction of neighboring neuronal cells.

Short RVG peptide specifically binds to neuronal cells. To determine if the 29mer RVG peptide specifically binds to neuronal cells that express AchR, the inventors assessed the ability of a biotinylated 29mer RVG peptide and a control peptide of similar length derived from the viral matrix protein (RV-MAT) to bind to neuronal cells. The snake venom toxin α-bungarotoxin specifically binds AchR, and a short 29 amino acid peptide derived from RVG (spanning aa 173-202 in the RVG) has been previously reported to competitively inhibit α-bungarotoxin binding to the AchR in solution[10]. The inventors discovered that a 29 mer RVG peptide specifically binds neuronal cells that express AchR. To detect binding, the inventors synthesized a biotinylated 29 mer RVG peptide and for control purpose, a peptide of similar length derived from the viral matrix protein (RV-MAT). AchR expressing Neuro 2a [11,12] and the receptor negative HeLa cells were incubated with the peptides, washed and stained with phycoerythrin-conjugated streptavidin (SAPE). As shown in FIG. 26a, Neuro 2a but not HeLa cells specifically bound the RVG-, but not RV-MAT peptide. RVG peptide also did not bind several other non-neuronal cells including 293T, BHK21 and CHO (FIG. 26b).

To further confirm AchR-mediated binding specificity, the inventors tested if α-bungarotoxin can inhibit RVG peptide binding to Neuro 2a cells. Neuro 2a cells were treated with different concentrations ($10^{-10}$ to $10^{-3}$M) of α-bungarotoxin along with RVG peptide (2.5 μM). As shown in FIG. 26c, α-bungarotoxin inhibited RVG peptide binding in a dose-dependent manner in that, at concentrations of $10^{-7}$ M and higher, α-bungarotoxin progressively decreased RVG binding. Moreover, α-bungarotoxin was also able to displace pre-bound RVG from Neuro 2a cells (not shown).

The inventors also tested if the RVG peptide can bind primary neuronal cells. Single cell suspensions of freshly isolated mouse brain cells were treated with RVG-bio or the control RVG-MAT-bio peptides followed by SAPE. Again, brain cells but not splenocytes were capable of binding the RVG peptide (FIG. 26d). Because AchR is also expressed by the brain capillary endothelial cells[13], the inventors also tested if RVG peptide injected iv can be taken up by the brain cells. Mice were injected iv with 50 μg of biotinylated RVG peptide or control RVG-MAT peptide and 4 h later, single cell suspensions of brain were examined by flow cytometry after internal staining with SAPE. As shown in FIG. 26e, brain cells from mice treated with RVG but not the control peptide were positive for PE fluorescence, demonstrating that the RVG peptide can cross the BBB to enter brain cells.

Chimera RVG-9R peptide can bind and deliver siRNA to neuronal cells. While the RVG peptide can bind neuronal cells, it does not bind nucleic acids and therefore cannot be used alone to transport siRNA. However, short positively charged peptides called cell penetrating peptides (such as a peptide from HIV-TAT) can bind the negatively charged nucleic acids by charge interaction and also enable cellular uptake[14-16]. A nona (L-arginine) (R9) peptide has been shown to be 20-fold more efficient than the TAT peptide at cellular uptake, and substitution of 1 with d-arginine was found to enhance uptake by >100 fold[17]. Moreover, a cholesterol conjugated oligo dR has been used for siRNA delivery to suppress VEGF gene in a tumor model in mice[18]. The inventors tested if the RVG peptide fused to 9dR could deliver siRNAs to neuronal cells. The inventors synthesized an RVG-spacer-9dR (designated RVG-9R) peptide and a control RV-MAT-spacer-9dR (RV-MAT-9R) peptide for these studies. The ability of these peptides to bind siRNA was tested in a gel electrophoresis mobility shift assay (EMSA). As shown in FIG. 27a, both RVG-9R and RV-MAT-9R peptides were able to bind siRNA, resulting in quenching of fluorescence and mobility shift in a dose-dependent manner with maximal and complete binding at 1:10 molar ratio, demonstrating that the 9R tagging confers siRNA-binding property to both peptides. Next, the inventors tested if RVG-9R can be used to transduce siRNA into cells. For this, 100 pmoles of FITC conjugated siRNA was complexed with different concentrations of RVG-9R and Neuro 2a cells were incubated with the complexes for 4 h, washed and cultured for another 8-10 hours in fresh media before examining by flow cytometry. As shown in FIG. 27b, RVG-9R was able to transduce siRNA in a dose-dependent manner and a peptide:siRNA molar ratio of 10:1 was optimal for maximal transduction, in agreement with EMSA results shown in FIG. 27a. To determine the neuronal specificity of RVG-9R-mediated siRNA delivery, the inventors transduced Neuro 2a and HeLa cells using FITC-siRNA complexed with RVG-9R or RV-MAT-9R at the optimal siRNA:peptide ratio, using lipofectamine as positive control. As shown in FIG. 27c, lipofectamine enabled siRNA uptake by both HeLa and Neuro 2a cells as expected and RV-MAT-9R was unable to transduce either cell type. In contrast, RVG-9R was able to transduce Neuro 2a but not HeLa cells to a similar degree as lipofectamine. Thus, RVG-9R allows neuronal cell-specific siRNA delivery.

Although these results indicate that siRNA can be transduced into Neuro-2a cells by RVG-9R, siRNA will not be functional and/or effective unless it is delivered into the cytoplasm, and therefore it was important to test if the introduced siRNA is functional in silencing specific gene expression. The inventors then assessed the gene silencing ability of the RVG-9R delivered siRNA. Neuro 2a cells stably expressing high levels of GFP (by lentiviral introduction of pLL3.7 vector encoding GFP) were transduced with anti-GFP siRNA bound to RVG-9R or RVMAT-9R or transfected with siRNA using lipofectamine (positive control), and GFP expression determined 2 days later. RV-MAT-9R complexed with siRNA was unable to reduce GFP levels, while RVG-9R/siRNA silenced GFP expression to a similar extent as lipofectamine transfection (FIG. 27d), demonstrating that the RVG-9R delivered siRNA is indeed functional. RVG-9R/siRNA complex was also found to be non-toxic in a MTT assay (>90% viability 48 h after treatment of Neuro-2a cells with RVG-9R at up to 25:1 peptide-siRNA ratio, data not shown).

RVG-9R peptide can deliver siRNA to the brain cells after iv injection in mice. For potential in vivo delivery, the inventors examined if RVG-9R binding protects the siRNA against degradation from serum nucleases. Unlike naked siRNA, RVG-9R-bound siRNA was at stable for up to 8 h (FIG. 31).

The inventors assessed if RVG-9R can transport siRNA to brain cells in vivo after iv injection. To examine this, the inventors examined if the RVG-9R binding protects siRNA against degradation from serum proteases. Mice were injected iv with 50 µg of FITC-labeled siRNA complexed with either RVG-9R or the control RV-MAT-9R peptide (at 1:10 molar ratio) in a total volume of 100 µl in 5% glucose solution. The iv injection was repeated after 6 hours and 10 hours later, mice were sacrificed and single cell suspensions from brain, spleen and liver were examined by flow cytometry for the presence of FITC-positive cells. As shown in FIG. 28a, FITC fluorescence was detected in the brain only when the siRNA was complexed to RVG-9R. However, no FITC uptake was seen in the spleen or liver, demonstrating that RVG-9R allows specific targeting of brain cells in vivo. The presence of FITC positive cells in different regions throughout the mouse brain was also confirmed by microscopic examination of brain sections stained with an anti-FITC antibody, as shown in FIG. 28b.

Gene silencing by transvascular delivery of siRNA bound to RVG-9R. The inventors tested brain-specific gene silencing after iv administration of RVG-9R/siRNA using GFP Tg mice. GFP siRNA (50 µg) was complexed with RVG-9R or RV-MAT-9R and injected in a volume of 100 µl daily for 3 days in the tail veins of GFP Tg mice. Two days after the last injection, mice were sacrificed and single cell suspensions of brain, spleen and liver examined for GFP expression by flow cytometry. In GFP Tg mice, the GFP expression was highest in the brain compared to the spleen and liver. Despite this, a significant reduction in GFP expression was seen after treatment with RVG-9R-bound but not with RV-MAT-bound siRNA (FIG. 29b). Moreover, this gene silencing was only observed in the brain and not the liver and spleen, demonstrating the specificity of brain targeting. To confirm these results in a different system, the inventors also tested silencing of an endogenous gene in the brain following RVG-9R mediated iv siRNA delivery. In this case, wild type Balb/c mice were iv injected with 50 µg of an siRNA targeting mouse SOD1gene[19] complexed to RVG-9R or RV-MAT-9R, 3 times at 8 h intervals and SOD1 mRNA and protein levels in the brain, spleen and liver were measured 24 h after the last injection by qPCR and Western blot respectively. While no changes were detected in SOD1 levels in any organ in the RVG-MAT-9R/siRNA treated animals, both SOD1 mRNA and protein levels were significantly reduced in the brain, but not other organs in the RVG-9R/siRNA treated mice (FIG. 29b). To confirm that the observed knockdown is due to the specific delivery of siRNA within the brain, the inventors also tested for the presence of SOD1 siRNA in different organs of mice by Northern blot analysis using siRNA sense strand as probe. siRNA could be detected in the brain but not in the spleen or liver of treated mice (FIGS. 28a and 29c). Collectively the inventors have discovered that RVG-9R is able to deliver siRNA specifically to brain cells after iv administration, resulting in effective gene silencing in the brain.

Example 4

RVG-9R enables i.v treatment of viral encephalitis. The inventors have previously reported that intracranial treatment with antiviral siRNAs can provide near complete protection from fatal flaviviral encephalitis in mice[8]. However, a noninvasive iv treatment method would be optimal for siRNA therapy for clinical use, for example for clinical use in humans. The inventors demonstrated iv treatment with siRNA bound to RVG-9R can protect mice from fatal JEV-induced encephalitis. Unlike wild type mice, immunodeficient NOD/SCID mice used in these studies uniformly susceptible for peripheral infection with flaviviruses[20,21]. NOD/SCID mice were infected intraperitoneally with 5LD50 (lethal dose) of JEV, followed by after 4 hours an iv injection with 50 µg of antiviral FvE$^J$ siRNA (siFvE$^J$ as described in Kumar et al[8]) or an control luciferase siRNA (siLuc) complexed with RVG-9R or RV-MAT-9R. The siRNA treatment was repeated every day for at least 3 successive days and the mice were observed for survival for at least 30 days. Untreated mice, mice treated with either siFvE$^J$ complexed with RV-MAT-9R or with the control siLuc complexed with RVG-9R all died within 10 days, showing that neither the chimeric peptides by themselves or the control siLuc complexed with RVG-9R affected the course of the disease. In contrast, treatment with siFvE$^J$ complexed with RVG-9R resulted in ~80% survival as shown in FIG. 31a, and the surviving mice were observed, and did not show any signs of sickness or toxicity during the entire course of observation for 30 days (FIG. 30a). Moreover, while the brain sections of control siRNA treated sick mice revealed typical features of diffuse focal encephalitis marked by inflammatory cell infiltration and neuronal apoptosis, similar sections of RVG-9R/siRNA treated surviving mice were completely normal without any histopahological evidence of infection or toxicity (not shown).

The inventors also discovered the presence of siRNA in the brains of RVG-9R treated mice by Northern blot analysis (FIG. 30b). The inventors have also earlier reported that FvE$^J$ siRNA effects are indeed due to RNAi and not because of induction of non-specific IFN response[8]. However, to rule out the possibility that non-specific IFN production mediated the protection observed, and to rule out the possibility that FvE$^J$ siRNA complexed with RVG-9R can induce non-specific IFN responses, the inventors also measured serum IFN levels following RVG-9R/siRNA administration. Although, as expected IFN levels were elevated when mice were treated with a known immunostimulatory siRNA (βgal724)[22], IFN was not induced in RVG-9R/FvE$^J$ siRNA treated animals (FIG. 30c), demonstrating the protection is mediated by RNAi. Thus, iv treatment with RVG-9R/siRNA can be safely and effectively used for the treatment of fatal JEV infection.

It is likely that the siRNA is widely distributed within the brain because most cell types in the brain including neurons, astrocytes and glial cells express the α7 subunit of AchR[13].

Taken together, the inventors have discovered that an RVG peptide construct comprising SEQ ID NO:13 permits transvascular delivery of siRNA to the CNS. Although the exact mechanism by which such a construct (for example RVG-9R, RVG-11R or other RVG-containing constructs, or variants, derivatives or fragments thereof) enable BBB crossing is not known and not wishing to be bound by theory, because the RVG peptide alone (without 9R) was also able to enter the brain cells after iv injection (FIG. 27d), it is likely that receptor-mediated transcytosis via α7-10 subunit of the AchR (which is widely expressed in the brain including expression by brain capillary endothelial cells[13]) is involved in the process. The fact that RVG-9R, but not RV-MAT-9R was capable of facilitating BBB crossing also indicates that specific receptor binding can be important. Although cell penetrating peptides might also enable membrane crossing of cargo covalently conjugated at the terminus by unknown mechanisms[23,24,] receptor clustering mediated by a 10:1 molar ratio of siRNA/RVG-9R binding may be important for efficient transport of siRNA into the neuronal cells (particularly when the siRNA is non-covalently bound to the peptide) and this can explain the neuronal cell specificity of targeting by RVG-9R. Because the RVG-9R delivered siRNA was functional in gene silencing in multiple systems, it is likely that the siRNA detaches from the peptide inside the cell.

Similarly, siRNA complexed with protamine has also been reported to be released in the cytoplasm of cells by unknown mechanisms to mediate gene silencing[25]. The inventors have discovered that RVG-9R mediates transvascular delivery of siRNAs to the CNS. The inventors have discovered an intravenous RNAi-based treatment approach for flaviviral encephalitis, as well as RVG assisted brain delivery useful for delivery of a variety of other therapeutic molecules such as gene therapy vectors and small molecule drugs to the brain for the treatment of a wide variety of neurodegenerative diseases and disorders.

REFERENCES

The references cited below and throughout the specification are incorporated herein by reference in their entirety. All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

1. Lieberman, J., Song, E., Lee, S. K. & Shankar, P. Interfering with disease: opportunities and roadblocks to harnessing RNA interference. *Trends Mol Med* 9, 397-403 (2003).
2. Berkhout, B. RNA interference as an antiviral approach: targeting HIV-1. *Curr Opin Mol Ther* 6, 141-5 (2004).
1. Joost Haasnoot, P. C., Cupac, D. & Berkhout, B. Inhibition of virus replication by RNA interference. *J Biomed Sci* 10, 607-16 (2003).
2. Gitlin, L. & Andino, R. Nucleic acid-based immune system: the antiviral potential of mammalian RNA silencing. *J Virol* 77, 7159-65 (2003).
3. Wang, Q. C., Nie, Q. H. & Feng, Z. H. RNA interference: antiviral weapon and beyond. *World J Gastroenterol* 9, 1657-61 (2003).
4. Kumar P, Lee S K, Shankar P, Manjunath N. A single siRNA suppresses encephalitis induced by two flaviviruses. *PLoS Medicine*. April; 3(4):e96 (2006).
5. Gupta, B., Levchenko, T. S. & Torchilin, V. P. Intracellular delivery of large molecules and small particles by cell-penetrating proteins and peptides. *Adv Drug Deliv Rev* 57, 637-51 (2005).
6. Dietz, G. P. & Bahr, M. Peptide-enhanced cellular internalization of proteins in neuroscience. *Brain Res Bull* 68, 103-14 (2005).
7. Deshayes, S., Morris, M. C., Divita, G. & Heitz, F. Cell-penetrating peptides: tools for intracellular delivery of therapeutics. *Cell Mol Life Sci* 62, 1839-49 (2005).
8. Melikov, K. & Chemomordik, L. V. Arginine-rich cell penetrating peptides: from endosomal uptake to nuclear delivery. *Cell Mol Life Sci* 62, 2739-49 (2005).
9. Mazarakis, N. D. et al. Rabies virus glycoprotein pseudotyping of lentiviral vectors enables retrograde axonal transport and access to the nervous system after peripheral delivery. *Hum Mol Genet.* 10, 2109-21 (2001).
10. Tijsterman, M., Ketting, R. F. & Plasterk, R. H. The genetics of RNA silencing. *Annu Rev Genet.* 36, 489-519 (2002).
11. Dixon, R. A. Natural products and plant disease resistance. *Nature* 411, 843-7 (2001).
12. Plasterk, R. H. RNA silencing: the genome's immune system. *Science* 296, 1263-5 (2002).
13. Bernstein, E., Denli, A. M. & Hannon, G. J. The rest is silence. *Rna* 7, 1509-21 (2001).
14. Ahlquist, P. RNA-dependent RNA polymerases, viruses, and RNA silencing. *Science* 296, 1270-3 (2002).
15. Mello, C. C. & Conte, D., Jr. Revealing the world of RNA interference. *Nature* 431, 338-42 (2004).
16. Meister, G. & Tuschl, T. Mechanisms of gene silencing by double-stranded RNA. *Nature* 431, 343-9 (2004).
17. Hannon, G. J. & Rossi, J. J. Unlocking the potential of the human genome with RNA interference. *Nature* 431, 371-8 (2004).
18. Elbashir, S. M. et al. Duplexes of 21-nucleotide RNAs mediate RNA interference in cultured mammalian cells. *Nature* 411, 494-8 (2001).
19. Bertrand, J. R. et al. Comparison of antisense oligonucleotides and siRNAs in cell culture and in vivo. *Biochem Biophys Res Commun* 296, 1000-4 (2002).
20. Gitlin, L., Karelsky, S. & Andino, R. Short interfering RNA confers intracellular antiviral immunity in human cells. *Nature* 418, 430-4 (2002).
21. Bagasra, O. & Prilliman, K. R. RNA interference: the molecular immune system. *J Mol Histol* 35, 545-53 (2004).
22. Batik, S. Control of nonsegmented negative-strand RNA virus replication by siRNA. *Virus Res* 102, 27-35 (2004).
23. Novina, C. D. et al. siRNA-directed inhibition of HIV-1 infection. *Nat Med* 8, 681-6 (2002).
24. Song, E. et al. Sustained small interfering RNA-mediated human immunodeficiency virus type 1 inhibition in primary macrophages. *J Virol* 77, 7174-81 (2003).
25. Lee, S. K. et al. Lentiviral delivery of short hairpin RNAs protects CD4 T cells from multiple clades and primary isolates of HIV. *Blood* (2005).

26. Jiang, M. & Milner, J. Selective silencing of viral gene expression in HPV-positive human cervical carcinoma cells treated with siRNA, a primer of RNA interference. *Oncogene* 21, 6041-8 (2002).
27. Bitko, V., Musiyenko, A., Shulyayeva, O. & Batik, S Inhibition of respiratory viruses by nasally administered siRNA. *Nat Med* 11, 50-5 (2005).
28. Tompkins, S. M., Lo, C. Y., Tumpey, T. M. & Epstein, S. L. Protection against lethal influenza virus challenge by RNA interference in vivo. *Proc Natl Acad Sci USA* 101, 8682-6 (2004).
29. Palliser, D. et al. An siRNA-based microbicide protects mice from lethal herpes simplex virus 2 infection. *Nature* (2005).
30. Li, B. J. et al. Using siRNA in prophylactic and therapeutic regimens against SARS coronavirus in Rhesus macaque. *Nat Med* 11, 944-51 (2005).
31. Ptasznik, A., Nakata, Y., Kalota, A., Emerson, S. G. & Gewirtz, A. M. Short interfering RNA (siRNA) targeting the Lyn kinase induces apoptosis in primary, and drug-resistant, BCR-ABL1(+) leukemia cells. *Nat Med* 10, 1187-9 (2004).
32. Sumimoto, H. et al. Gene therapy for human small-cell lung carcinoma by inactivation of Skp-2 with virally mediated RNA interference. *Gene Ther* 12, 95-100 (2005).
33. Duxbury, M. S. et al. Systemic siRNA-mediated gene silencing: a new approach to targeted therapy of cancer. *Ann Surg* 240, 667-74; discussion 675-6 (2004).
34. Lakka, S. S. et al. Inhibition of cathepsin B and MMP-9 gene expression in glioblastoma cell line via RNA interference reduces tumor cell invasion, tumor growth and angiogenesis. *Oncogene* 23, 4681-9 (2004).
35. Zhang, Y. et al. Intravenous RNA interference gene therapy targeting the human epidermal growth factor receptor prolongs survival in intracranial brain cancer. *Clin Cancer Res* 10, 3667-77 (2004).
36. Miller, V. M. et al. Allele-specific silencing of dominant disease genes. *Proc Natl Acad Sci USA* 100, 7195-200 (2003).
37. Miller, V. M., Gouvion, C. M., Davidson, B. L. & Paulson, H. L. Targeting Alzheimer's disease genes with RNA interference: an efficient strategy for silencing mutant alleles. *Nucleic Acids Res* 32, 661-8 (2004).
38. Xia, H. et al. RNAi suppresses polyglutamine-induced neurodegeneration in a model of spinocerebellar ataxia. *Nat Med* 10, 816-20 (2004).
39. Buckingham, S. D., Esmaeili, B., Wood, M. & Sattelle, D. B. RNA interference: from model organisms towards therapy for neural and neuromuscular disorders. *Hum Mol Genet.* 13 Spec No 2, R275-88 (2004).
40. McCaffrey, A. P. et al. RNA interference in adult mice. *Nature* 418, 38-9 (2002).
41. Song, E. et al. RNA interference targeting Fas protects mice from fulminant hepatitis. *Nat Med* 9, 347-51 (2003).
42. Ge, Q. et al. Inhibition of influenza virus production in virus-infected mice by RNA interference. *Proc Natl Acad Sci USA* 101, 8676-81 (2004).
43. Miller, G. Drug targeting. Breaking down barriers. *Science* 297, 1116-8 (2002).
44. Schlachetzki, F., Zhang, Y., Boado, R. J. & Pardridge, W. M. Gene therapy of the brain: the transvascular approach. *Neurology* 62, 1275-81 (2004).
45. Doolittle, N. D. et al. Safety and efficacy of a multicenter study using intraarterial chemotherapy in conjunction with osmotic opening of the blood-brain barrier for the treatment of patients with malignant brain tumors. *Cancer* 88, 637-47 (2000).
46. Kroll, R. A. & Neuwelt, E. A. Outwitting the blood-brain barrier for therapeutic purposes: osmotic opening and other means. *Neurosurgery* 42, 1083-99; discussion 1099-100 (1998).
47. Muldoon, L. L. et al. Comparison of intracerebral inoculation and osmotic blood-brain barrier disruption for delivery of adenovirus, herpesvirus, and iron oxide particles to normal rat brain. *Am J Pathol* 147, 1840-51 (1995).
48. Borlongan, C. V., Emerich, D. F., Hoffer, B. J. & Bartus, R. T. Bradykinin receptor agonist facilitates lowdose cyclosporine-A protection against 6-hydroxydopamine neurotoxicity. *Brain Res* 956, 211-20 (2002).
49. Makimura, H., Mizuno, T. M., Mastaitis, J. W., Agami, R. & Mobbs, C. V. Reducing hypothalamic AGRP by RNA interference increases metabolic rate and decreases body weight without influencing food intake. *BMC Neurosci* 3, 18 (2002).
50. Xia, H., Mao, Q., Paulson, H. L. & Davidson, B. L. siRNA-mediated gene silencing in vitro and in vivo. *Nat Biotechnol* 20, 1006-10 (2002).
51. Hommel, J. D., Sears, R. M., Georgescu, D., Simmons, D. L. & DiLeone, R. J. Local gene knockdown in the brain using viral-mediated RNA interference. *Nat Med* 9, 1539-44 (2003).
52. Van den Haute, C., Eggermont, K., Nuttin, B., Debyser, Z. & Baekelandt, V. Lentiviral vector-mediated delivery of short hairpin RNA results in persistent knockdown of gene expression in mouse brain. *Hum Gene Ther* 14, 1799-807 (2003).
53. Naldini, L. et al. In vivo gene delivery and stable transduction of nondividing cells by a lentiviral vector. *Science* 272, 263-7 (1996).
54. Blomer, U. et al. Highly efficient and sustained gene transfer in adult neurons with a lentivirus vector. *J Virol* 71, 6641-9 (1997).
55. Raoul, C. et al. Lentiviral-mediated silencing of SOD1 through RNA interference retards disease onset and progression in a mouse model of ALS. *Nat Med* 11, 423-8 (2005).
56. Ralph, G. S. et al. Silencing mutant SOD1 using RNAi protects against neurodegeneration and extends survival in an ALS model. *Nat Med* 11, 429-33 (2005).
57. Cao, L. et al. VEGF links hippocampal activity with neurogenesis, learning and memory. *Nat Genet.* 36, 827-35 (2004).
58. Harper, S. Q. et al. RNA interference improves motor and neuropathological abnormalities in a Huntington's disease mouse model. *Proc Natl Acad Sci USA* 102, 5820-5 (2005).
59. Thakker, D. R., Hoyer, D. & Cryan, J. F. Interfering with the brain: Use of RNA interference for understanding the pathophysiology of psychiatric and neurological disorders. *Pharmacol Ther* (2005).
60. Marshall, E. Gene therapy. Second child in French trial is found to have leukemia. *Science* 299, 320 (2003).
61. Hacein-Bey-Abina, S. et al. A serious adverse event after successful gene therapy for X-linked severe combined immunodeficiency. *N Engl J Med* 348, 255-6 (2003).
62. Omi, K., Tokunaga, K. & Hohjoh, H. Long-lasting RNAi activity in mammalian neurons. *FEBS Lett* 558, 89-95 (2004).

63. Isacson, R., Kull, B., Salmi, P. & Wahlestedt, C. Lack of efficacy of 'naked' small interfering RNA applied directly to rat brain. *Acta Physiol Scand* 179, 173-7 (2003).
64. Hassani, Z. et al. Lipid-mediated siRNA delivery down-regulates exogenous gene expression in the mouse brain at picomolar levels. *J Gene Med* 7, 198-207 (2005).
65. Thakker, D. R. et al. Neurochemical and behavioral consequences of widespread gene knockdown in the adult mouse brain by using nonviral RNA interference. *Proc Natl Acad Sci USA* 101, 17270-5 (2004).
66. Thakker, D. R. et al. siRNA-mediated knockdown of the serotonin transporter in the adult mouse brain. *Mol Psychiatry* (2005).
67. Allerson, C. R. et al. Fully 2'-modified oligonucleotide duplexes with improved in vitro potency and stability compared to unmodified small interfering RNA. *J Med Chem* 48, 901-4 (2005).
68. Elmen, J. et al. Locked nucleic acid (LNA) mediated improvements in siRNA stability and functionality. *Nucleic Acids Res* 33, 439-47 (2005).
69. Layzer, J. M. et al. In vivo activity of nuclease-resistant siRNAs. *Rna* 10, 766-71 (2004).
70. Li, Z. Y., Mao, H., Kallick, D. A. & Gorenstein, D. G. The effects of thiophosphate substitutions on native siRNA gene silencing. *Biochem Biophys Res Commun* 329, 1026-30 (2005).
71. Soutschek, J. et al. Therapeutic silencing of an endogenous gene by systemic administration of modified siRNAs. *Nature* 432, 173-8 (2004).
72. Krutzfeldt, J. et al. Silencing of microRNAs in vivo with 'antagomirs'. *Nature* 438, 685-9 (2005).
73. Dorn, G. et al. siRNA relieves chronic neuropathic pain. *Nucleic Acids Res* 32, e49 (2004).
74. Shi, N. & Pardridge, W. M. Noninvasive gene targeting to the brain. *Proc Natl Acad Sci USA* 97, 7567-72 (2000).
75. Shi, N., Boado, R. J. & Pardridge, W. M. Antisense imaging of gene expression in the brain in vivo. *Proc Natl Acad Sci USA* 97, 14709-14 (2000).
76. Shi, N., Boado, R. J. & Pardridge, W. M. Receptor-mediated gene targeting to tissues in vivo following intravenous administration of pegylated immunoliposomes. *Pharm Res* 18, 1091-5 (2001).
77. Shi, N., Zhang, Y., Zhu, C., Boado, R. J. & Pardridge, W. M. Brain-specific expression of an exogenous gene after i.v. administration. *Proc Natl Acad Sci USA* 98, 12754-9 (2001).
78. Zhu, C. et al. Organ-specific expression of the lacZ gene controlled by the opsin promoter after intravenous gene administration in adult mice. *J Gene Med* 6, 906-12 (2004).
79. Zhang, Y., Schlachetzki, F. & Pardridge, W. M. Global non-viral gene transfer to the primate brain following intravenous administration. *Mol Ther* 7, 11-8 (2003).
80. Zhang, Y., Boado, R. J. & Pardridge, W. M. In vivo knockdown of gene expression in brain cancer with intravenous RNAi in adult rats. *J Gene Med* 5, 1039-45 (2003).
81. B. N. Fields, D. M. K., P. M. Howley (ed.) *Field's Virology*, 931-952 (Lippincott-Raven, Philadelphia, 1996).
82. Biggerstaff, B. J. & Petersen, L. R. Estimated risk of transmission of the West Nile virus through blood transfusion in the US, 2002. *Transfusion* 43, 1007-17 (2003).
83. Tyler, K. L. West Nile virus infection in the United States. *Arch Neurol* 61, 1190-5 (2004).
84. Solomon, T. Flavivirus encephalitis. *N Engl J Med* 351, 370-8 (2004).
85. Gondi, C. S. et al. RNAi-mediated inhibition of cathepsin B and uPAR leads to decreased cell invasion, angiogenesis and tumor growth in gliomas. *Oncogene* 23, 8486-96 (2004).
86. Rubinson, D. A. et al. A lentivirus-based system to functionally silence genes in primary mammalian cells, stem cells and transgenic mice by RNA interference. *Nat Genet.* 33, 401-6 (2003).
87. Rey, F. A., Heinz, F. X., Mandl, C., Kunz, C. & Harrison, S. C. The envelope glycoprotein from tickborne encephalitis virus at 2 A resolution. *Nature* 375, 291-8 (1995).
88. Du, Q., Thonberg, H., Wang, J., Wahlestedt, C. & Liang, Z. A systematic analysis of the silencing effects of an active siRNA at all single-nucleotide mismatched target sites. *Nucleic Acids Res* 33, 1671-7 (2005).
89. Lentz, T. L., Wilson, P. T., Hawrot, E. & Speicher, D. W. Amino acid sequence similarity between rabies virus glycoprotein and snake venom curaremimetic neurotoxins. *Science* 226, 847-8 (1984).
90. Lentz, T. L., Burrage, T. G., Smith, A. L., Crick, J. & Tignor, G. H. Is the acetylcholine receptor a rabies virus receptor? *Science* 215, 182-4 (1982).
91. Lafon, M. Rabies virus receptors. *J Neurovirol* 11, 82-7 (2005).
92. Lentz, T. L. Rabies virus binding to an acetylcholine receptor alpha-subunit peptide. *J Mol Recognit* 3, 82-8 (1990).
93. Lentz, T. L. Structure-function relationships of curaremimetic neurotoxin loop 2 and of a structurally similar segment of rabies virus glycoprotein in their interaction with the nicotinic acetylcholine receptor. *Biochemistry* 30, 10949-57 (1991).
94. Notter, M. F. & Leary, J. F. Flow cytometric analysis of tetanus toxin binding to neuroblastoma cells. *J Cell Physiol* 125, 476-84 (1985).
95. Chen, T. J., Chen, S. S., Wu, R. E., Wang, D. C. & Lin, C. H. Implication of nNOS in the enlargement of AChR aggregates but not the initial aggregate formation in a novel coculture model. *Chin J Physiol* 48, 129-38 (2005).
96. Gotti, C. & Clementi, F. Neuronal nicotinic receptors: from structure to pathology. *Prog Neurobiol* 74, 363-96 (2004).
97. Chiu, Y. L., Ali, A., Chu, C. Y., Cao, H. & Rana, T. M. Visualizing a correlation between siRNA localization, cellular uptake, and RNAi in living cells. *Chem Biol* 11, 1165-75 (2004).
98. Wender, P. A. et al. The design, synthesis, and evaluation of molecules that enable or enhance cellular uptake: peptoid molecular transporters. *Proc Natl Acad Sci USA* 97, 13003-8 (2000).
99. Lu, C., Shimaoka, M., Salas, A. & Springer, T. A. The binding sites for competitive antagonistic, allosteric antagonistic, and agonistic antibodies to the domain of integrin LFA-1. *J Immunol* 173, 3972-8 (2004).
100. Donnelly-Roberts, D. L. & Lentz, T. L. Structural and conformational similarity between synthetic peptides of curaremimetic neurotoxins and rabies virus glycoprotein. *Brain Res Mol Brain Res* 11, 107-13 (1991).
101. Dietzschold, B., Schnell, M. & Koprowski, H. Pathogenesis of rabies. *Curr Top Microbiol Immunol* 292, 45-56 (2005).
102. Plakhov, I. V., Arlund, E. E., Aoki, C. & Reiss, C. S. The earliest events in vesicular stomatitis virus infection of the murine olfactory neuroepithelium and entry of the central nervous system. *Virology* 209, 257-62 (1995).

103. Lafay, F. et al. Spread of the CVS strain of rabies virus and of the avirulent mutant AvO1 along the olfactory pathways of the mouse after intranasal inoculation. *Virology* 183, 320-30 (1991).
104. Kilic, E., Kilic, U. & Hermann, D. M. TAT fusion proteins against ischemic stroke: Current status and future perspectives. *Front Biosci* 11, 1716-21 (2006).
105. Diem, R. et al. HIV-Tat-mediated Bcl-xL delivery protects retinal ganglion cells during experimental autoimmune optic neuritis. *Neurobiol Dis* 20, 218-26 (2005).
106. Yin, W. et al. TAT-mediated delivery of Bcl-xL protein is neuroprotective against neonatal hypoxicischemic brain injury via inhibition of caspases and AIF. *Neurobiol Dis* (2005).
107. Pesola, J. M., Zhu, J., Knipe, D. M. & Coen, D. M. Herpes simplex virus 1 immediate-early and early gene expression during reactivation from latency under conditions that prevent infectious virus production. *J Virol* 79, 14516-25 (2005).
108. Shah, K. et al. Glioma therapy and real-time imaging of neural precursor cell migration and tumor regression. *Ann Neurol* 57, 34-41 (2005).
109. Shah, K. et al. In vivo imaging of HIV protease activity in amplicon vector-transduced gliomas. *Cancer Res* 64, 273-8 (2004).
110. Tang, Y. et al. In vivo tracking of neural progenitor cell migration to glioblastomas. *Hum Gene Ther* 14, 1247-54 (2003).
111. Shah, K., Tang, Y., Breakefield, X. & Weissleder, R. Real-time imaging of TRAIL-induced apoptosis of glioma tumors in vivo. *Oncogene* 22, 6865-72 (2003).
112. Schiffelers, R. M. et al. Cancer siRNA therapy by tumor selective delivery with ligand-targeted sterically stabilized nanoparticle. *Nucleic Acids Res* 32, e149 (2004).
113. Zhang, W. et al. Inhibition of respiratory syncytial virus infection with intranasal siRNA nanoparticles targeting the viral NS1 gene. *Nat Med* 11, 56-62 (2005).
114. Hu-Lieskovan, S., Heidel, J. D., Bartlett, D. W., Davis, M. E. & Triche, T. J. Sequence-specific knockdown of EWS-FLI1 by targeted, nonviral delivery of small interfering RNA inhibits tumor growth in a murine model of metastatic Ewing's sarcoma. *Cancer Res* 65, 8984-92 (2005).
115. Kulkarni, R. P., Mishra, S., Fraser, S. E. & Davis, M. E. Single cell kinetics of intracellular, nonviral, nucleic acid delivery vehicle acidification and trafficking *Bioconjug Chem* 16, 986-94 (2005).
116. Davis, M. E. & Brewster, M. E. Cyclodextrin-based pharmaceutics: past, present and future. *Nat Rev Drug Discov* 3, 1023-35 (2004).
117. Bellocq, N. C. et al. Synthetic biocompatible cyclodextrin-based constructs for local gene delivery to improve cutaneous wound healing. *Bioconjug Chem* 15, 1201-11 (2004).
118. Pun, S. H. et al. Cyclodextrin-modified polyethylenimine polymers for gene delivery. *Bioconjug Chem* 15, 831-40 (2004).
119. Pun, S. H. et al. Targeted delivery of RNA-cleaving DNA enzyme (DNAzyme) to tumor tissue by transferrin-modified, cyclodextrin-based particles. *Cancer Biol Ther* 3, 641-50 (2004).
120. Davis, M. E. et al. Self-assembling nucleic acid delivery vehicles via linear, water-soluble, cyclodextrincontaining polymers. *Curr Med Chem* 11, 179-97 (2004).
121. Bellocq, N. C., Pun, S. H., Jensen, G. S. & Davis, M. E. Transferrin-containing, cyclodextrin polymerbased particles for tumor-targeted gene delivery. *Bioconjug Chem* 14, 1122-32 (2003).
122. Metselaar, J. M. & Storm, G. Liposomes in the treatment of inflammatory disorders. *Expert Opin Drug Deliv* 2, 465-76 (2005).
123. Torchilin, V. P. Recent advances with liposomes as pharmaceutical carriers. *Nat Rev Drug Discov* 4, 145-60 (2005).
124. Peer, D., Florentin, A. & Margalit, R. Hyaluronan is a key component in cryoprotection and formulation of targeted unilamellar liposomes. *Biochim Biophys Acta* 1612, 76-82 (2003).
125. Peer, D. & Margalit, R. Physicochemical evaluation of a stability-driven approach to drug entrapment in regular and in surface-modified liposomes. *Arch Biochem Biophys* 383, 185-90 (2000).
126. Peer, D. & Margalit, R. Loading mitomycin C inside long circulating hyaluronan targeted nanoliposomes increases its antitumor activity in three mice tumor models. *Int J Cancer* 108, 780-9 (2004).
127. Peer, D. & Margalit, R. Tumor-targeted hyaluronan nanoliposomes increase the antitumor activity of liposomal Doxorubicin in syngeneic and human xenograft mouse tumor models. *Neoplasia* 6, 343-53 (2004).
128. Zhang, Y., Schlachetzki, F., Li, J. Y., Boado, R. J. & Pardridge, W. M. Organ-specific gene expression in the rhesus monkey eye following intravenous non-viral gene transfer. *Mol Vis* 9, 465-72 (2003).
129. Huber, J. D., Egleton, R. D. & Davis, T. P. Molecular physiology and pathophysiology of tight junctions in the blood-brain barrier. *Trends Neurosci* 24, 719-25 (2001).
130. Akdemir, H., Selcuklu, A., Pasaoglu, A., Oktem, I. S. & Kavuncu, I. Treatment of severe intraventricular hemorrhage by intraventricular infusion of urokinase. *Neurosurg Rev* 18, 95-100 (1995).
131. Vincken, W., Meysman, M., Verbeelen, D., Lauwers, S. & D'Haens, J. Intraventricular rifampicin in severe tuberculous meningo-encephalitis. *Eur Respir J* 5, 891-3 (1992).
132. Elgamal, E. A. & Murshid, W. R. Intracavitary administration of amphotericin B in the treatment of cerebral aspergillosis in a non immune-compromised patient: case report and review of the literature. *Br J Neurosurg* 14, 137-41 (2000).
133. Rawicki, B. Treatment of cerebral origin spasticity with continuous intrathecal baclofen delivered via an implantable pump: long-term follow-up review of 18 patients. *J Neurosurg* 91, 733-6 (1999).
134. Kamensek, J. Continuous intrathecal baclofen infusions. An introduction and overview. *Axone* 20, 93-8 (1999).
135. Dario, A. & Tomei, G. A benefit-risk assessment of baclofen in severe spinal spasticity. *Drug Saf* 27, 799-818 (2004).
136. Uhrbom, L., Nerio, E. & Holland, E. C. Dissecting tumor maintenance requirements using bioluminescence imaging of cell proliferation in a mouse glioma model. *Nat Med* 10, 1257-60 (2004).
137. Saydam, O. et al. Herpes simplex virus 1 amplicon vector-mediated siRNA targeting epidermal growth factor receptor inhibits growth of human glioma cells in vivo. *Mol Ther* 12, 803-12 (2005).
138. Bloom, D. C. HSV LAT and neuronal survival. *Int Rev Immunol* 23, 187-98 (2004).

139. Yarom, N., Buchner, A. & Dayan, D. Herpes simplex virus infection: part I—Biology, clinical presentation and latency. *Refuat Hapeh Vehashinayim* 22, 7-15, 84 (2005).
140. Bystricka, M. & Russ, G. Immunity in latent Herpes simplex virus infection. *Acta Virol* 49, 159-67 (2005).
141. Decman, V., Freeman, M. L., Kinchington, P. R. & Hendricks, R. L. Immune control of HSV-1 latency. *Viral Immunol* 18, 466-73 (2005).
142. Thompson, R. L. & Sawtell, N. M. The herpes simplex virus type 1 latency-associated transcript gene regulates the establishment of latency. *J Virol* 71, 5432-40 (1997).
143. Perng, G. C. et al. Virus-induced neuronal apoptosis blocked by the herpes simplex virus latencyassociated transcript. *Science* 287, 1500-3 (2000).
144. Thompson, R. L. & Sawtell, N. M. Herpes simplex virus type 1 latency-associated transcript gene promotes neuronal survival. *J Virol* 75, 6660-75 (2001).
145. Bhuyan, P. K. et al. Short interfering RNA-mediated inhibition of herpes simplex virus type 1 gene expression and function during infection of human keratinocytes. *J Virol* 78, 10276-81 (2004).
146. Peng, W. et al. Mapping herpes simplex virus type 1 latency-associated transcript sequences that protect from apoptosis mediated by a plasmid expressing caspase-8. *J Neurovirol* 10, 260-5 (2004).
147. Jin, L. et al. Identification of herpes simplex virus type 1 latency-associated transcript sequences that both inhibit apoptosis and enhance the spontaneous reactivation phenotype. *J Virol* 77, 6556-61 (2003).
148. Wang, Q. Y. et al. Herpesviral latency-associated transcript gene promotes assembly of heterochromatin on viral lytic-gene promoters in latent infection. *Proc Natl Acad Sci USA* 102, 16055-9 (2005).
149. Higaki, S., Deai, T., Fukuda, M. & Shimomura, Y. Microarray analysis in the HSV-1 latently infected mouse trigeminal ganglion. *Cornea* 23, S42-7 (2004).
150. Jin, L. et al. A herpes simplex virus type 1 mutant expressing a baculovirus inhibitor of apoptosis gene in place of latency-associated transcript has a wild-type reactivation phenotype in the mouse. *J Virol* 79, 12286-95 (2005).
151. Sharma, S., Zhou, Y. & Singh, B. R. Cloning, expression, and purification of C-terminal quarter of the heavy chain of botulinum neurotoxin type A. *Protein Expr Purif* (2005).
152. Zhou, Y. & Singh, B. R. Cloning, high-level expression, single-step purification, and binding activity of His6-tagged recombinant type B botulinum neurotoxin heavy chain transmembrane and binding domain. *Protein Expr Purif* 34, 8-16 (2004).
153. Lentz, T. L., Burrage, T. G., Smith, A. L., Crick, J. & Tignor, G. H. Is the acetylcholine receptor a rabies virus receptor? *Science* 215, 182-4 (1982).
154. Lafon, M. Rabies virus receptors. *J Neurovirol* 11, 82-7 (2005).
155. Rubinson, D. A. et al. A lentivirus-based system to functionally silence genes in primary mammalian cells, stem cells and transgenic mice by RNA interference. *Nat Genet.* 33, 401-6 (2003).
156. Mazarakis, N. D. et al. Rabies virus glycoprotein pseudotyping of lentiviral vectors enables retrograde axonal transport and access to the nervous system after peripheral delivery. *Hum Mol Genet.* 10, 2109-21 (2001).
157. Kumar, P., Lee, S. K., Shankar, P. & Manjunath, N. A Single siRNA Suppresses Fatal Encephalitis Induced by Two Different Flaviviruses. *PLoS Med* 3, e96 (2006).
158. Judge, A. D. et al. Sequence-dependent stimulation of the mammalian innate immune response by synthetic siRNA. *Nat Biotechnol* 23, 457-62 (2005).

---

The invention claimed is:

1. A chimeric peptide comprising the amino acid sequence of SEQ ID NO: 13 and a cell permeable peptide.

2. The chimeric peptide of claim 1, wherein the cell permeable peptide is located at the C-terminus of SEQ ID NO: 13.

3. The chimeric peptide of claim 1, wherein the cell permeable peptide is selected from the group consisting of SEQ ID NO: 1-12, and 17-32.

4. The chimeric peptide of claim 1, wherein the cell permeable peptide is a polymer consisting of arginine residues.

5. The chimeric peptide of claim 4, wherein the number of the arginine residues in the polymer ranges from about 3 to about 11 residues.

6. The chimeric peptide of claim 5, wherein at least one of the arginine residues is a D-arginine isomer.

7. The chimeric peptide of claim 1, wherein the cell permeable peptide is a protamine peptide.

8. The chimeric peptide of claim 1, wherein the chimeric peptide is selected from the group consisting of SEQ ID NO: 14, 15, 16, and 34.

9. A composition for targeted delivery to neuronal cells comprising at least one chimeric peptide of claim 1 and at least one effector agent.

10. The composition of claim 9, wherein the at least one effector agent comprises a nucleic acid for the targeted delivery of the nucleic acid into neuronal cells.

11. The composition of claim 10, wherein the nucleic acid is an siRNA or a viral vector DNA.

12. The composition of claim 9, wherein the at least one effector agent is a therapeutic agent for the targeted delivery of the therapeutic agent into neuronal cells.

13. The composition of claim 9, wherein the at least one effector agent is a diagnostic agent or imaging agent for the targeted delivery of the diagnostic or imaging agent into neuronal cells.

14. A method of targeted delivery to neuronal cells comprising contacting the cells with at least one chimeric peptide of claim 1 or a composition comprising at least one chimeric peptide of claim 1.

15. A synthetic peptide comprising SEQ ID NO: 34.

16. The synthetic peptide of claim 15, prepared as a dry powder.

* * * * *